(12) United States Patent
Mojzita et al.

(10) Patent No.: US 11,952,580 B2
(45) Date of Patent: Apr. 9, 2024

(54) HETEROLOGOUS PRODUCTION OF PSILOCYBIN

(71) Applicant: TEKNOLOGIAN TUTKIMUSKESKUS VTT OY, Espoo (FI)

(72) Inventors: Dominik Mojzita, Espoo (FI); Heiko Rischer, Espoo (FI); Anssi Rantasalo, Espoo (FI); Kirsi-Marja Oksman-Caldentey, Espoo (FI); Joosu Kuivanen, Espoo (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 80 days.

(21) Appl. No.: 16/980,710

(22) PCT Filed: Mar. 11, 2019

(86) PCT No.: PCT/FI2019/050199
§ 371 (c)(1),
(2) Date: Sep. 14, 2020

(87) PCT Pub. No.: WO2019/180309
PCT Pub. Date: Sep. 26, 2019

(65) Prior Publication Data
US 2021/0010015 A1    Jan. 14, 2021

(30) Foreign Application Priority Data
Mar. 19, 2018 (FI) .................................... 20185254

(51) Int. Cl.
*C12N 15/82*   (2006.01)
*C12N 9/10*    (2006.01)
*C12N 15/52*   (2006.01)

(52) U.S. Cl.
CPC ....... *C12N 15/8243* (2013.01); *C12N 9/1007* (2013.01); *C12N 15/52* (2013.01)

(58) Field of Classification Search
CPC ... C12N 15/52; C12N 9/1007; C12N 15/8243
See application file for complete search history.

(56) References Cited

U.S. PATENT DOCUMENTS

2018/0057806 A1†   3/2018   Romney
2021/0108238 A1*   4/2021   Protzko ............... C12N 9/0042

FOREIGN PATENT DOCUMENTS

WO      2017144777 A1      8/2017
WO   WO-2017144777 A1 *   8/2017   ........... C12N 15/625

OTHER PUBLICATIONS

Prasad, Rajendra, Peter Niederberger, and Ralf Hütter. "Tryptophan accumulation in *Saccharomyces cerevisiae* under the influence of an artificial yeast TRP gene cluster." Yeast 3.2 (1987): 95-105. (Year: 1987).*

Graf RO, Mehmann BR, Braus GH. Analysis of feedback-resistant anthranilate synthases from *Saccharomyces cerevisiae*. Journal of bacteriology. Feb. 1993;175(4):1061-8. (Year: 1993).*

Rantasalo,A., Czeizler,E., Virtanen, R., Rousu,J., Lahdesmaki,H., Penttila,M., Jantti,J. and Mojzita,D. (2016) Synthetic transcription amplifier system for orthogonal control of gene expression in *Saccharomyces cerevisiae*. PLoS One, 11, e0148320. (Year: 2016).*

Fricke, J., Blei, F., Hoffmeister, D., 2017. Enzymatic synthesis of psilocybin. Angew. Chemie Int. Ed. 56, 12352-12355. (Year: 2017).*

Irvine, William, Marshall Tyler, and Rupika Delgoda. "In silico characterization of the psilocybin biosynthesis pathway." Computational Biology and Chemistry 104 (2023): 107854. (Year: 2023).*

Fricke, J. et al. Enzymatic Synthesis of Psilocybin. In: Angewandte Chemie Int. Ed. Engl. Wiley-VCH Verlag GmbH & Co., Aug. 2017 , vol. 56, 12352-12355, DOI:10.1002/anie.201705489> the whole document, especially abstract; p. 12353, first two paragraphs in left column; Fig. 1 & Supporting Information pp. 2-4; table S1, Fig. S1.

Rantasalo, A. et al. Synthetic Transcription Amplifier System for Orthogonal Control of Gene Expression in *Saccharomyces cerevisiae*. In: PLoS One Feb. 2016, vol. 11, No. 2, 1-19, <DOI:10.1371/journal.pone.0148320> the whole document, especially abstract; p. 2, "Material and Methods" chapter; Fig. 2.

Reynolds, H.T. et al. Horizontal gene cluster transfer increased hallucinogenic mushroom diversity. In: Evolution Letters. Wiley Periodicals, Inc., Feb. 2018, vol. 2, 88-101, <DOI:10.1002/evl3.42> the whole document, especially abstract; pp. 90-91, chapter "Confirmation of psilocybin gene cluster enzyme activity"; pp. 97-98, chapter "Analyses of enzyme function".

Kang, S. et al. Characterization of rice tryptophan decarboxylases and their direct involvement in serotonin biosynthesis in transgenic rice. In: Planta Springer-Verlag, Dec. 2007, vol. 227, 263-272, <DOI:10.1007/s00425-007-0614-z> the whole document, especially abstract; pp. 264-265 chapters "Bacterial expression studies and enzyme purification", "Isolation and analysis of nucleic acids"; p. 266, right column; Fig. 2.

Ikeda, M. Towards bacterial strains overproducing l-tryptophan and other aromatics by metabolic engineering. In: Appl Microbiol Biotechnol Springer-Verlag, Jan. 2006, vol. 69, 615-626, <DOI:10.1007/s00253-005-0252-y> the whole document, especially chapter "Engineering of the common pathway and l-tryptophan branch"; Fig. 2.

(Continued)

*Primary Examiner* — Weihua Fan
(74) *Attorney, Agent, or Firm* — Robert P. Michal, Esq.; Carter, DeLuca & Farrell LLP

(57) ABSTRACT

A recombinant host cell is disclosed for producing psilocybin and related compounds, such as metabolic intermediates of the psilocybin biosynthesis. Also provided is a method of producing psilocybin and its synthesis intermediates and related compounds, such as metabolic intermediates of the psilocybin biosynthesis, in the host cell, as well as a production system for producing them.

11 Claims, 16 Drawing Sheets
Specification includes a Sequence Listing.

(56) References Cited

OTHER PUBLICATIONS

Database CAS Registry [online] Sep. 12, 2017 (Sep. 12, 2017) Accession No. (CAS Registry number, RN) 2126871-54-1 [retrieved on Jun. 13, 2018] Retrieved from: Registry database through STN Express & Sequence alignments between RN: 2126871-54-1 and polynucleotide sequences SEQ ID No. 1 and 9 of the current application.

Database CAS Registry [online] Sep. 12, 2017 (Sep. 12, 2017) Accession No. (CAS Registry number, RN) 2126871-60-9 [retrieved on Jun. 13, 2018] Retrieved from: Registry database through STN Express & Sequence alignments between RN: 2126871-60-9 polynucleotide sequences SEQ ID No. 2 and 10 of the current application.

Hoefgen Sandra et al: "Facile assembly and fluorescence-based screening method for heterologous expression of biosynthetic pathways in fungi", Metabolic Engineering, Academic Press, US, vol. 48, May 26, 2018 (May 26, 2018), pp. 44-51, XP085437931, ISSN: 1096-7176, DOI: 10.1016/J.YMBEN.2018.05.014 the whole document.

Felix Blei et al: "Biocatalytic Production of Psilocybin and Derivatives in Tryptophan Synthase-Enhanced Reactions", Chemistry—A European Journal, vol. 24, No. 40, Jun. 19, 2018 (Jun. 19, 2018), pp. 10028-10031, XP055584692, DE ISSN: 0947-6539, DOI: 10.1002/chem.201801047 the whole document.

Sherwood AM, Prisinzano TE 2018 Novel psychotherapeutics—a cautiously optimistic focus on hallucinogens. Expert Rev Clin Pharmacol 11: 1-3.

Tyls F, et al. 2014 Psilocybin—summary of knowledge and new perspectives. Eur Neuropsychopharmacol 24: 342-356.

Passie T, et al. 2002 The pharmacology of psilocybin. Addict Biol 7: 357-364.

Shirota O, et al. 2003 Concise large-scale synthesis of psilocin and psilocybin, principal hallucinogenic constituents of "magic mushroom". J Nat Prod 66: 885-887.

International Search Report issued by the European Patent Office acting as the International Searching Authority in relation to International Applicaiton No. PCT/FI2019/050199 dated May 10, 2019 (5 pages).

Written Opinion of the International Searching Authority issued by the European Patent Office acting as the International Searching Authority in relation to International Applicaiton No. PCT/FI2019/050199 dated May 10, 2019 (6 pages).

International Preliminary Report on Patentability issued by the European Patent Office acting as the International Preliminary Examining Authority in relation to International Applicaiton No. PCT/FI2019/050199 dated Jun. 23, 2020 (9 pages).

Finnish Search Report issued by the Finnish Patent and Registration Office in relation to Finnish Application No. 20185254 dated Jul. 5, 2018 (3 pages).

\* cited by examiner
† cited by third party

Fig 11

| Percent Identity Matrix | An_Aro4 | Sc_Aro4 | Pk_Aro4 |
|---|---|---|---|
| An_Aro4 | 100.0 % | 63.89 % | 61.90 % |
| Sc_Aro4 | 63.89 % | 100.0 % | 67.22 % |
| Pk_Aro4 | 61.90 % | 67.22 % | 100.0 % |

```
Nt_Trp2    1 MQSLPISHRLFPATHRKVLPLAVFSCRSSGGSLSRVRTLQCRCRSSGLPDEDRFIESGKSGRLIFFQKIDTSQHLTP
Sc_Trp2    1 ------------------------MASI----KHLFDIDSLKQLC--QQSODSSILPYPVYFYLPSLDLTP
An_Trp2    1 ------------------------APPI----SIVPSLEAGQVI-AGSKHAQPPNLLPLTSPALLLTP
Af_Trp2    1 ------------------------MTQT----SIVPSLEARRVI-NHSRTAKYPNLLPLTANIPADLLTP

Nt_Trp2   81 VLAYRCLVKE----DDREAPSFLTRSVEPGFRGGSVGRYSVVGAQPSMELVAKEHNVTILDHHTGKLTQKTVQDPMTH
Sc_Trp2   43 HVAYLRIIQLN--NPDREFSFLLESAK----TNNELDRYSFHGISPRKLIKTGFTE----------GIEPDPLET
An_Trp2   45 TLAYLRIAERCANVIGLSRSKLSFLYESAA----TTETIGRYSFVGAGPRELIKTGPGH----------GPECDPLVI
Af_Trp2   44 TLAYLRIAERK-----SKLSFLYESAA----TTETIGRYSFVGASVKRIKTGPGH----------GPECDPLVI

Nt_Trp2  155 PRCISEEHKP-RLVDELPDTFCGWYGVTSYDTVRYVNRKLPFLRAPEFDRNLADIQLGTEDVVPDEVEKKAHVHW
Sc_Trp2  102 HEKPSGTIVAENV-PGLPDLLGGAIGYISDCVRYFEPKTEPL---KDVLPTFAYLGQTIAFEVFQSQITWN
An_Trp2  109 LEKELSGDIVATVPGLTLPPLTGGAIGYVGYDCVRYFEPKTARPL---KDLGSPESLVSLFDTIVAFDEEFQVKVITV
Af_Trp2   99 LEKELSGDIVATVPGLTLPPLTGGAIGYVGYDCVRYFEPKTARPL---KDVLGIPESLVSFTIVAFDEEFQVKVITN

Nt_Trp2  234 VRLDQY-SDRDAWLDGKKRSEILVSRVQGIESPRLSPGSVDFCTHTFGRS----LTKGHMTSRETKNAULQARTEHIAAG
Sc_Trp2  178 DN--TPKTSLEKFYQAAAQTITDIVSKHTDDSSI----------PVPDGFTIKLQTESSGREGYEHVTLRKEISKG
An_Trp2  186 ISLPGNDSRIEVYTRQGQSYLQRTIDVLLI--PDY-----TLPPQGPIIMNQRYTSNIGREGYENVTRLKEHISKG
Af_Trp2  176 DRSGRLSDEARYRSQDLLQGHIDLILR--PEC-----FLPPQGPIIMNQRYTSNIGREGYEHVTRLKEHISKG

Nt_Trp2  309 DIFQIVLSQRFERRIFADFFEVTRALSHVNPSPYMTHYIQARGCILVASSPEDITRV-KGRMITNRPIAGTSRGKTPDEH
Sc_Trp2  248 DILQGVSQRVARPTSLHPFNLIRHLRTVNPSPYLFYIDCLDFQLIGASPELLLCHSDSKMQITHPIAGTVKRGGTGEED
An_Trp2  256 DIFQTVPSQRLSRPTSLHPFNLVRHLRTVNPSPYLFYIDCEDFQLVGASPELLVKE-EKGRIITHPIAGTVRRGKTPEED
Af_Trp2  246 DIFQTVPSQRLSRPTSLHPFNLVRHLRTVNPSPYLFYIDCEDFQLVGASPELLVKE-EKGRIITHPIAGTVKRGKSDEED

Nt_Trp2  388 VKHEMQMLKDERQCAEHQSLVDLQRNDVGKVSKPCSVNVHELMSVERYSHVQHLSHTVSGEHLDRHLQCWDHLIIBAALQVGH
Sc_Trp2  328 DALADQLRGSLKDRAEHVMLVDLARNDVNRQCDPLTTQVDFLTIQKFSHVQHLVSQVSGQLRPEKTRFDAFRSIFPAGT
An_Trp2  335 ALAHELKGSQIKDRAEHVMLVDLARNDVNRVCDPITTQVDFLMVVEKFSHVQHLVSQVSGILRPEKTRFDAFRSIFPAGT
Af_Trp2  325 ALAAELRGSLKDRAEHVMLVDLARNDVNRVCDPITTQVDFLMVVEKFSHVQHLVSQVSGILRPQKTRFDAFRSIFPAGT

Nt_Trp2  468 VSGAPKVIAMGLIDQLEVIRGPYSGGFSGISFSG----------DHDIALALRTNVPLNTARYDTMYSYTDASKRQEW
Sc_Trp2  408 VSGAPKVRAMQLIAELEGERGVYAGAVCHWSIDGK-----------TNDICIALRTMVIQGLA
An_Trp2  415 VSGAPKVRAMQLIAELEGERGVYAGAVGYECINIASADGKTENFGAMDTCIALRTMVVNGVA
Af_Trp2  405 VSGAPKVRAMQLIAELEGERGVYAGAVGYECTDSSADGNLIPGAMDTCIALRTMVIRGVA

Nt_Trp2  537 VAHLQSPAGIVADSNPDKQIDCENDVASLCRAITDVAISAFVKGRHKPSVRINGSVPNLFSKVQHQTSGMSRDRIHEKRN
Sc_Trp2  462 --YLQAGGGIVPDSDEYDRYVETINKHMANISTIVQAIELWADIVGSA----------
An_Trp2  479 --YLQAGGGIVFDSDPYDEYVETLNKLGANICIKGADAVYLSDEESRRA----------
Af_Trp2  469 --YLQAGGGIVFDSDPYDEYVETLNKLGANICIKGAEAKYLSNGGL----------
```

| Percent Identity Matrix | | | | |
|---|---|---|---|---|
|  | Nt_Trp2 | Sc_Trp2 | An_Trp2 | Af_Trp2 |
| Nt_Trp2 | 100.0 % | 37.35 % | 38.10 % | 37.50 % |
| Sc_Trp2 | 37.35 % | 100.0 % | 60.71 % | 61.24 % |
| An_Trp2 | 38.10 % | 60.71 % | 100.0 % | 86.55 % |
| Af_Trp2 | 37.50 % | 61.24 % | 86.55 % | 100.0 % |

Fig 12

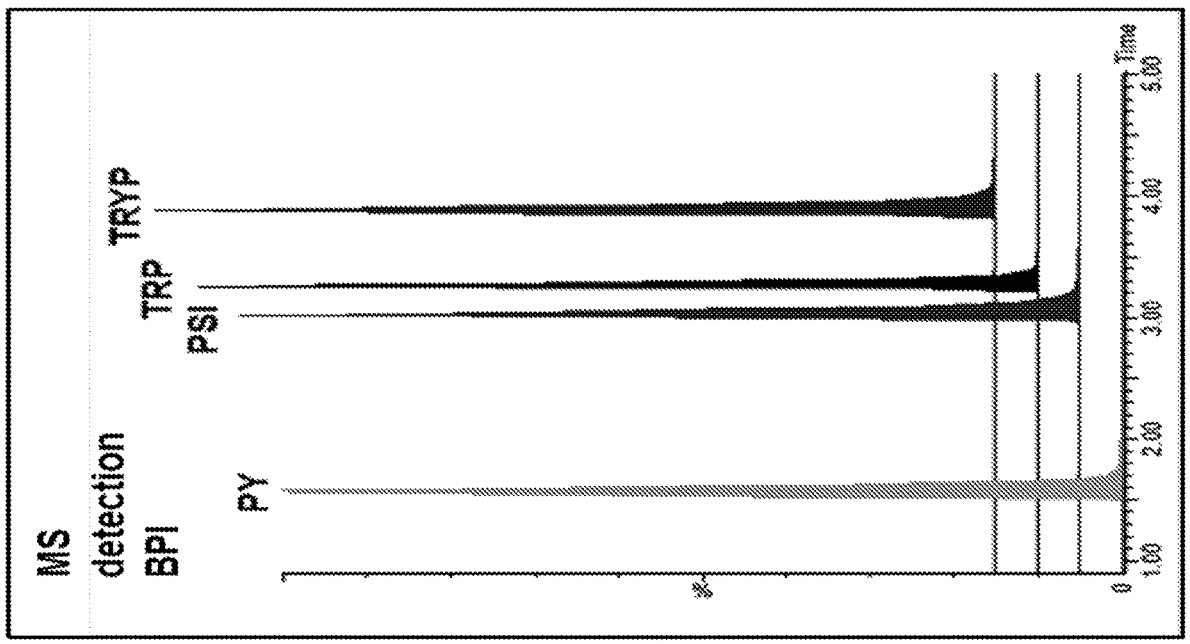
Fig 13C
| COMPOUND LIST | Abbre-viation | Mi (m/z) | m/z | rt [min] |
|---|---|---|---|---|
| Psilocybin | PY | 284.093 | 285.100 | 1.56 |
| Psilocin | PSI | 204.126 | 205.130 | 3.02 |
| Tryptamine | TRYP | 160.100 | 144.080 | 3.88 |
| L-Tryptophan | TRP | 204.09 | 188.07 | 3.26 |
Fig 13A
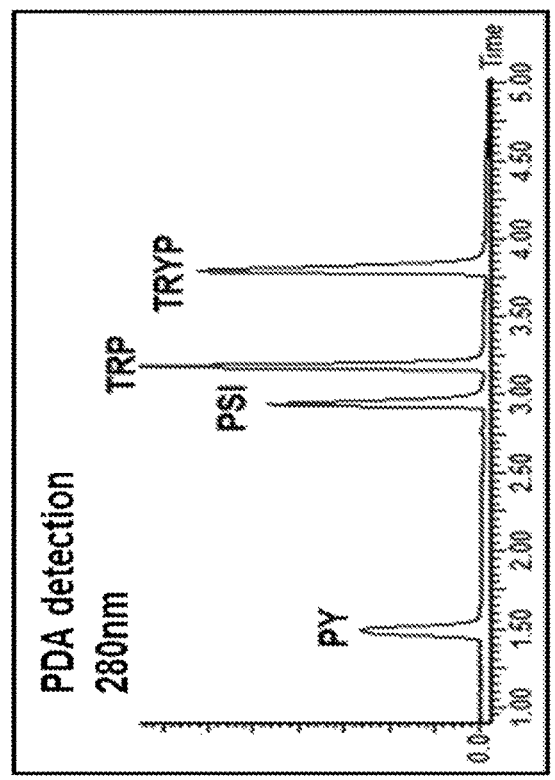
Fig 13B

SEQUENCE LISTING

<160> NUMBER OF SEQ ID NOS: 25

<210> SEQ ID NO 1
<211> LENGTH: 1317
<212> TYPE: DNA
<213> ORGANISM: Psilocybe cubensis

<400> SEQUENCE: 1

```
atgcaagtaa ttccggcctg caacagtgca gctataaggt ccttgtgtcc taccccagag      60
tcctttagaa acatgggatg gttgagcgtt tcagacgcag tgtattccga atttataggc     120
gaattagcaa ccagggcaag caacagaaat tacagcaacg aatttgggtt aatgcaaccc     180
attcaagagt tcaaagcttt tatcgaaagt gaccctgtgg tccatcaaga attcattgac     240
atgttcgaag gcatacaaga ttctcccaga aattatcagg agctatgcaa catgtttaat     300
gatattttca ggaaagctcc ggtctacggg gacctgggcc cccctgtata tatgattatg     360
gcgaagttga tgaacaccag ggctgggttc agtgccttta ctaggcaacg tcttaattta     420
```

```
cacttcaaga agctatttga cacttggggt ttattttaa gttccaaaga tagtcgtaac      480
gtactggtag cggatcaatt cgacgacaga cactgcggtt ggttgaatga aagggcctta      540
agcgcaatgg tgaagcatta taatggcagg gcgtttgacg aagtattctt atgcgataaa      600
aacgctcctt attatggatt taattcctat gacgactttt tcaatagaag gttcagaaac      660
cgtgatattg ataggcccgt ggtgggagga gtgaacaaca caaccctgat tctgccgct       720
tgtgaaagct taagctataa tgtttcttat gatgtacaaa gtttagatac gctggtgttc      780
aagggagaga cttacagcct gaagcactta ctgaataatg atcccttcac cccgcaattt      840
gagcacggga gcattttgca aggattccta acgttactg cttaccacag atggcacgcg       900
ccagtcaatg gcacaatcgt aaaaatcata acgttcccg gaacgtactt tgcgcaagca       960
cccagtacca taggagaccc aatccccgac aatgactatg atccacctcc ctatctaaaa     1020
tccttagtct atttcagtaa catcgctgcg aggcaaataa tgtttataga ggcggataac     1080
aaggagatag ggttgatctt tttggtcttt attggtatga cggagatttc aacatgtgag     1140
gctacagtga gcgagggtca acatgtgaac cgtggggacg acttagggat gtttcatttt     1200
ggcggctcca gtttcgcttt gggattaaga aaagattgta gggccgaaat cgtagaaaaa     1260
tttacggaac cggcacagt catcaggatt aacgaggttg tcgctgcact gaaagct        1317

<210> SEQ ID NO 2
<211> LENGTH: 1317
<212> TYPE: DNA
<213> ORGANISM: Psilocybe cyanescens

<400> SEQUENCE: 2
atgcaggtct tgccagcatg tcaatcaagt gcgttgaaga cccttttgccc atcaccagag      60
gcattcagga agctagggtg gttgcccacc tctgatgagg tgtacaacga gttcatagat      120
gaccttacag gccgtacctg caacgaaaag tactcttcac aagtaaccct gcttaagcca      180
atacaggact tcaagacatt tatcgagaac gatcctatcg tgtatcagga gtttatcagc      240
atgtttgagg gcattgaaca atcacctact aactatcacg aactgtgcaa tatgttcaac      300
gatatcttca ggaaggctcc tttatatggg gatctggggc cgccagttta tatgataatg      360
gctagaataa tgaacactca agcagggttt tccgcgttta ctaaggaatc actaaatttc      420
cacttcaaga aattgtttga tacttggggc ctgttttat cctccaagaa ttctaggaac       480
gtgctggtcg ctgatcaatt cgacgataaa cattatggtt ggttctctga agagcgaag       540
acggcaatga tgataaatta ccccggccgt acctttgaga agtttttcat atgcgacgag      600
catgtcccat accacggatt caccagctat gacgattttt tcaacaggcg ttttcgtgat      660
aaggatactg ataggccggt agtaggaggc gtaaccgata ctaccctaat tggtgcagct      720
tgcgagagtt tgtcatataa cgtgagccac aatgtccaga gcttggacac actggtcatc      780
aagggagaag catacagcct gaaacatttg ttacataacg acccccttcac cccgcagttt     840
gagcacggca gcattattca gggatttctt aatgttacgg cctatcatag gtggcattcc      900
cctgtgaacg ggactatcgt aaaaattgtt aatgtcccag ggacttattt cgcacaagcc      960
ccatatacga tagggtcacc cattcctgat aatgataggg acccaccgcc gtaccttaag     1020
tcccttgttt acttcagtaa tatcgccgca agacaaatta tgtttatcga ggctgacaac     1080
aaagatatcg ggctgatctt ccttgtgttt attgggatga ccgaaatatc aacttgcgaa     1140
gcaaccgtat gcgaaggtca acacgttaat cgtggggacg acttaggtat gtttcacttc     1200
```

| ggggatcttc ctttgcact aggccttaga aaggactcta aggccaagat ccttgagaag | 1260 |
| ttcgcgaagc cgggtacagt gatcagaatc aatgaattag ttgcaagcgt aagaaag | 1317 |

<210> SEQ ID NO 3
<211> LENGTH: 927
<212> TYPE: DNA
<213> ORGANISM: Psilocybe cubensis

<400> SEQUENCE: 3

| atgcatataa ggaatcctta ccgtacacct atcgactacc aagccttgtc agaagccttt | 60 |
| ccaccactta agccttttgt gagtgttaat gcggatggca ccagcagtgt cgatctgacg | 120 |
| atccctgagg cgcagagagc ttttaccgca gctctattac atcgtgactt cgggttaaca | 180 |
| atgactatcc ctgaagacag attatgtcca accgttccca acaggcttaa ttacgtgttg | 240 |
| tggatagaag acatctttaa ctacacgaat aaaaccctgg gattaagcga cgataggccg | 300 |
| attaagggtg tagacattgg gaccggcgct agtgcgattt atcctatgct ggcttgtgct | 360 |
| agatttaaag catggtctat ggttggaacc gaagtggaac gtaagtgtat tgatacggcg | 420 |
| aggttgaacg tagtcgctaa taatttacaa gacaggctgt caatacttga acgagtatc | 480 |
| gacgggccta ttttggtacc catttttgag gcgacagaag agtacgaata cgagttcacg | 540 |
| atgtgcaacc caccccttcta tgacggagct gctgatatgc agacttccga cgcggccaag | 600 |
| ggatttggtt ttggagtagg ggcaccccat tctggcacgg tgattgagat gtctaccgaa | 660 |
| ggcggcgagt cagcgtttgt agcacaaatg gtccgtgaat ctctaaagct gaggaccaga | 720 |
| tgcaggtggt acacgtccaa tttgggcaaa ttaaagtcat taaagagat gtaggattg | 780 |
| ctgaaagaat tggaaatatc aaactatgcc atcaacgaat acgtccaagg tagcacaagg | 840 |
| cgttacgccg tggcttggtc cttcactgac attcaattgc ccgaagaact atcacgtcct | 900 |
| tcaaaccccg aactaagttc acttttc | 927 |

<210> SEQ ID NO 4
<211> LENGTH: 927
<212> TYPE: DNA
<213> ORGANISM: Psilocybe cyanescens

<400> SEQUENCE: 4

| atgcatattc gtaacccata ccgtgatgga gtggattacc aggcgctggc cgaggctttc | 60 |
| cccgcccctta aacctcacgt gacagttaat tccgacaata ctacgtctat tgatttcgcc | 120 |
| gtgcctgagg ctcagcgtct atacacggct gcgctgttac accgtgattt cggtttaacc | 180 |
| attacccttc cggaagatcg tctatgtccc accgtcccaa acagattaaa ctacgttcta | 240 |
| tgggtcgaag acatactaaa ggtcacatcc gatgctctgg gtttaccaga caacagacag | 300 |
| gttaagggaa ttgacatagg gaccggggcc tcagctatct accctatgtt agcctgttcc | 360 |
| aggttcaaaa cctggtcaat ggttgctacg gaggtggacc aaaaatgtat tgatacagcg | 420 |
| cgtctgaacg taattgctaa taaccttcaa gagcgtctag ccataatagc gacgagcgtc | 480 |
| gatggcccca tcctggtccc ccttctacag gctaattccg acttcgaata cgactttact | 540 |
| atgtgcaatc cccattctta tgatgggcg tccgatatgc aaaccagcga tgccgcgaag | 600 |
| ggcttcggat tcggcgtgaa cgcgccccat accggaacag tgttggagat ggcgacggaa | 660 |
| gggggcgaga gtgcattcgt ggcacagatg gttagggaga gtctaaactt gcaaactaga | 720 |
| tgtaggtggt tcacatcaaa cttagggaaa ctaaagagcc tatacgagat agtaggactg | 780 |
| ttgagagaac accaaaatttc caactatgca ataaacgagt atgttcaagg agctacaaga | 840 |

```
cgttacgcaa tcgcatggtc ctttatcgac gttaggttgc cagatcacct ttcaaggcca    900
agtaatccgg atctttcctc tctattc                                        927

<210> SEQ ID NO 5
<211> LENGTH: 1524
<212> TYPE: DNA
<213> ORGANISM: Psilocybe cubensis

<400> SEQUENCE: 5
atgatcgccg tattattttc tttcgtgatc gctggttgta tatactacat tgtgtctcgt     60
agagtgagac gttctaggct gccgccggga cctcctggca taccaatacc ttttattggt    120
aacatgtttg acatgcctga agagtcccca tggctaactt tcctacagtg gggcagggac    180
tataatacgg acatacttta cgtggacgcg ggaggcacgg agatggtcat actaaacacc    240
ttggaaacaa tcacagactt actggaaaaa cgtggcagca tttactccgg tcgtttggag    300
agcacaatgg taaacgaact tatgggatgg gagtttgatc tggggtttat cacttatggc    360
gatcgttgga gggaggagcg taggatgttc gctaaagaat ttagcgagaa gggcatcaaa    420
caattcaggc acgcacaggt aaaagcagca caccaacttg tccaacaact tacgaagact    480
cctgacagat gggctcaaca catccgtcat cagattgctg ctatgtcctt ggatattggt    540
tatgggattg acttagctga ggatgatccc tggctgaag cgacccatct tgcgaacgaa     600
gggcttgcta ttgcctccgt tcctgggaag ttctgggtag atagcttccc ctcactaaaa    660
tatcttccgg cttggttccc aggtgccgtc ttcaaaagga aggcaaaggt atggagagag    720
gctgcagatc acatggtcga tatgccgtac gaaacaatga ggaagttggc cccgcaaggg    780
ttaacgcgtc ccagttacgc aagtgctagg ttgcaggcta tggatttgaa tggagacctt    840
gaacaccaag agcacgtcat caagaataca gcggcggagg tcaatgttgg cggcggggac    900
actaccgtat ccgcgatgtc agcgtttatc cttgcaatgg tcaaataccc cgaggtgcaa    960
agaaaagtac aggccgaact ggacgcactg acaaacaacg gccagatccc agactatgat   1020
gaagaggatg atagtctacc ttatctgacc gcctgcatca agagctatt ccgttggaat    1080 cagatagccc ccctagcgat accgcacaag ctgatgaagg acgatgttta tagggggttat   1140 ctgatacccca gaataccct ggttttcgct aacacatggg ccgtcctaaa tgacccggag    1200
gtgtacccgg accccagcgt ttttagaccc gaaaggtacc ttggccctga tgggaaaccg   1260
gataatactg tccgtgaccc gagaaaagcc gcgtttggct atggaaggcg taattgccca   1320
ggaatacatc tggcgcagag tactgtttgg atagcaggtg cgacgctatt atccgccttt   1380
aatattgaga ggccggttga ccaaaacggt aagcccatcg atatacctgc agatttcact   1440
acggggttct ttagacatcc agtacccttc cagtgtcgtt tcgttccacg taccgaacag   1500
gtatcccagt ctgtcagcgg accg                                          1524

<210> SEQ ID NO 6
<211> LENGTH: 1521
<212> TYPE: DNA
<213> ORGANISM: Psilocybe cyanescens

<400> SEQUENCE: 6
atgatagtcc tgttggtgag tttagtttta gccggctgca tatactacgc aaatgcacgt     60
cgtgttaggc gtagcagact tccacccgga cccctggca tcccactgcc ctttattggc    120
aacatgtttg atatgccaag cgaatctcct tggcttcgtt tccttcaatg gggccgtgat    180
```

| | |
|---|---|
| tatcacacgg acatcttata tttgaatgcc ggtggaacgg agatcatcat cttaaatacg | 240 |
| ttagacgcta ttacggacct actggaaaag cgtgggtcaa tgtactctgg gaggctagaa | 300 |
| agcaccatgg tcaatgaact tatgggctgg gagttcgact tgggctttat aacctatggg | 360 |
| gagaggtgga gggaggaaag acgtatgttc gctaaagagt tcagcgagaa gaacatccgt | 420 |
| caatttagac atgctcaaat taaagcagct aaccaactag taaggcagct tataaaaact | 480 |
| ccagacagat ggtcccagca tatcagacat cagatcgccg caatgagttt agacataggg | 540 |
| tacgggattg acttggccga ggatgatcct tggatagcag cgacccaact ggctaacgaa | 600 |
| gggttagctg aagccagcgt gccagggagt ttttgggttg attcatttcc cgcacttaag | 660 |
| tacctgccca gttggttgcc tggggcggga ttcaagcgta aggcgaaggt gtggaaagaa | 720 |
| ggggccgatc acatggtgaa tatgccctat gagaccatga aaagttgac agtccaagga | 780 |
| cttgctaggc ctagctatgc atctgcaagg ttacaggcta tggaccctga cggtgactta | 840 |
| gagcatcaag aacacgttat acgtaatacg gctaccgagg tgaatgtggg tgggggcgac | 900 |
| accactgtat ctgcagtttc cgcgttcatt ttagcaatgg tgaaatatcc ggaagtacag | 960 |
| cgtcaggtgc aggcagagct tgatgcttta actagcaagg gggtagtgcc caattatgac | 1020 |
| gaggaggacg atagtctgcc gtatttaact gcgtgtgtta aggagatttt tagatggaac | 1080 |
| caaatagcgc ccttagcaat accgcatagg cttatcaaag acgatgttta ccgtgggtat | 1140 |
| ctgataccga aaaatgcgct tgtttacgcc aacagttggg cagtcttgaa cgatccggaa | 1200 |
| gaatatccga acccttcaga atttagaccg gaaaggtatt taagtagtga cgggaaacct | 1260 |
| gaccccacgg tacgtgaccc aaggaaggct gcattcgggt acggtcgtag gaattgccca | 1320 |
| gggatacact ggctcagag tactgtatgg atagctggcg caaccctgtt gtcagtgttt | 1380 |
| aacatagaga gacccgtaga cggaaatggg aaacctattg atataccggc gacgtttact | 1440 |
| acaggtttct tcaggcatcc agaaccattt cagtgtagat ttgttcctag aacccaggag | 1500 |
| attttaaaga gtgtatctgg g | 1521 |

<210> SEQ ID NO 7
<211> LENGTH: 1086
<212> TYPE: DNA
<213> ORGANISM: Psilocybe cubensis

<400> SEQUENCE: 7

| | |
|---|---|
| atggcgtttg atcttaagac tgaggatggc ctaattacgt atttgactaa gcatttgagc | 60 |
| ttagatgtgg acacatcagg cgttaagaga ctgtctgggg gattcgtaaa tgtcacctgg | 120 |
| cgtataaagt tgaacgctcc gtatcaggga catactagca ttatacttaa gcacgctcaa | 180 |
| ccgcacatga gcaccgatga agattttaaa ataggtgtcg aaagaagcgt atacgagtat | 240 |
| caagcaataa aactgatgat ggccaataga gaggtattag gtggggtgga tgggatagtc | 300 |
| agcgtaccgg aagggttaaa ctacgattta gaaaataatg cgctgataat gcaggatgtg | 360 |
| ggtaagatga agaccttgct tgattacgtt accgcgaaac ctcctcttgc cacagatata | 420 |
| gcacgtctag taggaacaga aataggtgga ttcgtagcga ggttacataa tatcggcagg | 480 |
| gagagacgtg atgacccaga atttaagttt ttctctggca acatagtcgg taggaccaca | 540 |
| agtgatcaat ataccaaac tataattcca aatgccgcca gtacggtgt ggatgaccca | 600 |
| ttacttccga cggtcgtaaa ggatttggtg gatgacgtca tgcactcaga agagacccctt | 660 |
| gttatggcag acctgtggtc cgggaacata ctacttcagc tagaggaggg caatccgtct | 720 |
| aaactgcaga aaatctatat attagactgg gagttgtgca aatacgggcc tgcatcttta | 780 |

```
gatttgggct actttctagg tgactgttat cttatcagta ggttccaaga cgaacaggtc      840
gggactacta tgaggcaagc ctaccttcag agttatgcta ggacgtctaa acacagcatt      900
aattacgcga aggtgactgc aggaatagca gctcatatcg taatgtggac ggactttatg      960
cagtggggta gtgaagagga gagaataaac tttgtgaaaa aggtgttgc agccttttcat     1020 gacgctagag gaaacaatga caatggtgag attaccagca cgttactaaa ggaatcatcc     1080
acagct                                                                1086

<210> SEQ ID NO 8
<211> LENGTH: 1083
<212> TYPE: DNA
<213> ORGANISM: Psilocybe cyanescens

<400> SEQUENCE: 8
atgacatttg atttgaaaac ggaagaaggg ttattaagtt atttaacaaa gcacttaagc       60
cttgatgtag ctccgaatgg ggtaaaacgt ctatcaggag gttttgtcaa cgtgacctgg      120
agagttggac taaacgcacc atatcacgga catacttcaa tcattctaaa gcatgcacag      180
ccccatttat cctcagacat cgactttaag atcggggtgg aacgtagtgc ttatgaatat      240
caagccctta agatagtctc tgccaactcc agtttgctag ggagtagcga catcagagta      300
agtgtcccgg aaggcttaca ttatgatgta gtcaacaacg cgctaatcat gcaggacgtg      360
ggcacaatga agactctatt ggattatgtt acggctaagc cgccgatcag cgcagaaatt      420
gcgtctctag ttggtagcca ataggagcg tttattgcga gactgcataa tttaggtaga      480
gaaaataagg acaaggatga ctttaaattt ttctctggca acatcgtagg gcgtacaact      540
gcagaccagc tataccaaac aatcatccct aacgccgcaa agtatggcat tgacgatccg      600
attttgccca tcgtggttaa ggaattagtc gaggaggtga tgaactccga ggaaactcta      660
atcatggcag acctgtggag tggcaatatt ttattacagt tcgacgaaaa tagtaccgag      720
cttactagga tatggctggt agattgggag ttgtgtaaat acggtcctcc cagcttggat      780
atgggttact ttctgggaga ttgtttctta gtagcgaggt ttcaggacca gctggtaggt      840
acgtcaatgc gtcaagcata cctgaaaagt tacgctagga atgtaaagga acctataaac      900
tacgcaaaag cgactgctgg cattggggct cacctggtta tgtggacgga cttttatgaag     960 tggggtaacg atgaggaaag agaagagttt gtgaaaaaag gggtcgaagc gttccacgaa     1020
gcgaacgagg ataaccgtaa cggcgaaata actagcatac tggttaagga agcttcaagg     1080
acg                                                                   1083

<210> SEQ ID NO 9
<211> LENGTH: 1317
<212> TYPE: DNA
<213> ORGANISM: Psilocybe cubensis

<400> SEQUENCE: 9
atgcaggtca ttccagcctg taattccgca gccatccgta gtctgtgccc tacgccggag       60
tcctttagaa acatggggttg gctttcggtt tcagacgctg tatactcgga atttatcggc      120
gaattggcga cccgtgcgtc gaatcgaaac tatagcaacg aattcggact gatgcagccg      180
atccaagaat tcaaagcttt cattgaatca gatccagtag ttcaccagga atttattgac      240
atgtttgagg gaatacagga ctcgccgcga aactatcaag aactttgcaa tatgttcaac      300
gacatcttca ggaaagcgcc tgtttacggg gacttgggtc ctccggtgta catgattatg      360
```

| | |
|---|---|
| gcaaagctta tgaacactcg cgctggattc agtgctttca caagacaacg actgaatctc | 420 |
| cacttcaaga aacttttga cacctgggga cttttcctct cctcgaagga tagccgtaac | 480 |
| gttctcgtcg ccgaccagtt cgacgacaga cattgtggat ggctgaacga gagggccttg | 540 |
| tcggcgatgg tcaagcatta aacgggcga gcattcgatg aagtgttct ttgcgacaaa | 600 |
| aatgcgccgt actatggctt taattcatac gatgatttct ttaatagaag attcaggaac | 660 |
| cgcgacatag atcgccctgt agtaggggggt gttaacaaca caacgttgat ctccgctgcc | 720 |
| tgtgagtcgt tgtcgtacaa cgtgagttat gatgtacagt cgctggacac cttggtcttc | 780 |
| aagggagaaa cttatagtct caagcatctt ctgaataatg acccttttac cccccaattt | 840 |
| gagcacggca gcattcttca aggattcctc aatgttacgg cctatcaccg ttggcacgca | 900 |
| cccgtcaatg ggaccattgt caaaatcatt aatgtacccg gaacctattt tgcacaagca | 960 |
| ccatcaacca taggtgaccc gattccagat aacgactatg accctccccc atacctcaag | 1020 |
| agtctggtgt atttctcgaa tattgccgcc cgacaaatta tgtttattga agcggacaac | 1080 |
| aaagagatag ggctcatctt cctcgtcttc ataggaatga cagaaattag cacttgcgaa | 1140 |
| gccactgttt cagaaggaca gcacgtcaat cgcggcgacg acctgggtat gttccatttc | 1200 |
| ggtggatcca gtttcgcgct ggggcttcgc aaggactgca gagctgagat agtcgagaaa | 1260 |
| tttacggaac ctggcacggt aattcggatt aatgaagtag tcgctgcact caaagct | 1317 |

<210> SEQ ID NO 10
<211> LENGTH: 1317
<212> TYPE: DNA
<213> ORGANISM: Psilocybe cyanescens

<400> SEQUENCE: 10

| | |
|---|---|
| atgcaagtct tgcccgcatg tcaaagcagc gcactgaaga ccctctgtcc tagcccagag | 60 |
| gcatttcgca aactcggttg gcttcccacc agtgacgagg tgtacaacga gtttattgat | 120 |
| gacctcactg gaaggacttg taatgaaaaa tactcaagtc aggtcacgct gctcaaaccg | 180 |
| attcaagact tcaagacctt catagagaat gacccgattg tttatcaaga gttcatatcg | 240 |
| atgttcgagg gtattgagca atcccctact aactatcacg aattgtgtaa catgttcaat | 300 |
| gatattttc ggaaggcgcc cctgtacgga gatctcggtc caccagtgta tatgattatg | 360 |
| gcacggataa tgaatacaca ggcagggttt agcgccttta cgaaggagtc gcttaacttt | 420 |
| catttcaaaa aacttttga cacttggggt ctcttttga gcagcaaaaa ttcccgaaac | 480 |
| gtgttggttg cagatcagtt cgatgataaa cattatgggt ggttcagcga acgcgcgaaa | 540 |
| accgccatga tgattaacta tccgggacga actttcgaga aagtcttcat atgcgatgaa | 600 |
| catgtcccat atcatggatt tacatcctat gatgacttct ttaaccgtcg cttcagggac | 660 |
| aaagacacgg accgccctgt ggtcgggggg gttactgaca ccaccctcat cggcgcggcc | 720 |
| tgcgaatcgt tgtcttataa cgtgtctcat aacgttcagt cgcttgacac ccttgtgatc | 780 |
| aaggggaag cctacagtct gaagcatctg ctccacaacg acccgtttac cccccaattt | 840 |
| gagcatggat ccattataca ggggttcctc aatgtgacag catatcacag gtggcactct | 900 |
| cccgtcaacg gcacaatcgt taagatcgtc aatgtccctg gaacctactt cgcgcaagca | 960 |
| ccgtacacga taggtagtcc tattcccgat aatgacaggg atcctccacc ttacttgaag | 1020 |
| tctttggtat acttcagtaa tatagctgct cggcagataa tgtttataga ggcggacaat | 1080 |
| aaagacattg gctgatatt cctggtgttc ataggggatga ccgagatctc tacatgcgag | 1140 |
| gcgacagtct gtgaaggaca gcacgtgaat cgaggagacg acttgggtat gttcatttt | 1200 |

```
ggaggatcgt ccttcgctct tggactgcga aaggactcga aggcaaagat attggagaaa    1260
tttgcgaaac caggaactgt cattcgtata atgagcttg ttgcgtctgt acgcaag       1317

<210> SEQ ID NO 11
<211> LENGTH: 927
<212> TYPE: DNA
<213> ORGANISM: Psilocybe cubensis

<400> SEQUENCE: 11
atgcatattc gtaatccgta cagaaccccc atcgactacc aggccctctc cgaagcattt     60
ccccccctta agccctttgt ctctgtaaac gcggacggaa catcctcagt agacctgaca    120
attccggagg cgcaaagggc gtttacagca gctcttttgc atcgcgactt tggcctcacg    180
atgacgatac cagaggatcg cttgtgccct accgtgccca ataggctgaa ttatgttctg    240
tggattgaag atatcttcaa ctatacaaac aaaacactgg gactcagtga cgatagaccg    300
ataaagggtg tggatatagg aacgggggca tccgcgattt atccaatgct tgcgtgtgcc    360
aggttcaaag cgtggtcgat ggttgggacc gaagtggagc gcaaatgtat cgacacagcc    420
cgtctgaatg tcgtcgccaa caatcttcag gacaggttgt caatactgga gactagtata    480
gacgggccaa tacttgtacc aattttcgag gcgactgagg aatatgagta tgaatttact    540
atgtgcaatc cacccttta tgatggtgcc gctgacatgc aaacctctga tgccgctaag    600
ggctttggtt ttggcgtggg agcgccccac agtggaacag tgattgaaat gtccacagaa    660
gggggagagt ccgcattcgt agcacagatg gtccgtgaat cgctcaaact cgcacgaga    720 tgcaggtggt atacctcaaa tctcggtaaa ctgaagtctc tgaaggaaat tgtgggcttg    780
ttgaaggagt tggagatttc caactacgca ataaacgagt atgttcaggg ttccacgagg    840
cgttatgccg tagcctggtc cttcaccgac atccagcttc cgaggagtt gtcgagaccg    900 tcaaatccag aactctccag tctgttc                                       927

<210> SEQ ID NO 12
<211> LENGTH: 927
<212> TYPE: DNA
<213> ORGANISM: Psilocybe cyaescens

<400> SEQUENCE: 12
atgcatataa ggaacccta tcgggatggg gtcgattacc aagcactggc ggaggcgttt     60
ccggcgctta aacctcacgt aactgttaat agtgacaata caacctcgat agatttcgca    120
gtcccagaag cacagcggct ttatactgct gccctgctgc acagggattt tggtttgaca    180
atcaccttgc cagaagaccg actgtgtcca acagtgccca acagattgaa ctacgtcctc    240
tgggtggaag atattttgaa ggtgacgagt gacgctcttg gtttgccaga taatcgacaa    300
gttaagggca ttgacattgg taccggagct tccgcaatct atcccatgct ggcttgctct    360
cggttcaaaa catggtctat ggttgcaacg gaggtcgacc agaagtgcat cgatactgcc    420
cggctcaatg tgatagccaa caacctgcaa gaaaggttgg ctattattgc aacaagcgtg    480
gacggaccta cttgtacc ccttctccaa gcaaatagtg atttcgagta tgatttact    540 atgtgcaacc caccttcta tgatgggcc tctgacatgc agacttcgga cgcggcaaag    600 ggttcggct tcggcgtaaa tgctccccac acgggtacgg tactggagat ggctacggaa    660
ggtggagaat ccgcatttgt tgcgcaaatg tgagagaat cgctgaatct gcaaacgcgg    720
tgccggtggt ttaccagtaa tctggggaaa ctcaagtccc tttatgagat tgtcgggctc    780
```

```
ctgagggagc atcaaatctc aaactatgca atcaatgaat atgtccaggg tgctacgcga      840
cggtacgcca tcgcttggtc gtttatagat gtgcggcttc cggaccacct ttcaagaccc      900
agcaatccgg atctttcgtc attgttc                                          927
```

```
<210> SEQ ID NO 13
<211> LENGTH: 1524
<212> TYPE: DNA
<213> ORGANISM: Psilocybe cubensis

<400> SEQUENCE: 13
atgatagctg tcctgttctc ctttgttata gctggttgca tatattacat cgtgtcccgt       60
cgtgttcgtc gatcacggct ccctccaggg cccctggta tcccgatacc ttttattggt      120
aacatgtttg acatgcccga agaaagtcct tggctcacat tcttcaatg ggggcgtgat      180 tacaatacgg acatacttta cgttgatgcg ggggaaccg aaatggtcat acttaataca      240
ttggagacta ttaccgatct tttggagaaa cgaggaagca tctactcggg acgccttgaa      300
tccacgatgg tcaacgagct catgggttgg gaatttgatt tgggatttat cacctatgga      360
gatcggtggc gtgaggagcg taggatgttt gcaaaagaat tttcagaaaa gggtatcaaa      420
cagtttcgtc atgcgcaagt taaagcagct caccagctgg tccaacaatt gactaaaacc      480
ccagatcgtt gggcgcaaca tatcaggcat caaatcgccg caatgtccct tgatattggt      540
tatgggatcg atctggctga ggacgatcca tggcttgagg cgacccattt ggcaaatgaa      600
ggtctggcaa tcgcgagcgt cccgggaaaa ttttgggtcg actcttttcc aagcctgaaa      660
tatcttccag cctggtttcc gggtgcagtt ttcaagcgaa aagccaaggt gtggcgggag      720
gccgcagatc acatggtcga catgccttac gaaactatgc ggaagctggc accgcaaggg      780
ttgacgcgcc ccagctacgc atcggctcgg ttgcaagcga tggatcttaa tggagacctc      840
gagcatcaag aacatgtcat aaagaacaca gcagcggagg tgaacgtcgg aggggcgac      900 actaccgtgt ccgctatgtc tgcttttatt ctggcgatgg ttaaatatcc cgaggttcag      960
cgaaaggtgc aagcagaact ggacgcactc accaacaacg ggcaaatacc tgactacgat     1020
gaagaagacg atagcttgcc ctatctgaca gcctgcatca aagagctctt tcgatggaat     1080
caaatagcac cgctggctat tccacataag ttgatgaagg atgacgtcta tagggggttat     1140 cttattccca gaacacgct tgtgtttgca aacacatggg cggtgttgaa tgaccccgaa     1200
gtctaccccg atccaagtgt ctttcgtccc gagagatact tgggaccgga cggtaaaccg     1260
gacaacaccg tgcgcgaccc ccgtaaagcg gcctttgggt atgggcgacg gaattgcccc     1320
gggatacatc tggcccagtc gacagtctgg atcgcaggtg caactttgct cagtgctttt     1380
aatatagagc gtcccgttga ccaaaatggc aagccaatcg atataccggc tgacttcaca     1440
actggattct ttaggcatcc ggtgcctttc caatgccgat tcgtgccacg aacagagcaa     1500
gtgagtcaat ccgttagcgg tccg                                           1524
```

```
<210> SEQ ID NO 14
<211> LENGTH: 1521
<212> TYPE: DNA
<213> ORGANISM: Psilocybe cyanescens

<400> SEQUENCE: 14
atgatagttc tccttgtttc tttggtactt gctggatgca tttactatgc caatgcgaga       60
agagtccgcc gtagtaggct ccctccaggc ccaccgggta ttccactccc ttttatcggg      120
aatatgtttg acatgccgtc agagagcccg tggctgcgct tcctccagtg gggccgcgac      180
```

| | | |
|---|---|---|
| tatcacacag acatattgta cctgaatgcc ggtggcacag agatcataat cttgaacact | 240 | |
| ctcgacgcga tcactgactt gcttgagaag cgtggttcga tgtactcggg tcgcttggaa | 300 | |
| tctactatgg tcaacgagct tatgggctgg gagttcgatt tgggatttat cacttatggt | 360 | |
| gagcggtggc gtgaagagcg acggatgttt gcaaaggaat tctccgaaaa gaatatcagg | 420 | |
| caatttagac acgcccagat taaagcagcc aaccagttgg tgagacagct catcaaaacc | 480 | |
| ccagacagat ggtcgcagca catacgacat caaatcgccg caatgagcct ggacatcggt | 540 | |
| tatggaatag acctcgcaga agacgaccca tggatcgctg cgacccagct tgctaatgaa | 600 | |
| ggcttggctg aagctagcgt accaggatcg ttttgggtag attcgttccc agcgctgaag | 660 | |
| tatttgccct cgtggttgcc aggtgcagga ttcaagcgga aggccaaagt gtggaagaa | 720 | |
| ggagcagacc atatggtgaa catgccttat gagaccatga agaagttgac tgttcaaggg | 780 | |
| ctcgcacggc ccagctatgc ctcggcgcga cttcaagcta tggatcccga cggcgatctt | 840 | |
| gagcatcaag aacacgtcat cagaaataca gctacagagg ttaatgtcgg tgggggagac | 900 | |
| accacagtca gtgcggtcag tgcattcatc ctcgctatgg ttaaatacccc ggaagttcag | 960 | |
| cgtcaggttc aggccgagtt ggacgcactg acatcgaaag gagttgttcc gaattatgat | 1020 | |
| gaggaagacg actcgctccc ctatctcact gcttgtgtga aggagatatt caggtggaat | 1080 | |
| caaatcgcgc cattggctat accacaccgc cttataaaag atgatgtata caggggggtat | 1140 | |
| ctcatcccga agaatgccct cgtctacgcg aactcgtggg ccgttcttaa tgatcccgag | 1200 | |
| gaatacccga acccttcaga attccggcct gagcggtacc tctcttcgga cggtaaacct | 1260 | |
| gatcctacag tgcgagatcc gagaaaagcc gccttcggat atggcagacg taattgtccc | 1320 | |
| ggtatccatc ttgctcagtc taccgtttgg atcgctggcg caacgctcct tagcgtgttc | 1380 | |
| aacatagagc ggcctgtaga tggaaatgga agcccattg acatcccgc aacatttact | 1440 | |
| acaggtttct tcaggcatcc tgaaccattc caatgccgct ttgtacctcg aacacaggag | 1500 | |
| atacttaaga gtgtctccgg g | 1521 | |

<210> SEQ ID NO 15
<211> LENGTH: 1086
<212> TYPE: DNA
<213> ORGANISM: Psilocybe cubensis

<400> SEQUENCE: 15

| | | |
|---|---|---|
| atggccttcg acctcaaaac agaggatggg ctcatcacgt acctgaccaa gcatctctct | 60 | |
| ctggacgtag acacgagtgg cgtaaagagg ttgagcgggg gtttcgtaaa tgtgacgtgg | 120 | |
| cgtatcaaat tgaacgcgcc ttaccaggga catacgtcaa tcatccttaa gcacgcccag | 180 | |
| cctcatatgt ccactgacga ggatttcaag atcggcgtcg aaaggagcgt ttacgaatac | 240 | |
| caggcgataa aactcatgat ggcgaaccgt gaagttctcg ggggagtaga cgggatcgtg | 300 | |
| tcggtccctg aaggtcttaa ttatgatctt gagaacaatg ccttgataat gcaagatgtg | 360 | |
| ggtaagatga aaacgttgct tgattacgtc actgcgaaac cccctctggc taccgatatc | 420 | |
| gccaggttgg ttggcactga atcggcgggg tttgtggcaa ggctccacaa cataggaagg | 480 | |
| gaacgtcgag atgatcccga gttcaaattc ttctcgggta tatcgtggg acggacaaca | 540 | |
| tcggaccagc tctaccagac tatcatcccc aacgcagcaa agtacggagt ggatgatcca | 600 | |
| ctgttgccta cagttgtgaa agaccttgtt gacgacgtca tgcacagtga ggagaccctc | 660 | |
| gtaatggctg acctctggtc cggcaacatt ctcctgcaat tggaggaggg taatccgtca | 720 | |

```
aagttgcaga agatttacat tctggattgg gagctttgca agtacggccc tgcgtcgctt      780
gatcttggct actttctcgg cgactgttac ctgatatcac gtttccagga cgaacaggta      840
ggtacgacca tgcgccaggc ctatttgcaa tcatatgcga gaacaagcaa gcatagtatt      900
aactatgcta aagtcacagc tgggatagcg gctcacatag ttatgtggac ggatttcatg      960
cagtggggct ccgaggaaga aaggataaat tttgtaaaaa aaggagttgc tgcctttcac     1020
gacgctagag ggaataacga caacggtgag attacctcaa cactgcttaa agagtcgtcc     1080
acggct                                                                1086

<210> SEQ ID NO 16
<211> LENGTH: 1083
<212> TYPE: DNA
<213> ORGANISM: Psilocybe cyanescens

<400> SEQUENCE: 16
atgacattcg atctgaagac ggaagagggg cttttgtcct acctcacaaa acatctctcc       60
cttgatgtag ctccgaacgg ggttaaacgg ctgtcgggcg gctttgtaaa tgttacctgg      120
cgtgttggac ttaacgctcc ctatcatggg catacgtcta tcatacttaa acatgcacag      180
ccgcaccttt catctgatat tgactttaag attggcgtag aaagaagcgc atacgagtac      240
caagctttga aaattgtgag cgccaacagt agcctcctcg ggtcatccga catacgtgtt      300
tccgtcccag aaggtttgca ttacgatgtg gtgaataacg cactgatcat gcaggatgtc      360
ggcaccatga aaacgctgct cgattacgtt actgcgaaac cgcccataag cgcggaaata      420
gcttcacttg taggatcaca aattggagca tttatagctc ggttgcataa tctggggagg      480
gagaataagg acaaggacga ctttaagttt ttttcgggta acattgtggg tcgaacgacc      540
gcagaccaat tgtatcaaac tattatcccc aatgcggcca aatatggaat tgacgacccc      600
atactcccaa tagttgtaaa ggagttggtc gaggaggtga tgaactcaga ggaaacgctg      660
atcatggcag atttgtggtc gggaaatatc cttttgcaat ttgatgaaaa ttcgacggag      720
ctgaccagaa tatggttggt ggattgggaa ctctgtaagt atgggcctcc ttcactggac      780
atgggatatt tcctcgggga ctgttttctt gtcgcgaggt ttcaagatca acttgtgggg      840
acatctatga ggcaggctta cctcaagagt tacgcgcgga acgtaaaaga gcctataaat      900
tacgcgaaag caacgctgg aatcggagca catctggtga tgtggacgga ctttatgaaa      960
tggggtaatg acgaagagcg agaagagttc gtaaagaagg gagttgaagc gttccacgaa     1020
gcaaacgagg ataacagaaa tggagagata accagtatac ttgttaaaga ggcgagccgt     1080
acg                                                                  1083

<210> SEQ ID NO 17
<211> LENGTH: 370
<212> TYPE: PRT
<213> ORGANISM: Saccharomyces cerevisiae

<400> SEQUENCE: 17

Met Ser Glu Ser Pro Met Phe Ala Ala Asn Gly Met Pro Lys Val Asn
1               5                   10                  15

Gln Gly Ala Glu Glu Asp Val Arg Ile Leu Gly Tyr Asp Pro Leu Ala
            20                  25                  30

Ser Pro Ala Leu Leu Gln Val Gln Ile Pro Ala Thr Pro Thr Ser Leu
        35                  40                  45

Glu Thr Ala Lys Arg Gly Arg Arg Glu Ala Ile Asp Ile Ile Thr Gly
    50                  55                  60
```

```
Lys Asp Asp Arg Val Leu Val Ile Val Gly Pro Cys Ser Ile His Asp
 65                  70                  75                  80

Leu Glu Ala Ala Gln Glu Tyr Ala Leu Arg Leu Lys Lys Leu Ser Asp
                 85                  90                  95

Glu Leu Lys Gly Asp Leu Ser Ile Ile Met Arg Ala Tyr Leu Glu Lys
            100                 105                 110

Pro Arg Thr Thr Val Gly Trp Lys Gly Leu Ile Asn Asp Pro Asp Val
        115                 120                 125

Asn Asn Thr Phe Asn Ile Asn Lys Gly Leu Gln Ser Ala Arg Gln Leu
    130                 135                 140

Phe Val Asn Leu Thr Asn Ile Gly Leu Pro Ile Gly Ser Glu Met Leu
145                 150                 155                 160

Asp Thr Ile Ser Pro Gln Tyr Leu Ala Asp Leu Val Ser Phe Gly Ala
                165                 170                 175

Ile Gly Ala Arg Thr Thr Glu Ser Gln Leu His Arg Glu Leu Ala Ser
            180                 185                 190

Gly Leu Ser Phe Pro Val Gly Phe Lys Asn Gly Thr Asp Gly Thr Leu
        195                 200                 205

Asn Val Ala Val Asp Ala Cys Gln Ala Ala Ala His Ser His His Phe
    210                 215                 220

Met Gly Val Thr Leu His Gly Val Ala Ala Ile Thr Thr Lys Gly
225                 230                 235                 240

Asn Glu His Cys Phe Val Ile Leu Arg Gly Gly Lys Lys Gly Thr Asn
                245                 250                 255

Tyr Asp Ala Lys Ser Val Ala Glu Ala Lys Ala Gln Leu Pro Ala Gly
            260                 265                 270

Ser Asn Gly Leu Met Ile Asp Tyr Ser His Gly Asn Ser Asn Lys Asp
        275                 280                 285

Phe Arg Asn Gln Pro Lys Val Asn Asp Val Val Cys Glu Gln Ile Ala
    290                 295                 300

Asn Gly Glu Asn Ala Ile Thr Gly Val Met Ile Glu Ser Asn Ile Asn
305                 310                 315                 320

Glu Gly Asn Gln Gly Ile Pro Ala Glu Gly Lys Ala Gly Leu Lys Tyr
                325                 330                 335

Gly Val Ser Ile Thr Asp Ala Cys Ile Gly Trp Glu Thr Thr Glu Asp
            340                 345                 350

Val Leu Arg Lys Leu Ala Ala Ala Val Arg Gln Arg Arg Glu Val Asn
        355                 360                 365

Lys Lys
    370

<210> SEQ ID NO 18
<211> LENGTH: 507
<212> TYPE: PRT
<213> ORGANISM: Saccharamyces cerevisiae

<400> SEQUENCE: 18

Met Thr Ala Ser Ile Lys Ile Gln Pro Asp Ile Asp Ser Leu Lys Gln
1               5                   10                  15

Leu Gln Gln Gln Asn Asp Asp Ser Ser Ile Asn Met Tyr Pro Val Tyr
                20                  25                  30

Ala Tyr Leu Pro Ser Leu Asp Leu Thr Pro His Val Ala Tyr Leu Lys
            35                  40                  45

Leu Ala Gln Leu Asn Asn Pro Asp Arg Lys Glu Ser Phe Leu Leu Glu
```

```
            50                  55                  60
Ser Ala Lys Thr Asn Asn Glu Leu Asp Arg Tyr Leu Phe Ile Gly Ile
 65                  70                  75                  80

Ser Pro Arg Lys Thr Ile Lys Thr Gly Pro Thr Glu Gly Ile Glu Thr
                     85                  90                  95

Asp Pro Leu Glu Ile Leu Glu Lys Glu Met Ser Thr Phe Lys Val Ala
                    100                 105                 110

Glu Asn Val Pro Gly Leu Pro Lys Leu Ser Gly Gly Ala Ile Gly Tyr
                    115                 120                 125

Ile Ser Tyr Asp Cys Val Arg Tyr Phe Glu Pro Lys Thr Arg Arg Pro
                130                 135                 140

Leu Lys Asp Val Leu Arg Leu Pro Glu Ala Tyr Leu Met Leu Cys Asp
145                 150                 155                 160

Thr Ile Ile Ala Phe Asp Asn Val Phe Gln Arg Phe Gln Ile Ile His
                    165                 170                 175

Asn Ile Asn Thr Asn Glu Thr Ser Leu Glu Glu Gly Tyr Gln Ala Ala
                    180                 185                 190

Ala Gln Ile Ile Thr Asp Ile Val Ser Lys Leu Thr Asp Asp Ser Ser
                195                 200                 205

Pro Ile Pro Tyr Pro Glu Gln Pro Pro Ile Lys Leu Asn Gln Thr Phe
                210                 215                 220

Glu Ser Asn Val Gly Lys Glu Gly Tyr Glu Asn His Val Ser Thr Leu
225                 230                 235                 240

Lys Lys His Ile Lys Lys Gly Asp Ile Ile Gln Gly Val Pro Ser Gln
                    245                 250                 255

Arg Val Ala Arg Pro Thr Ser Leu His Pro Phe Asn Ile Tyr Arg His
                260                 265                 270

Leu Arg Thr Val Asn Pro Ser Pro Tyr Leu Phe Tyr Ile Asp Cys Leu
                275                 280                 285

Asp Phe Gln Ile Ile Gly Ala Ser Pro Glu Leu Leu Cys Lys Ser Asp
                290                 295                 300

Ser Lys Asn Arg Val Ile Thr His Pro Ile Ala Gly Thr Val Lys Arg
305                 310                 315                 320

Gly Ala Thr Thr Glu Glu Asp Asp Ala Leu Ala Asp Gln Leu Arg Gly
                    325                 330                 335

Ser Leu Lys Asp Arg Ala Glu His Val Met Leu Val Asp Leu Ala Arg
                340                 345                 350

Asn Asp Ile Asn Arg Ile Cys Asp Pro Leu Thr Thr Ser Val Asp Lys
                355                 360                 365

Leu Leu Thr Ile Gln Lys Phe Ser His Val Gln His Leu Val Ser Gln
                370                 375                 380

Val Ser Gly Val Leu Arg Pro Glu Lys Thr Arg Phe Asp Ala Phe Arg
385                 390                 395                 400

Ser Ile Phe Pro Ala Gly Thr Val Ser Gly Ala Pro Lys Val Arg Ala
                    405                 410                 415

Met Glu Leu Ile Ala Glu Leu Glu Gly Glu Arg Arg Gly Val Tyr Ala
                    420                 425                 430

Gly Ala Val Gly His Trp Ser Tyr Asp Gly Lys Thr Met Asp Asn Cys
                435                 440                 445

Ile Ala Leu Arg Thr Met Val Tyr Lys Asp Gly Ile Ala Tyr Leu Gln
                450                 455                 460

Ala Gly Gly Gly Ile Val Tyr Asp Ser Asp Glu Tyr Asp Glu Tyr Val
465                 470                 475                 480
```

-continued

Glu Thr Met Asn Lys Met Met Ala Asn His Ser Thr Ile Val Gln Ala
                485                 490                 495

Glu Glu Leu Trp Ala Asp Ile Val Gly Ser Ala
            500                 505

<210> SEQ ID NO 19
<211> LENGTH: 371
<212> TYPE: PRT
<213> ORGANISM: Aspergillus niger

<400> SEQUENCE: 19

Met Pro Leu Ile Ser Thr Thr Glu Val Asn Glu Asp Thr Arg Val Leu
1               5                   10                  15

Gly Tyr Asp Pro Leu Leu Pro Pro Gln Tyr Leu Gln Asn Glu Ile Pro
            20                  25                  30

Gly Lys Lys Glu Ser Leu Glu Ala Val Arg Ser Gly Arg Asn Gln Ala
        35                  40                  45

Met Lys Ile Ile Glu Lys Arg Asp Asp Arg Leu Leu Val Val Val Gly
    50                  55                  60

Pro Cys Ser Ile His Asp Pro Ala Thr Ala Leu Glu Tyr Ala Gln Arg
65                  70                  75                  80

Leu Lys Glu Leu Ser Glu Lys Leu Ser Asp Asp Leu Cys Val Ile Met
                85                  90                  95

Arg Ala Tyr Leu Glu Lys Pro Arg Thr Thr Val Gly Trp Lys Gly Leu
            100                 105                 110

Ile Asn Asp Pro Asp Ile Asp Glu Ser Tyr Asn Ile Asn Lys Gly Leu
        115                 120                 125

Arg Val Ser Arg Gln Leu Tyr Ala Asp Leu Thr Ser Met Gly Met Pro
    130                 135                 140

Ile Ala Ser Glu Met Leu Asp Thr Ile Ser Pro Gln Tyr Leu Ala Asp
145                 150                 155                 160

Leu Ile Ser Leu Gly Ala Ile Gly Ala Arg Thr Thr Glu Ser Gln Leu
                165                 170                 175

His Arg Glu Leu Ala Ser Gly Leu Ser Phe Pro Ile Gly Phe Lys Asn
            180                 185                 190

Gly Thr Asp Gly Asn Leu Thr Val Ala Ile Asp Ala Ile Gly Ala Ala
        195                 200                 205

Ala His Pro His Arg Phe Leu Gly Val Thr Leu Gln Gly Leu Ala Ala
    210                 215                 220

Ile Thr Lys Thr Ala Gly Asn Glu His Gly Phe Val Ile Leu Arg Gly
225                 230                 235                 240

Gly Asn Lys Gly Thr Asn Tyr Asp Arg Glu Ser Ile Lys Ala Ala Arg
                245                 250                 255

Glu Ala Leu Ala Gly Lys Lys Gln Pro Glu Val Val Met Val Asp Cys
            260                 265                 270

Ser His Gly Asn Ser Asn Lys Asn His Arg Asn Gln Pro Leu Val Ala
        275                 280                 285

Lys Glu Val Ser Asp Gln Leu Arg Glu Gly Gln Asp Ala Ile Ile Gly
    290                 295                 300

Val Met Ile Glu Ser Asn Ile Asn Glu Gly Asn Gln Lys Val Pro Pro
305                 310                 315                 320

Glu Gly Pro Ser Gly Leu Arg Lys Gly Val Ser Ile Thr Asp Ala Cys
                325                 330                 335

Ile Asp Trp Glu Thr Thr Val Gln Val Leu Glu Asp Leu Ala Asp Gly 340                 345                 350
Val Arg Ala Arg Arg Ala Ala Lys Ala Ala Gln Ala Lys Ala Ser Asn
            355                 360                 365

Gly Thr His
        370

<210> SEQ ID NO 20
<211> LENGTH: 527
<212> TYPE: PRT
<213> ORGANISM: Aspergillus niger

<400> SEQUENCE: 20

Met Ala Pro Pro Ile Thr Val Val Pro Ser Leu Glu Thr Ala Ser Glu
1               5                   10                  15

Val Ile Ala Gln Ser Lys Asn Ala Gln Phe Pro Pro Asn Leu Leu Pro
            20                  25                  30

Leu Thr Thr Ser Ile Pro Ala Asp Leu Leu Thr Pro Thr Leu Ala Tyr
        35                  40                  45

Leu Lys Ile Ala Glu Lys Cys Ala Asn Val Ile Gly Leu Ser Arg Ser
    50                  55                  60

Lys Leu Ser Phe Leu Tyr Glu Ser Ala Thr Thr Glu Thr Ile Gly
65                  70                  75                  80

Arg Tyr Leu Phe Val Gly Ala Gly Pro Arg Lys Ile Ile Lys Thr Gly
                85                  90                  95

Pro Gly His Gly Pro Glu Cys Asp Pro Met Pro Ile Leu Glu Glu Glu
            100                 105                 110

Leu Ser Gly Phe Arg Val Ala Thr Val Pro Gly Leu Thr Leu Pro Pro
        115                 120                 125

Leu Thr Gly Gly Ala Ile Gly Tyr Val Gly Tyr Asp Cys Val Arg Tyr
    130                 135                 140

Phe Glu Pro Lys Thr Ala Arg Pro Met Lys Asp Ile Leu Gln Ile Pro
145                 150                 155                 160

Glu Ser Leu Phe Met Leu Phe Asp Thr Ile Val Ala Phe Asp His Phe
                165                 170                 175

Phe Gln Val Val Lys Val Ile Thr Tyr Ile Ser Ile Pro Gly Asn Asp
            180                 185                 190

Ser Glu Leu Glu Ser Val Tyr Arg Gln Gly Gln Glu Val Leu Gln Arg
        195                 200                 205

Thr Ile Asp Val Leu Leu Arg Pro Asp Tyr Thr Leu Pro Pro Gln Gly
    210                 215                 220

Pro Ile Ile Gln Asn Gln Glu Tyr Thr Ser Asn Ile Gly Arg Glu Gly
225                 230                 235                 240

Tyr Glu Arg His Val Thr Arg Leu Lys Glu His Ile Ser Lys Gly Asp
                245                 250                 255

Ile Phe Gln Thr Val Pro Ser Gln Arg Leu Ser Arg Pro Thr Ser Leu
            260                 265                 270

His Pro Phe Asn Leu Phe Arg His Leu Arg Thr Val Asn Pro Ser Pro
        275                 280                 285

Tyr Leu Phe Tyr Ile Asp Cys Glu Asp Phe Gln Leu Val Gly Ala Ser
    290                 295                 300

Pro Glu Leu Leu Val Lys Glu Glu Lys Gly Arg Ile Ile Thr His Pro
305                 310                 315                 320

Ile Ala Gly Thr Val Lys Arg Gly Lys Thr Pro Glu Glu Asp Ala Ala
                325                 330                 335

```
Leu Ala Asn Glu Leu Thr Ser Ser Val Lys Asp Arg Ala Glu His Val
                340                 345                 350

Met Leu Val Asp Leu Ala Arg Asn Asp Val Asn Arg Val Cys Asp Pro
            355                 360                 365

Ile Thr Thr Gln Val Asp Arg Leu Met Val Val Glu Lys Phe Ser His
370                 375                 380

Val Gln His Leu Val Ser Gln Val Ser Gly Ile Leu Arg Pro Glu Lys
385                 390                 395                 400

Thr Arg Phe Asp Ala Phe Arg Ser Ile Phe Pro Ala Gly Thr Val Ser
                405                 410                 415

Gly Ala Pro Lys Val Arg Ala Met Gln Leu Ile Ala Glu Leu Glu Gly
            420                 425                 430

Glu Lys Arg Gly Val Tyr Ala Gly Ala Val Gly Tyr Phe Gly Tyr Asn
        435                 440                 445

Ile Ala Ser Ala Asp Gly Lys Thr Glu Met Pro Gly Ala Met Asp Thr
450                 455                 460

Cys Ile Ala Leu Arg Thr Met Met Val Lys Asn Gly Val Ala Tyr Leu
465                 470                 475                 480

Gln Ala Gly Gly Gly Ile Val Phe Asp Ser Asp Pro Tyr Asp Glu Tyr
                485                 490                 495

Val Glu Thr Leu Asn Lys Leu Gly Ala Asn Ile Ala Cys Ile Lys Gly
            500                 505                 510

Ala Glu Ala Lys Tyr Leu Ser Leu Glu Glu Glu Ser Arg Arg Ala
        515                 520                 525

<210> SEQ ID NO 21
<211> LENGTH: 260
<212> TYPE: DNA
<213> ORGANISM: Artificial sequence
<220> FEATURE:
<223> OTHER INFORMATION: synthetic promoter

<400> SEQUENCE: 21
cacggaatga actttcattc cgctgaagct tgtcaatcgg aatgaaggtt cattccggct      60
agttctcccc ggaaactgtg gccatatgcc ctgcagtgcc tgatcacctt atcaagtggc     120
caaatatccc actataaaag gcttgggaac ccctcgttct gtcttacctt ctatcatctt     180
accaaatcca ctcctcttcc ttcatacatc aatcttacca atcaactacc tctacaactc     240
caatacactt aattaaaatg                                                 260

<210> SEQ ID NO 22
<211> LENGTH: 216
<212> TYPE: DNA
<213> ORGANISM: Artificial sequence
<220> FEATURE:
<223> OTHER INFORMATION: synthetic promoter

<400> SEQUENCE: 22
gcacggaatg aactttcatt ccgctgaagc ttgtcaatcg gaatgaaggt tcattccggc      60
tagttctccc cggaaactgt ggccatatgt caaagactag gatggataa atggggtata     120 taaagcaccc tgactccctt cctccaagtt ctatctaacc agccatccta cactctacat     180
atccacacca atctactaca attattaatt aaaatg                               216

<210> SEQ ID NO 23
<211> LENGTH: 248
<212> TYPE: DNA
<213> ORGANISM: Artificial sequence
```

```
<220> FEATURE:
<223> OTHER INFORMATION: synthetic promoter

<400> SEQUENCE: 23
gcacggaatg aactttcatt ccgctgaagc ttgtcaatcg gaatgaaggt tcattccggc      60
tagttctccc cggaaactgt ggccatatgc gccccaagag agctgaagat gctgagtagg     120
gttgtccagg cagcacatat ataagatgct tcgtcccctc ccatcgagtc cttctttttct   180 ctctctcatc aatcactcta cttcctactc taccttaaac tcttcactac ttcatacgat    240
taacaatg                                                              248

<210> SEQ ID NO 24
<211> LENGTH: 612
<212> TYPE: DNA
<213> ORGANISM: Artificial sequence
<220> FEATURE:
<223> OTHER INFORMATION: synthetic promoter

<400> SEQUENCE: 24
cattttaatt aagtgtattg gagttgtaga ggtagttgat tggtaagatt gatgtatgaa     60
ggaagaggag tggatttggt aagatgatag aaggtaagac agaacgaggg gttcccaagc   120
cttttatagt gggatatttg gccacttgat aaggtgatca ggcactgcag gcatatggc    180 cacagttcc ggggagaact agccggaatg aaccttcatt ccgattgaca agcttcagcg   240
gaatgaaagt tcattccgtg cttatctaga gtccggaatg aaccttcatt ccgtcacatc   300
ctaggtctcg gaatgaatgt tcattccgac tagccggaat gaaccttcat tccgattgac   360
aagcttcagc ggaatgaaag ttcattccgt gcttatctag agtccggaat gaaccttcat   420
tccgtcacat cctaggtctc ggaatgaatg ttcattccga ctagccgagc aaatgcctgc   480
atatgttcaa agactaggat ggataaatgg ggtatataaa gcaccctgac tcccttcctc   540
caagttctat ctaaccagcc atcctacact ctacatatcc acaccaatct actacaatta   600
ttaattaaaa tg                                                         612

<210> SEQ ID NO 25
<211> LENGTH: 185
<212> TYPE: DNA
<213> ORGANISM: Artificial Sequence
<220> FEATURE:
<223> OTHER INFORMATION: core promotet

<400> SEQUENCE: 25
ccaaaattgt aatttaccga gaattgtaaa tttacctgaa aaccctacgc tatagtttcg     60
actataaata ccaaacttag gacctcactt cagaatcccc tcgtcgctgc gtctctctcc   120
cgcaaccttc gattttcgtt tattcgcatc catcggagag agaaaacaat caattaatta   180
aaatg                                                                 185
```

HETEROLOGOUS PRODUCTION OF PSILOCYBIN

CROSS-REFERENCE TO RELATED APPLICATIONS

This application is a national phase entry under 35 U.S.C. 371 of PCT International Application No. PCT/FI2019/050199 filed Mar. 11, 2019, which claims priority to Finnish Patent Application No. 20185254, filed Mar. 19, 2018, the disclosure of each of these applications is expressly incorporated herein by reference in their entirety.

FIELD OF THE INVENTION

The present description relates to producing metabolites in a recombinant host cell by metabolic engineering. In particular the invention provides a novel method, a novel recombinant host cell and a novel production system for producing psilocybin and related compounds.

BACKGROUND

Psilocybin is currently being evaluated (phase II clinical trials) as highly promising drug for medical use for treatment of depression, anxiety and other mental illnesses, such as obsessive-compulsive disorder [1,2].

Psilocybin is nowadays being produced for medical use by multistep chemical organic syntheses [3,4]. Previous methods for psilocybin production are relying on the use of harsh chemicals, resulting in accumulation of toxic waste, and these methods could be inefficient and not environmental friendly. Alternatively, psilocybin can be extracted from natural sources, as it is bio-synthesized in certain species of mushrooms. However, this method relies on supply of the mushrooms, whose production could be inconsistent and difficult to control.

Genes responsible for biosynthesis of psilocybin in basidiomycete mushrooms have been identified and disclosed in a paper by Fricke et al. (2017) [5]. The paper states that genetic manipulation of the basidiomycete genes is not straightforward (p. 12353 left column, first paragraph) and teaches to use in vitro approach for biosynthesis of compounds.

It is an object of the present invention to solve or alleviate at least some of the above problems of prior technology used to produce psilocybin.

SUMMARY OF THE INVENTION

According to the first aspect there is provided a recombinant host cell comprising:
  at least one heterologous polynucleotide selected from polynucleotides encoding PsiD, PsiH, PsiK, and PsiM;
  wherein the at least one heterologous polynucleotide is operably linked to at least one promoter which is capable of directing expression of said heterologous polynucleotides in the host cell.

According to an aspect of the invention is provided a recombinant host cell comprising:
  heterologous polynucleotides encoding PsiD, PsiH, PsiK, and PsiM;
  wherein the heterologous polynucleotides are operably linked to at least one promoter which is capable of directing expression of said heterologous polynucleotides in the host cell;
  and wherein the recombinant host cell is capable of producing psilocybin.

According to another aspect there is provided a recombinant host cell comprising at least one heterologous polynucleotide encoding PsiD, PsiH, PsiK, and PsiM; wherein the at least one heterologous polynucleotide(s) is/are operably linked to at least one promoter which is capable of directing expression of said heterologous polynucleotide(s) in the host cell.

According to the second aspect there is provided a method for producing metabolites comprising
  a. providing the recombinant host cell of an aspect described above;
  b. cultivating the recombinant host cell in conditions allowing growth and propagation of the host cell;
  c. continuing cultivating the recombinant host cells to synthesize the metabolites; and
  d. recovering at least one metabolite synthesized by an enzyme encoded by the heterologous polynucleotide of the host cell.

According to the third aspect there is provided a psilocybin production system comprising:
  a production unit containing the host cell of an aspect described above; and
  a control unit comprising controlling means for operating the production unit.

Different embodiments of the present invention will be illustrated or have been illustrated only in connection with some aspects of the invention. A skilled person appreciates that any embodiment of an aspect of the invention may apply to the same aspect of the invention or to other aspects of the invention.

All three expression cassettes (sTF, PsiH/D and PsiK/M) are in one embodiment single-copy integrated in three separate loci in the genome of the production host. In one embodiment, the PsiH/D and the sTF cassettes are fused forming a single DNA. In one embodiment, the PsiK/M and the sTF cassettes are fused forming a single DNA. The core promoters (cp) and terminators (term) used in the expression cassettes are selected to provide efficient gene expression levels in the host organism.

Figure 3:
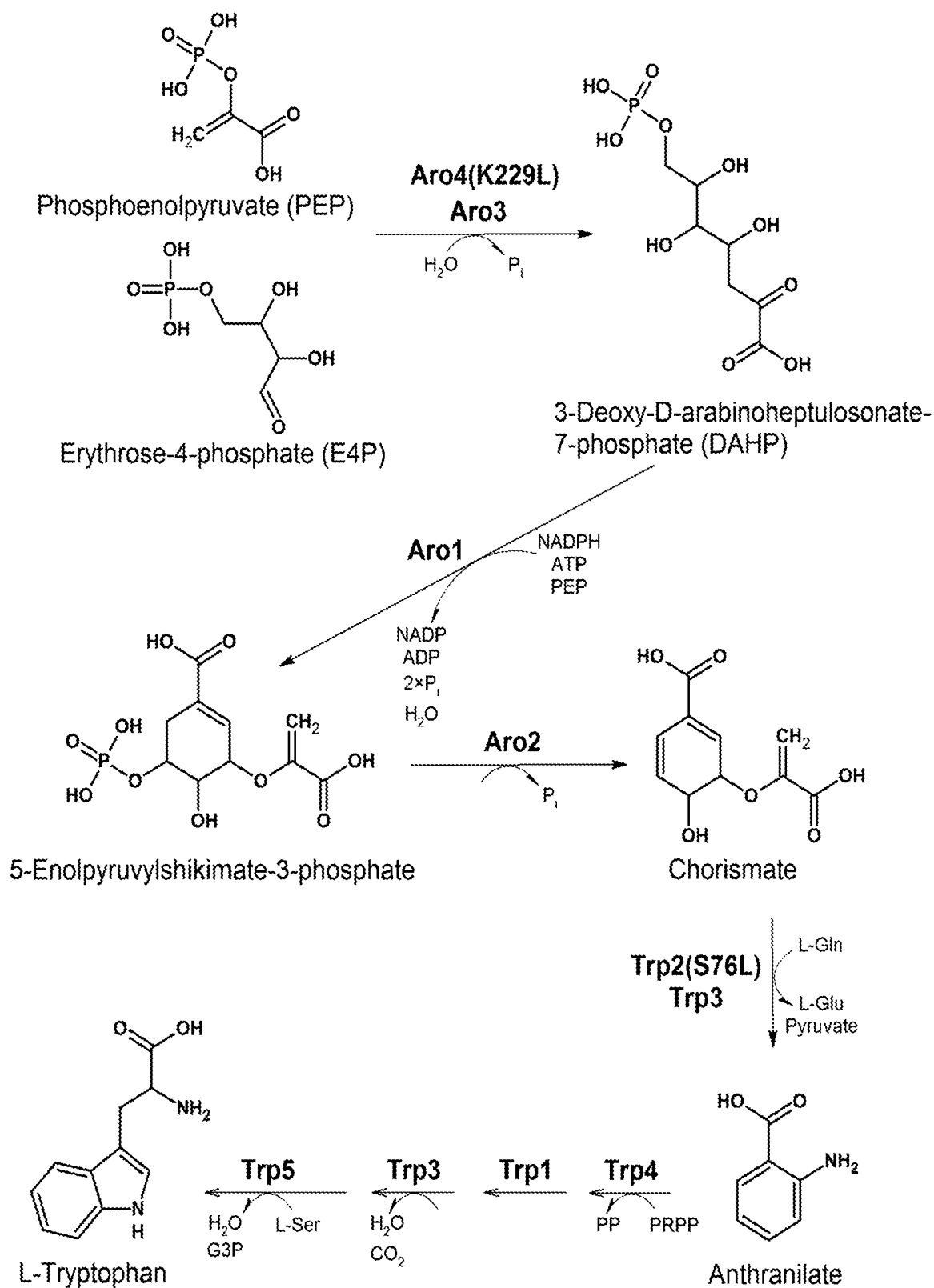

FIG. 3 discloses a scheme of native metabolic pathway leading to biosynthesis of L-tryptophan, where certain key enzymes have been modified for improved L-tryptophan production. The example pathway from the yeast *Saccharomyces cerevisiae* shown herein, uses phosphoenolpyruvate (PEP) and erythrose-4-phosphate (E4P) as initial precursors. Phosphoenolpyruvate (PEP) is a metabolic intermediate of glycolysis, and erythrose-4-phosphate (E4P) is a metabolic intermediate of the pentose phosphate pathway, both being native pathways in the central carbon metabolism of eukaryotic organisms. In the shown pathway, PEP and E4P are converted into 3-deoxy-D-arabinoheptulosonate 7-phosphate (DAHP) in the first enzymatic reaction catalysed by the Aro4 or Aro3 enzyme. The activity of these enzymes is regulated by allosteric inhibition, for instance the Aro4 (K229L) mutant is resistant to this inhibition—expression of the mutant is resulting in higher metabolic flux through the pathway. DAHP is then converted into chorismate in a series of enzymatic reactions catalysed by the Aro1 and Aro2 enzymes. Chorismate is a metabolic intermediate used for the biosynthesis of aromatic compounds, such as aromatic amino acids L-tryptophan, L-tyrosine, and L-phenylalanine. The pathway from PEP and E4P to chorismate is referred as the shikimate pathway. In the L-tryptophan biosynthetic pathway, chorismate is first converted into anthranilate in an enzymatic reaction catalysed by the hetero-oligomeric anthranilate synthase—indole-3-glycerol phosphate synthase enzyme complex encoded by Trp2 and Trp3, respectively. The activity of Trp2 subunit is also regulated by allosteric inhibition, however, the allosterically insensitive Trp2 (S76L) mutant is known. By over-expressing genes encoding the Trp2 (S76L) and Trp3, the flux in L-tryptophan pathway can be increased resulting in increased production of L-tryptophan. Anthranilate is subsequently converted into L-tryptophan in four enzymatic reactions catalysed by the Trp4, Trp1, Trp3, and Trp5 enzymes.

Figure 1:
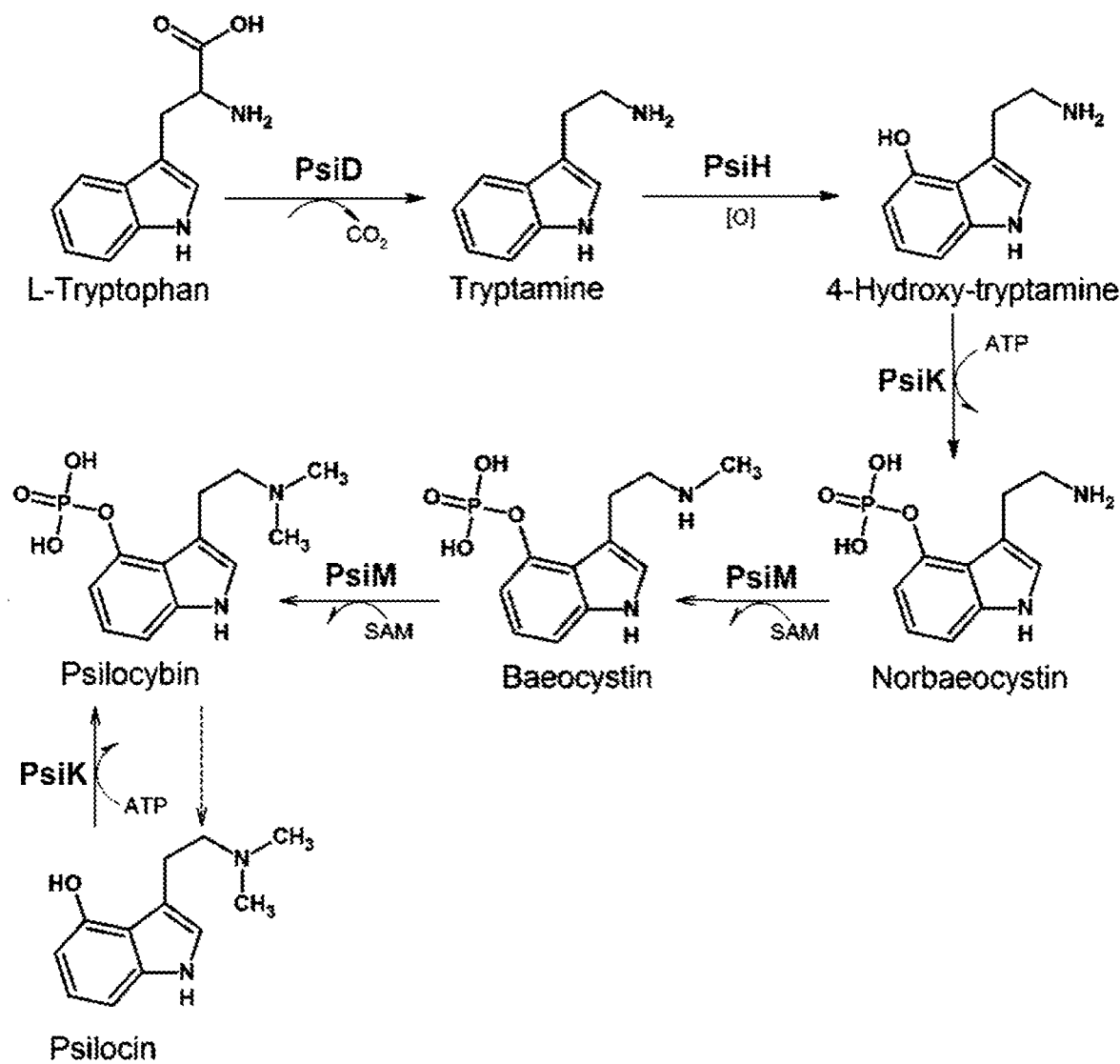
FIG. 1 discloses a scheme of enzymatic pathway for biosynthesis of psilocybin. The pathway uses amino-acid L-tryptophan as an initial substrate. L-Tryptophan is converted into tryptamine and $CO_2$ in the first enzymatic reaction catalysed by the PsiD enzyme. Tryptamine is converted into 4-hydroxy-tryptamine in the second enzymatic reaction catalysed by the PsiH enzyme, where oxygen is used in the reaction to form the hydroxyl-group. 4-hydroxy-tryptamine is converted into norbaeocystin in the third enzymatic reaction catalysed by the PsiK enzyme, where adenosine triphosphate (ATP) is used as a donor of the phosphate group. Norbaeocystin is converted into baeocystin and eventually psilocybin in the fourth and fifth enzymatic reactions catalysed by the PsiM enzyme, where S-adenosyl methionine (SAM) is used as a donor of the methyl groups. Psilocybin can be converted into psilocin in a reaction catalysed either by a native host phosphatase, or spontaneously. It can be re-phosphorylated by the PsiK enzyme to form psilocybin again.
Figure 2:
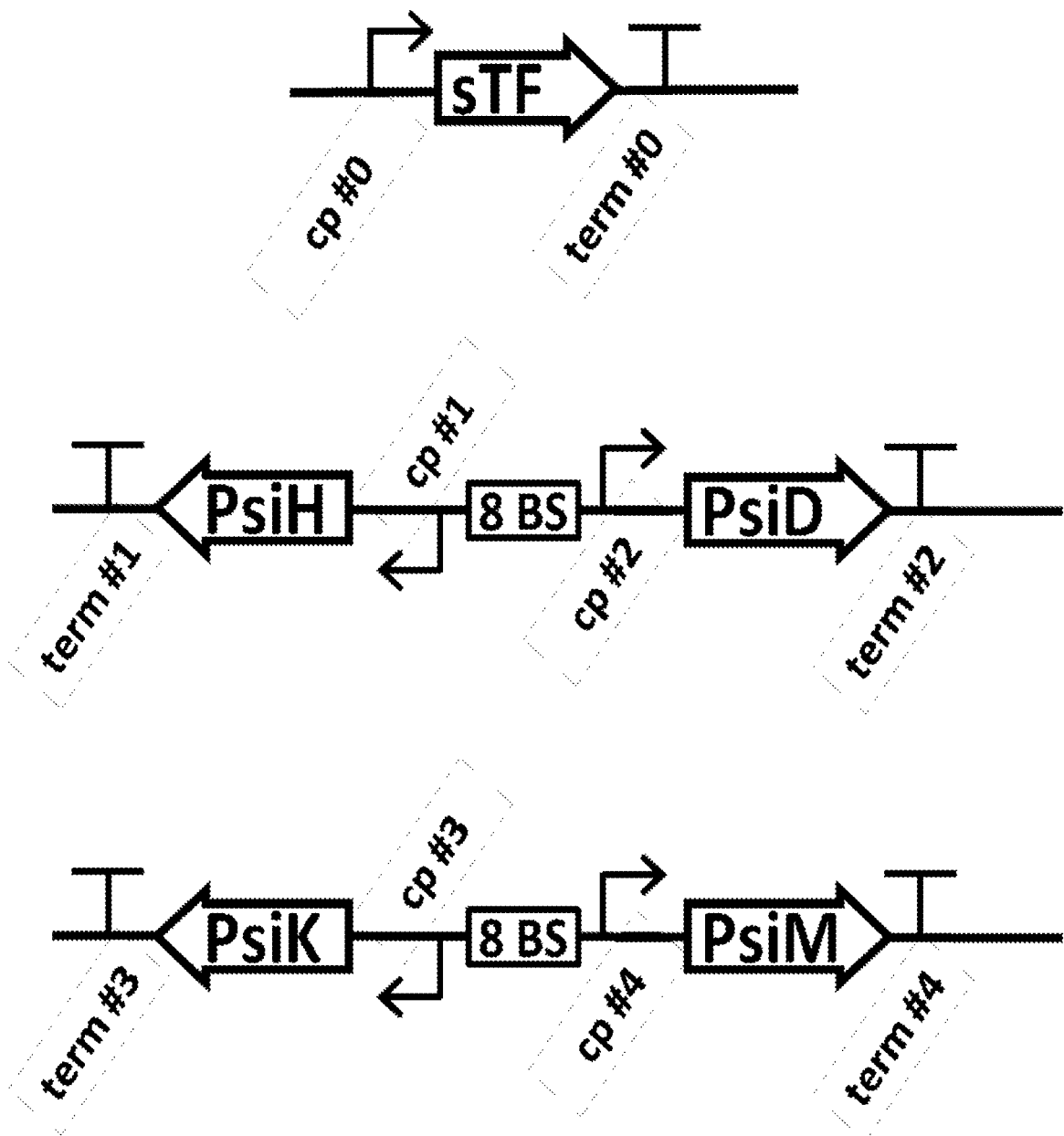
FIG. 2 discloses schemes of gene expression cassettes used for construction of a psilocybin heterologous metabolic pathway. The expression of the four psilocybin-pathway genes (PsiH, PsiD, PsiK, and PsiM) is controlled by a synthetic (artificial) transcription factor (sTF). The sTF is expressed from a core promoter (cp #0), which allows low and constitutive production of sTF. The sTF binds to eight sTF-dependent binding sites (8 BS) in the bi-directional artificial promoters, and triggers high constitutive expression of the Psi-genes. The Psi-genes expression cassettes are designed and constructed as bi-directional dual gene expression cassettes allowing co-expression of two genes (such as PsiH and PsiD, or PsiK and PsiM) from one genomic locus.
Figure 4:
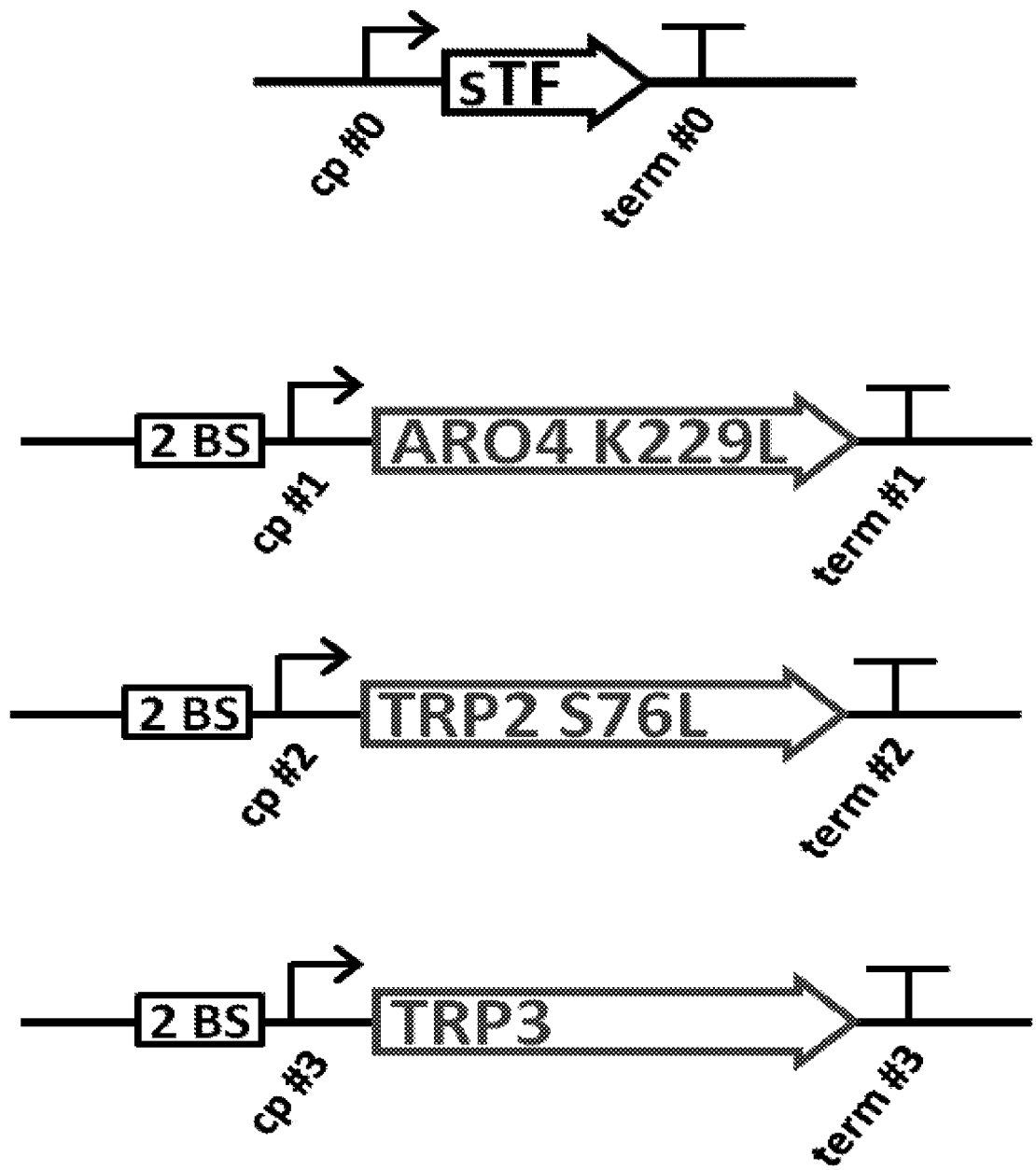

FIG. 4 discloses a scheme of gene expression cassettes used for construction of a host with elevated production of L-tryptophan. The example is given on the genes of yeast *S. cerevisiae*, but homologous genes from other organisms can be used, as well. The expression of the three selected target genes involved in the L-tryptophan biosynthesis (Aro4-K229L mutant, Trp2-S76L mutant, and Trp3) is controlled by the same synthetic (artificial) transcription factor (sTF) as in the case of psilocybin pathway (FIG. 2). The sTF binds to two sTF-dependent binding sites (2 BS) in the artificial promoters, and triggers moderate expression of the target genes. All the target gene expression cassettes are single-copy integrated in place of the corresponding native genes and their promoters (replacing the native sequences) in the genome of the production host. It is also possible to integrate the expression cassettes elsewhere in the genome of the host. The core promoters (cp) and terminators (term) used in the expression cassettes are selected to provide efficient gene expression levels in the host organism.

Figure 5:
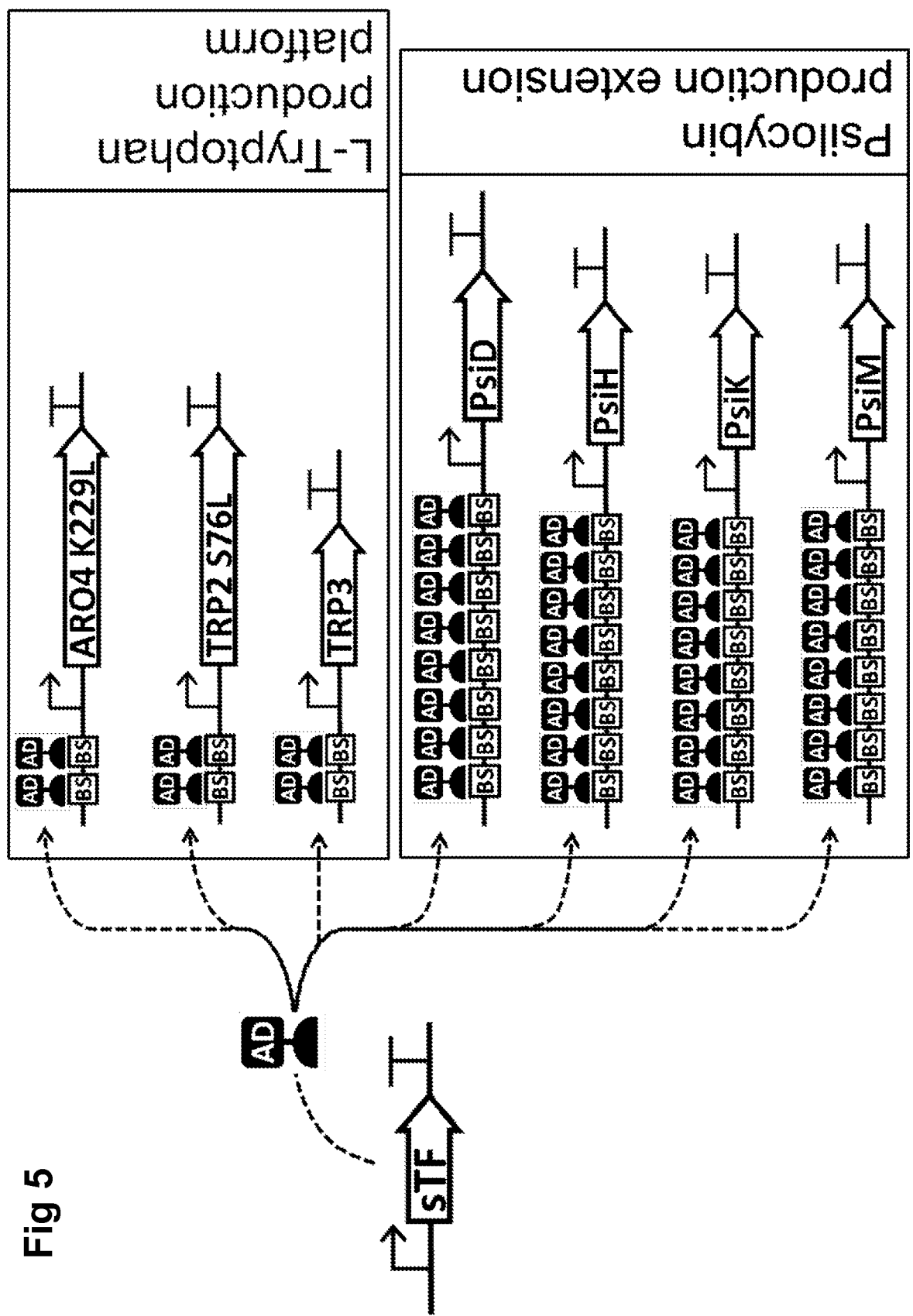

FIG. 5 discloses a scheme of genetic network used for gene expression control in a psilocybin production host. The sTF expression cassette provides sufficient amount of the sTF in the hosts for activation of the target genes. The sTF binds to the binding sites (BS) in the upstream sequences of the artificial promoters of these genes and triggers the expression via the activation domain (AD).

Figure 6A:
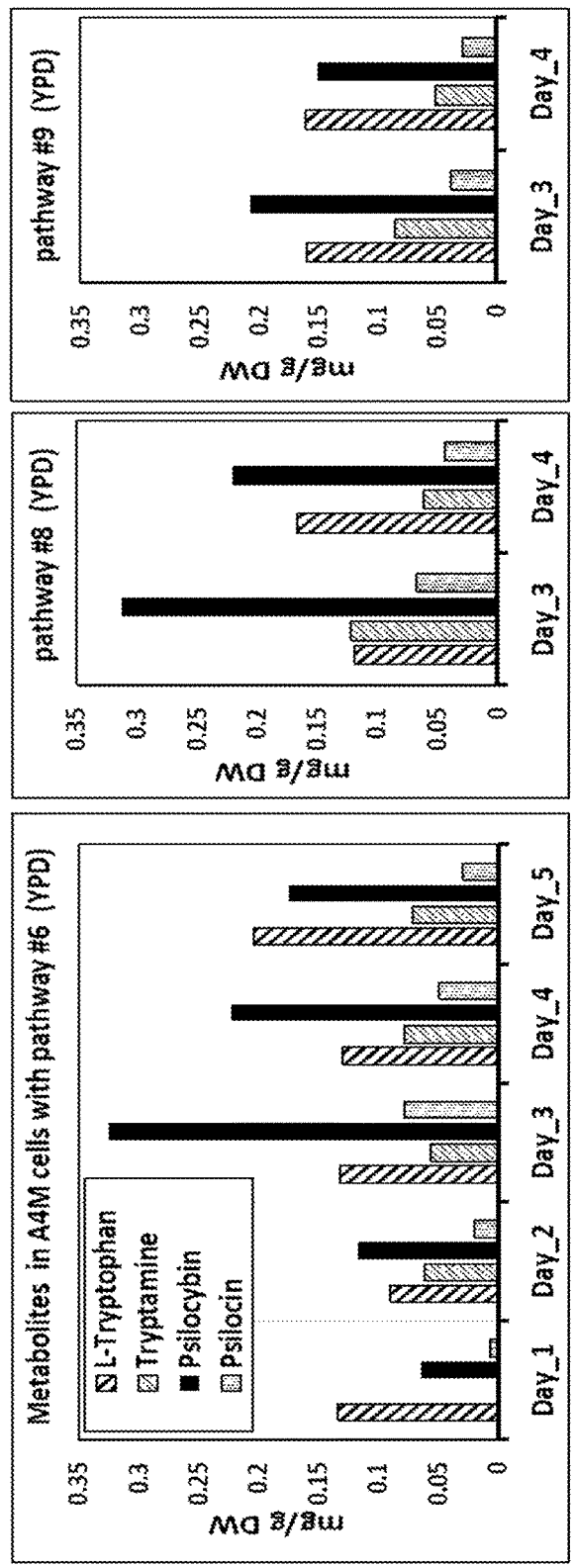
Figure 6B:
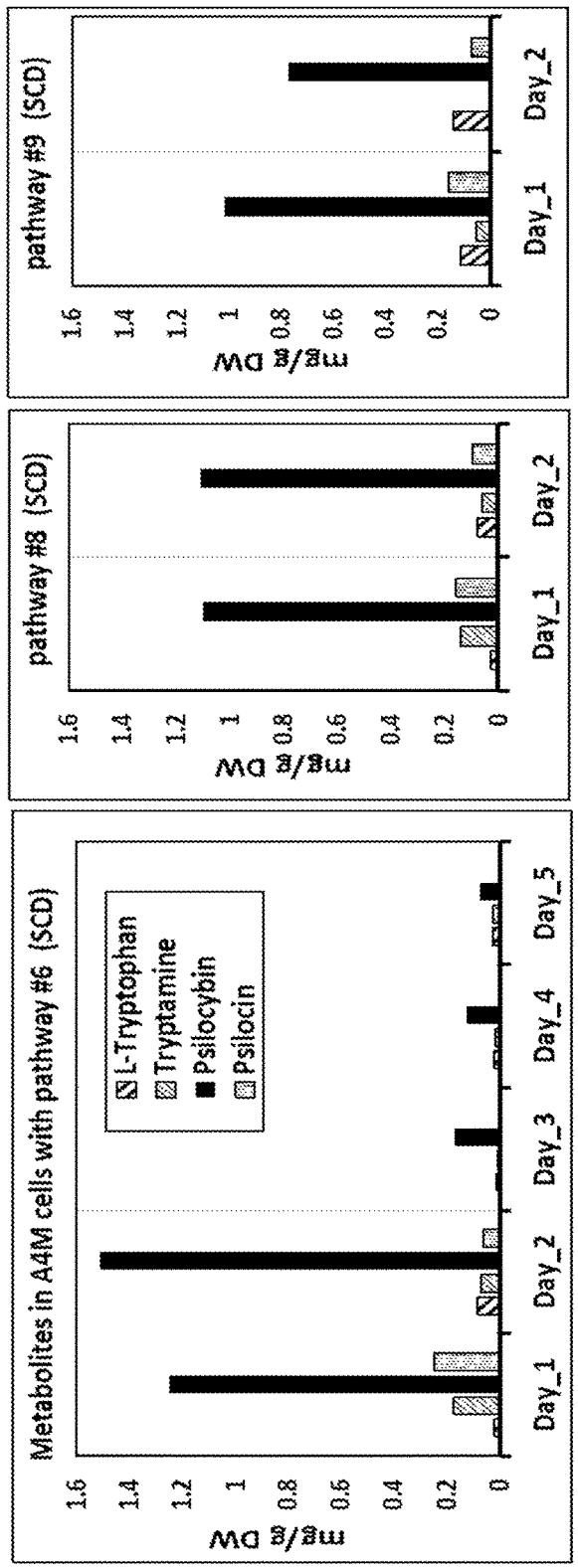

FIG. 6 discloses results from the analysis of psilocybin and related compounds in *S. cerevisiae* strains. The three *S. cerevisiae* hosts each carrying a version of the psilocybin pathway were selected based on initial screen shown in Table 2. The analysis was performed on the cell extracts for determination of intracellular metabolites contents. The metabolites shown are detected and quantified based on analytical standards (L-tryptophan, tryptamine, psilocybin, and psilocin). FIG. 6A discloses cultivations in the YPD medium. Analysis was done at days 1-5 for the Sc_A4M strain with the psilocybin pathway #6 (Table 2), and at days 3-4 for the Sc_A4M strains with the psilocybin pathways #8 and #9 (Table 2). FIG. 6B discloses cultivations in the SCD medium. Analysis was done at days 1-5 for the Sc_A4M strain with the psilocybin pathway #6 (Table 2), and at days 1-2 for the Sc_A4M strains with the psilocybin pathways #8 and #9.

FIG. 7 discloses results from the analysis of psilocybin and related compounds in media (supernatants) from cultures shown in FIG. 6. The results are shown for the Sc-sTF-background-strain (BS_Day1) cultivated one day, and for the Sc_A4M strain with the psilocybin pathway #6 cultivated 5 days and analysed at days 1-5.

Figure 7B:
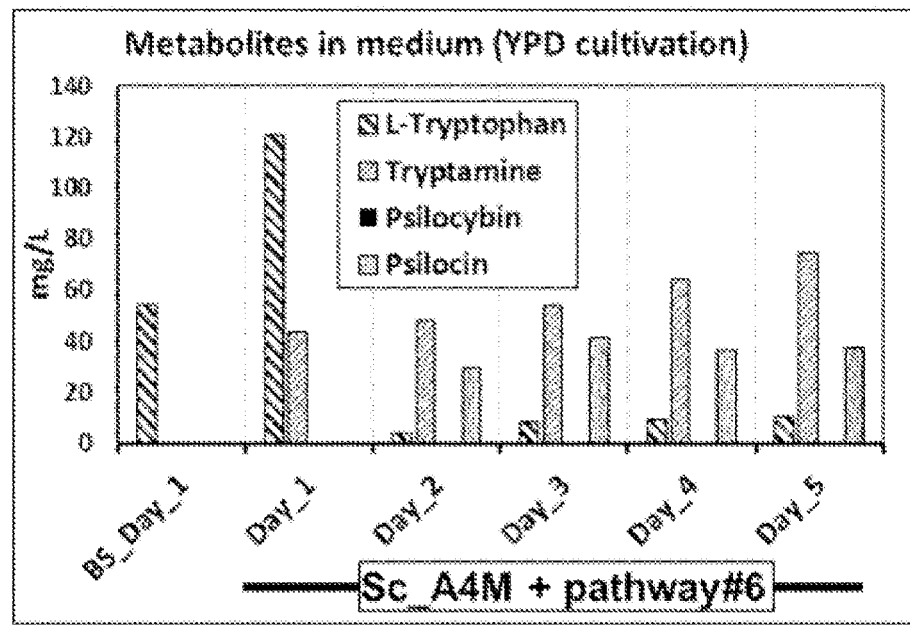
Figure 7A:
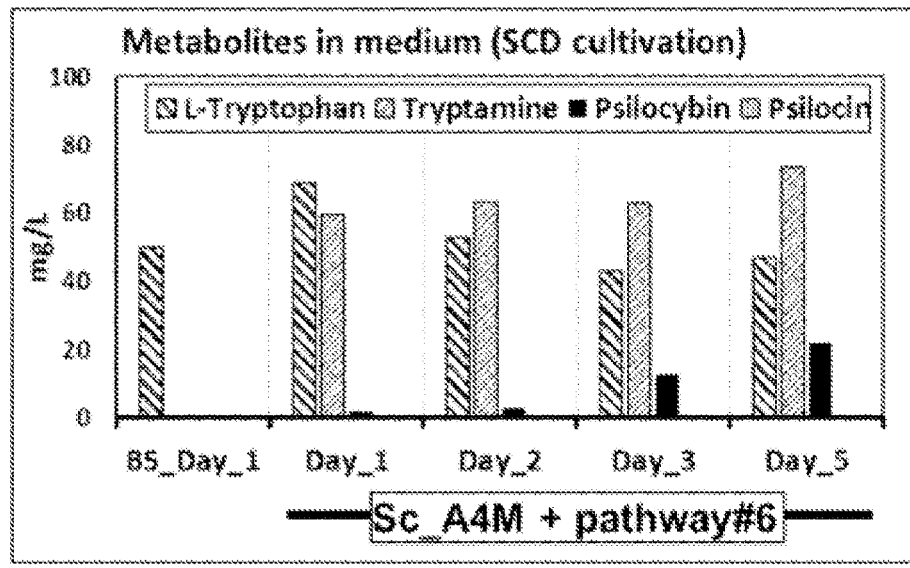

FIG. 7A discloses results obtained from cultivations in the YPD medium. FIG. 7B discloses results obtained from cultivations in the SCD medium.

Figure 8:
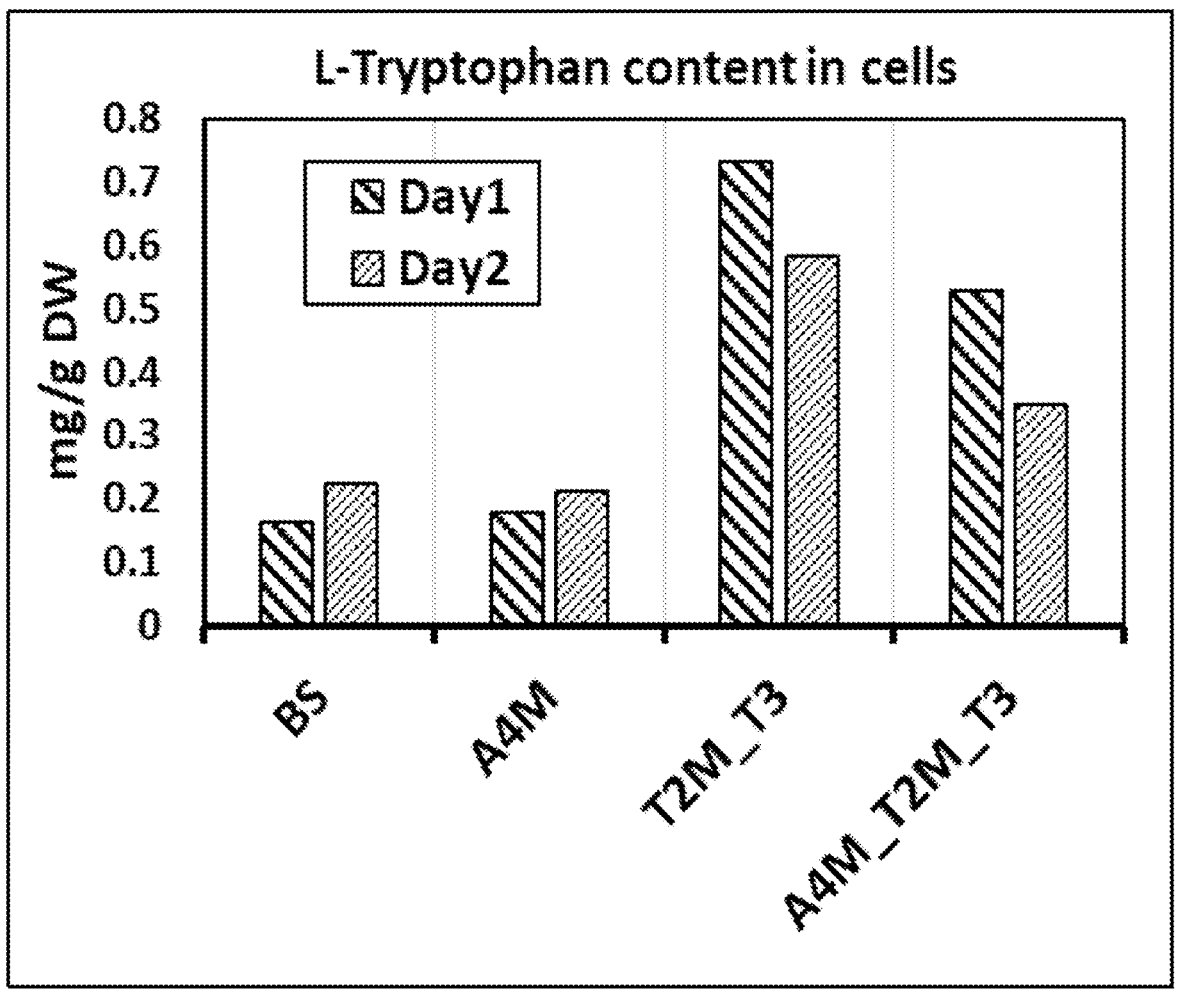

FIG. 8 discloses results from the analysis of intracellular L-tryptophan in the Sc-sTF-background-strain (BS), Sc_A4M strain, Sc_T2M_T3 strain, and Sc_A4M_T2M_T3 strain—all without the psilocybin pathway. Cultivations were done in the SCD medium. Analysis was done at days 1 and 2.

Figure 9A:
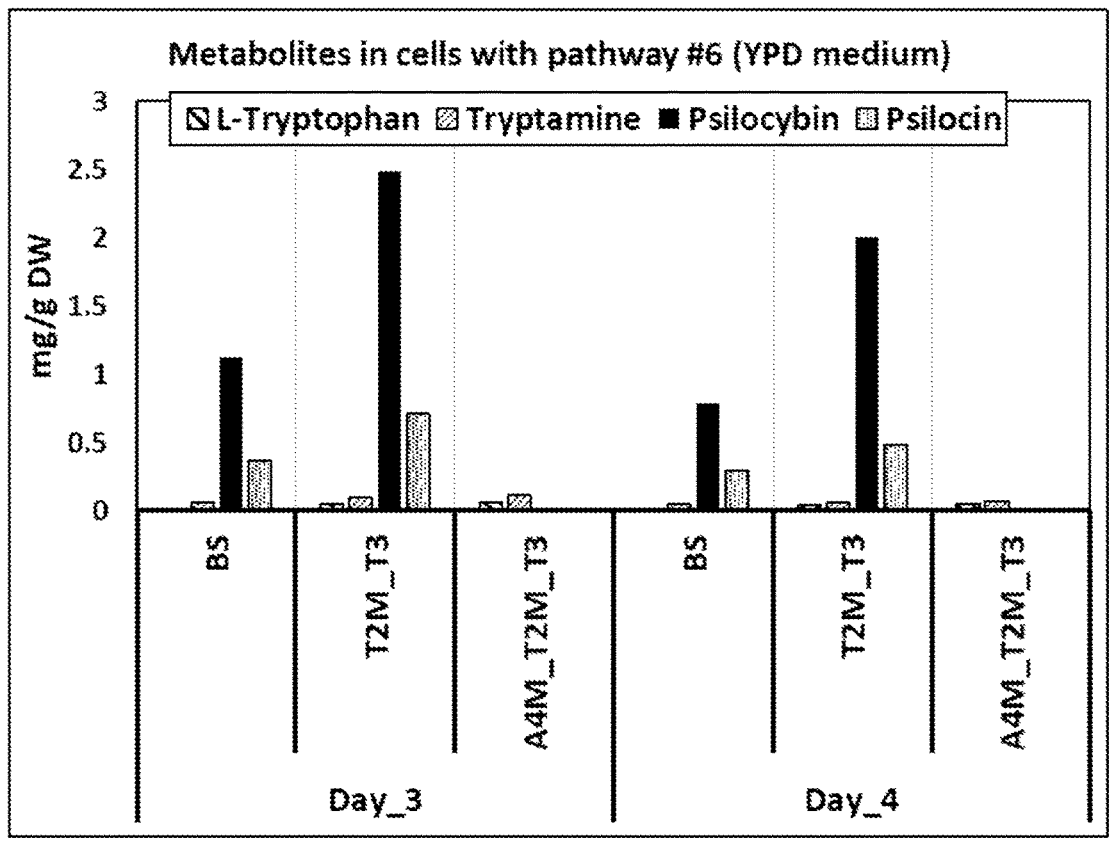
Figure 9B:
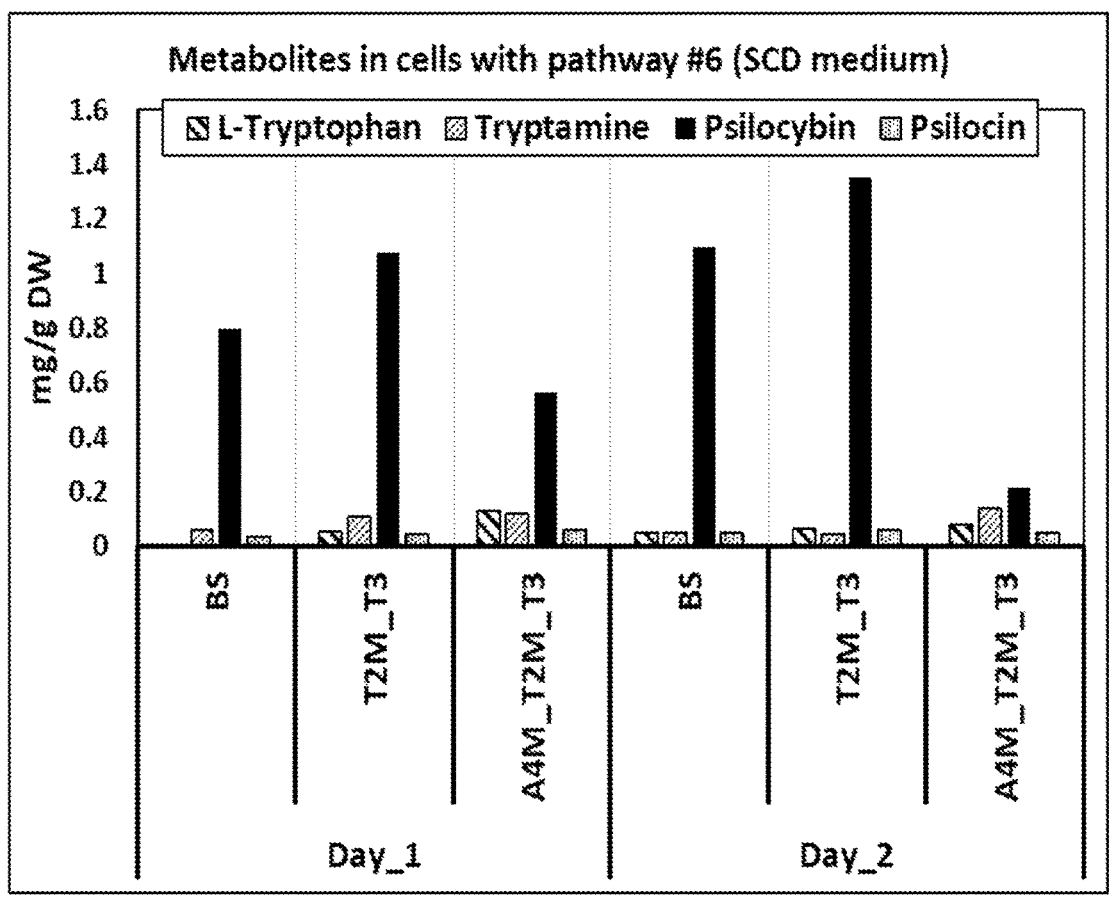

FIG. 9 discloses results from the analysis of psilocybin and related compounds in the strains with implemented psilocybin pathway #6. The results obtained with the Sc-sTF-background-strain (BS), Sc_T2M_T3 strain, and Sc_A4M_T2M_T3 strain are shown. FIG. 9A discloses results obtained from cultivations in the YPD medium and analysed at days 3 and 4. FIG. 9B discloses results obtained from cultivations in the SCD medium and analysed at days 1 and 2.

Figure 10A:
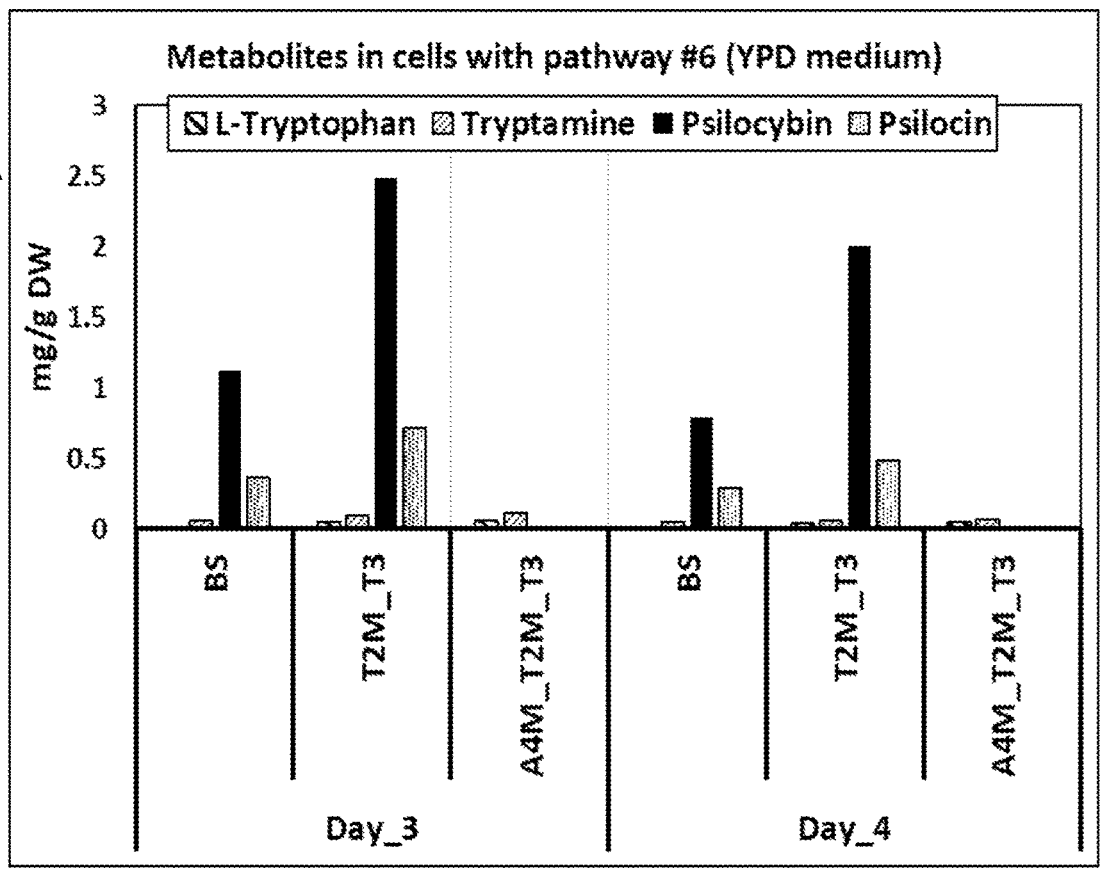
Figure 10B:
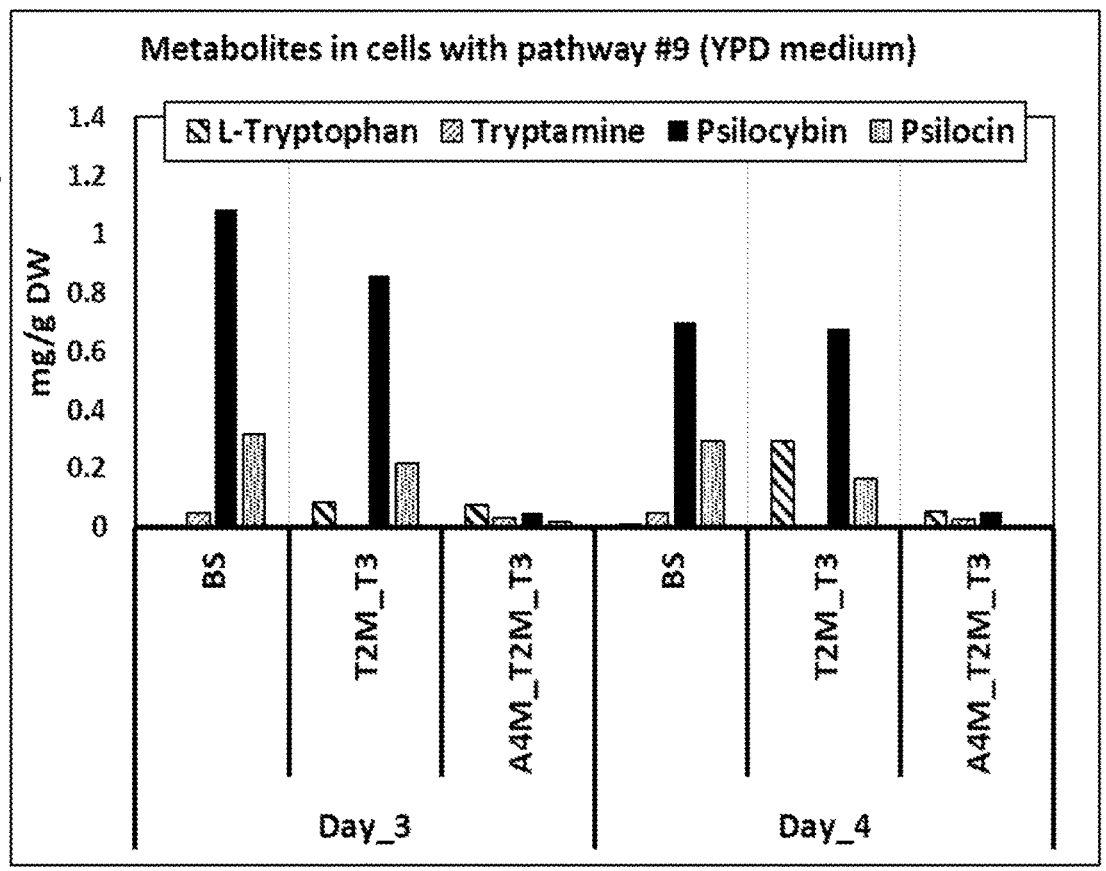

FIG. 10 discloses results from the analysis of psilocybin and related compounds the strains with implemented psilocybin pathway #9. The strains, cultivation conditions, and times of analyses are identical to FIG. 9. FIG. 10A discloses results obtained from cultivations in the YPD medium and analysed at days 3 and 4. FIG. 10B discloses results obtained from cultivations in the SCD medium and analysed at days 1 and 2.

Figure 11:
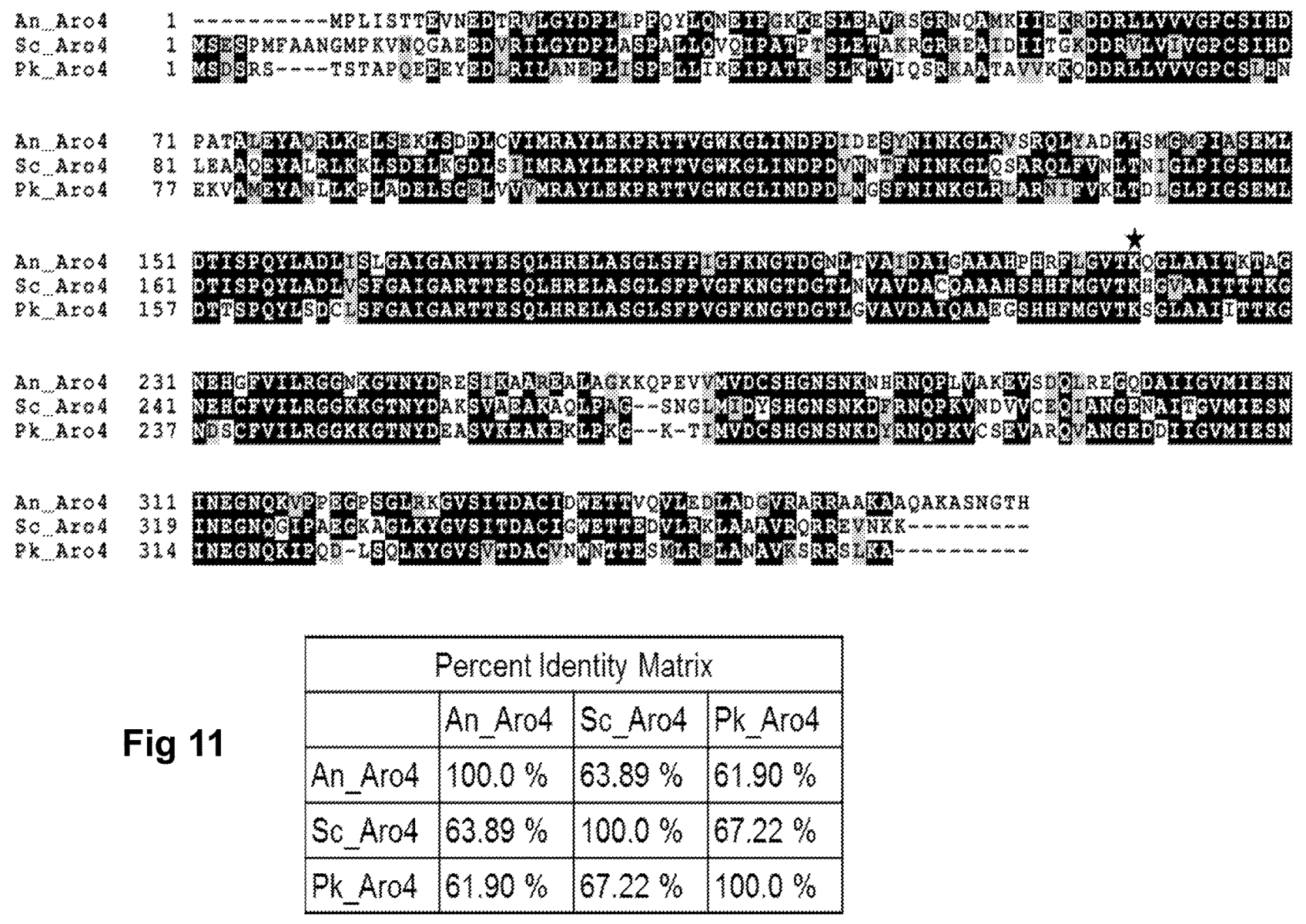

FIG. 11 discloses a protein sequence alignment and sequence identity matrix of Aro4 homologs from *S. cerevisiae* (Sc_Aro4; NCBI Reference Sequence: NP_009808.1), *Aspergillus niger* (An_Aro4; NCBI Reference Sequence: XP_001396195.1), and *Pichia kudriavzevii* (Pk_Aro4; NCBI Reference Sequence: XP_020545247.1). The star above the sequence alignment denotes the conserved lysine residue (K) which is critical for the allosteric regulation. The mutation of this amino acid results in alleviation of the allosteric regulation of the enzyme, it is K229 in *S. cerevisiae*, K219 in *A. niger*, and K225 in *P. kudriavzevii*. The sequence alignment and the identity values were determined with the Multiple Sequence Alignment tool Clustal Omega at the EMBL-EBI website (https://www.ebi.ac.uk/Tools/ msa/clustalo/). Visualization of the alignment was done with the BoxShade tool at the ExPASy website (https://embnet.vital-it.ch/software/BOX_form.html).

FIG. 12 discloses a protein sequence alignment and sequence identity matrix of Trp2 homologs from *S. cerevisiae* (Sc_Trp2; NCBI Reference Sequence: NP_011014.1), *Aspergillus niger* (An_Trp2; GenBank accession number: EHA18531.1), *Aspergillus fumigatus* (Af_Trp2; GenBank accession number: KEY80754.1), and *Nicotiana tabacum* (Nt_Trp2; NCBI Reference Sequence: XP_016471994.1). The star above the sequence alignment denotes the conserved serine residue (S) which is critical for the allosteric regulation. The mutation of this amino acid results in alleviation of the allosteric regulation of the enzyme, it is S76 in *S. cerevisiae*, S83 in *A. niger*, S73 in *A. fumigatus*, and S116 in and *N. tabacum*. The sequence alignment and the identity values were determined with the Multiple Sequence Alignment tool Clustal Omega at the EMBL-EBI website (https://www.ebi.ac.uk/Tools/msa/clustalo/). Visualization of the alignment was done with the BoxShade tool at the ExPASy website (https://embnet.vital-it.ch/software/BOX_form.html).

FIG. 13 discloses a UPLC-MS analysis of the analytical standards: L-tryptophan, tryptamine, psilocybin, and psilocin. FIG. 13A discloses a table with basic characteristics of the standards: calculated molecular masses and experimentally obtained retention times. FIG. 13B discloses the UPLC chromatogram of the four compounds as detected by photodiode array (PDA) detector at 280 nm. FIG. 13C discloses the base peak intensity (BPI) chromatogram of the four compounds as detected by mass spectrometry. The shift in the retention times of each compound is caused by the positioning of the detectors (first PDA, second MS).

Figure 14A:
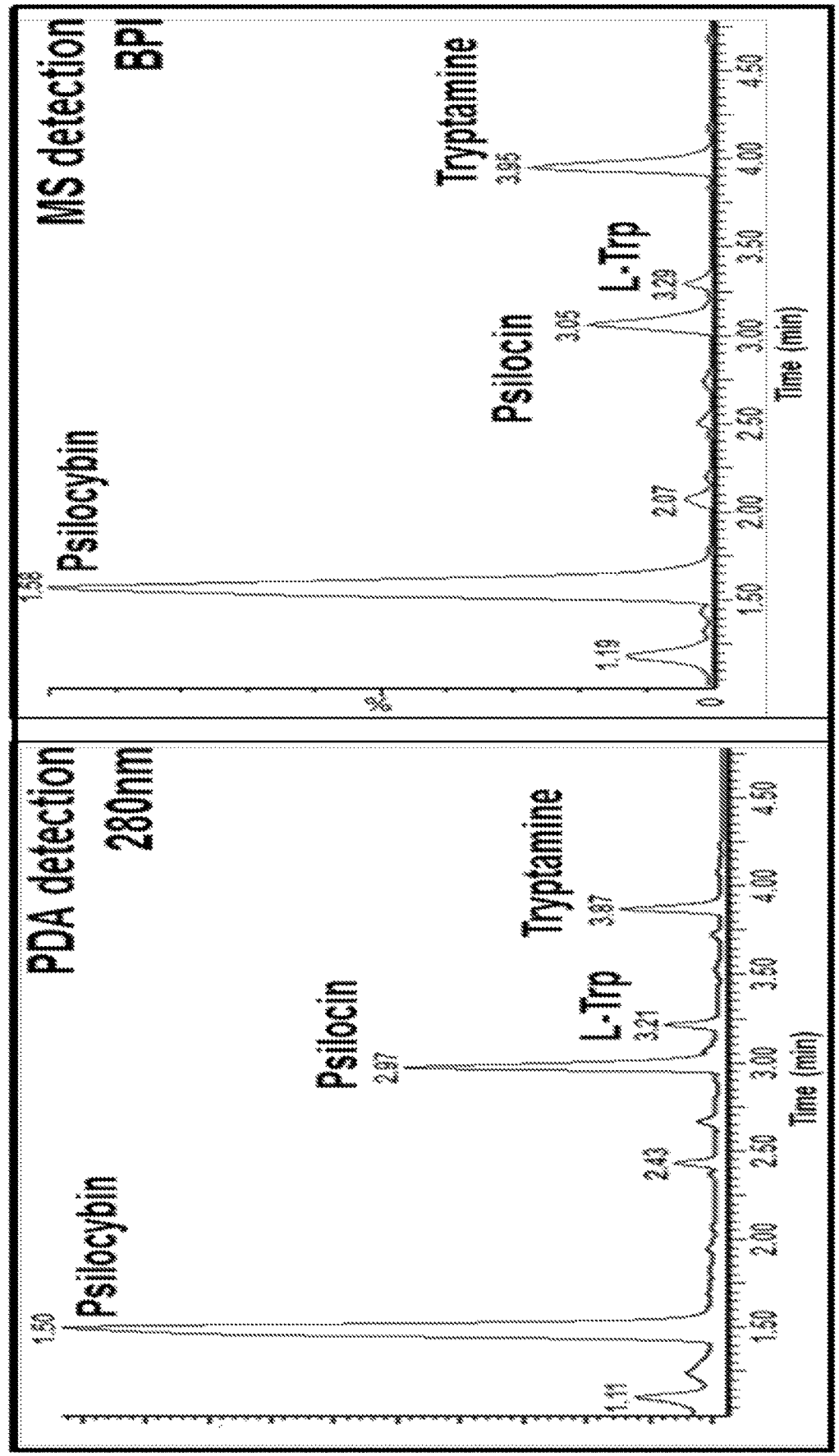
Figure 14B:
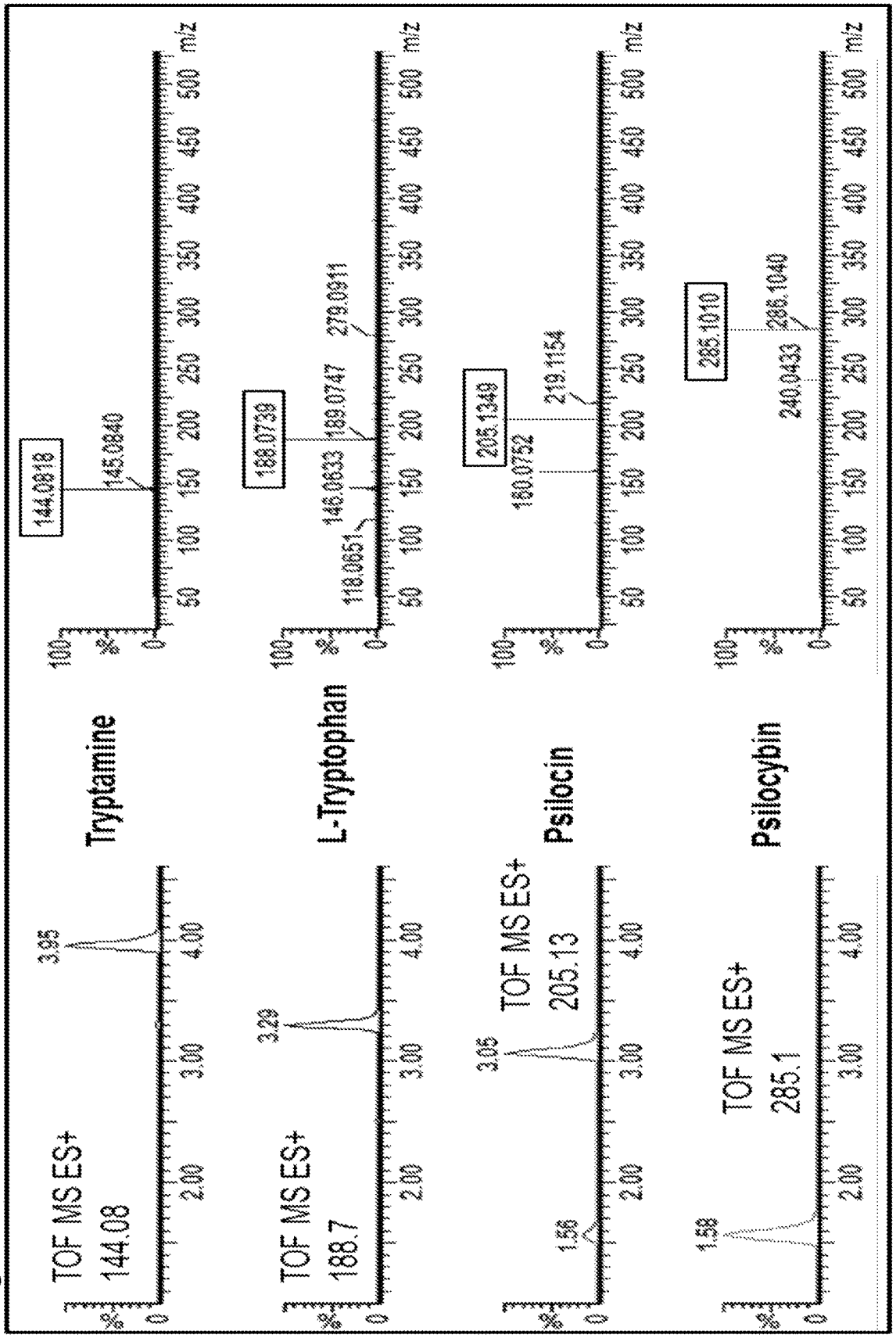

FIGS. 14A and 14B disclose an example UPLC-MS analysis of psilocybin and related compounds in the cell pellet extract from the Sc_T2M_T3 strain with implemented psilocybin pathway #6 cultivated 3 days in the YPD medium. FIG. 14A discloses the UPLC chromatograms as detected by photodiode array (PDA) detector at 280 nm (left panel), and base peak intensity (BPI) chromatogram as detected by mass spectrometry (right panel). FIG. 14B discloses the mass spectrometry confirmation of the individual compounds detected in the sample.

Figure 15A:
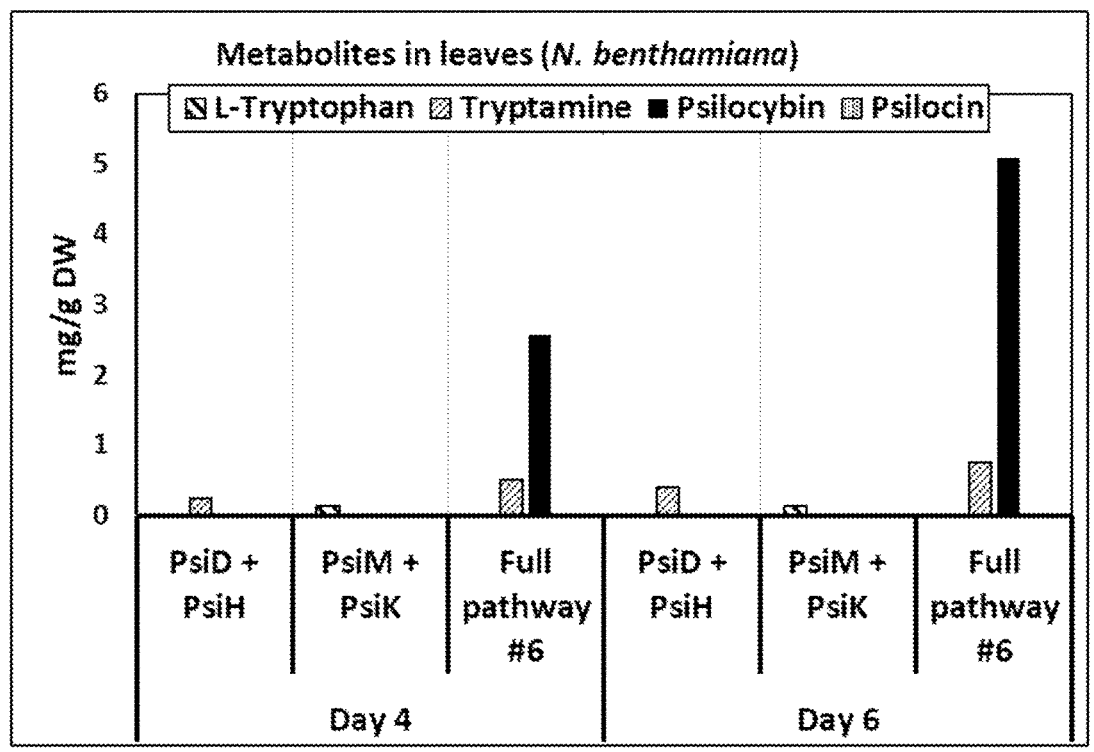
Figure 15B:
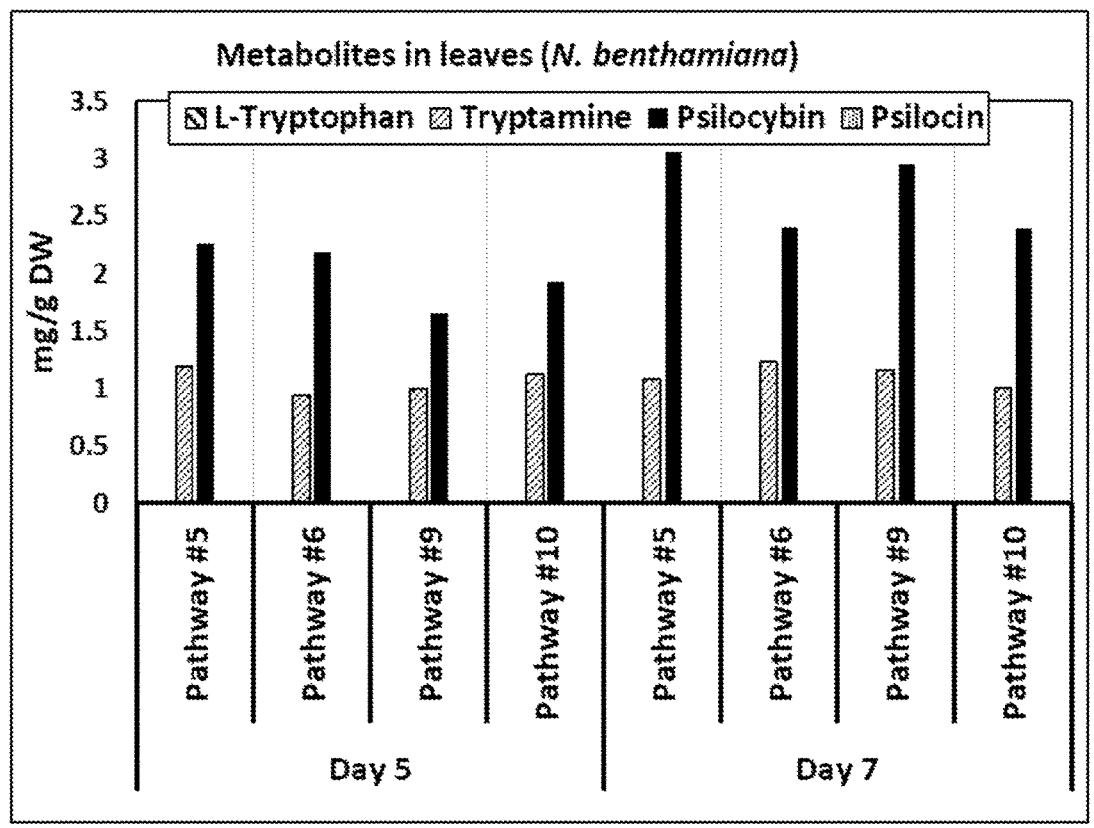

FIGS. 15A and 15B disclose results from the analysis of psilocybin and related compounds in the *Nicotiana benthamiana* leaves transiently transformed by *Agrobacterium tumefaciens* strains carrying diverse parts of the psilocybin biosynthetic pathway. FIG. 15A discloses results obtained from leaves expressing incomplete pathways and the full pathway #6. FIG. 15B discloses results obtained from leaves expressing complete pathways #5, #6, #9, and #10.

| SEQUENCE LISTINGS | | | |
|---|---|---|---|
| Sequence | Source organism | Gene name | Codons optimized for |
| SEQ ID NO: 1 | *Psilocybe cubensis* | PsiD | *Saccharomyces cerevisiae* |
| SEQ ID NO: 2 | *Psilocybe cyanescens* | PsiD | *Saccharomyces cerevisiae* |
| SEQ ID NO: 3 | *Psilocybe cubensis* | PsiM | *Saccharomyces cerevisiae* |
| SEQ ID NO: 4 | *Psilocybe cyanescens* | PsiM | *Saccharomyces cerevisiae* |
| SEQ ID NO: 5 | *Psilocybe cubensis* | PsiH | *Saccharomyces cerevisiae* |
| SEQ ID NO: 6 | *Psilocybe cyanescens* | PsiH | *Saccharomyces cerevisiae* |
| SEQ ID NO: 7 | *Psilocybe cubensis* | PsiK | *Saccharomyces cerevisiae* |
| SEQ ID NO: 8 | *Psilocybe cyanescens* | PsiK | *Saccharomyces cerevisiae* |
| SEQ ID NO: 9 | *Psilocybe cubensis* | PsiD | *Aspergillus niger* |
| SEQ ID NO: 10 | *Psilocybe cyanescens* | PsiD | *Aspergillus niger* |
| SEQ ID NO: 11 | *Psilocybe cubensis* | PsiM | *Aspergillus niger* |
| SEQ ID NO: 12 | *Psilocybe cyanescens* | PsiM | *Aspergillus niger* |
| SEQ ID NO: 13 | *Psilocybe cubensis* | PsiH | *Aspergillus niger* |
| SEQ ID NO: 14 | *Psilocybe cyanescens* | PsiH | *Aspergillus niger* |
| SEQ ID NO: 15 | *Psilocybe cubensis* | PsiK | *Aspergillus niger* |
| SEQ ID NO: 16 | *Psilocybe cyanescens* | PsiK | *Aspergillus niger* |

| Sequence | Source organism | Protein name |
|---|---|---|
| SEQ ID NO: 17 | *Saccharomyces cerevisiae* | Aro4 (K229L) |
| SEQ ID NO: 18 | *Saccharomyces cerevisiae* | Trp2 (S76L) |
| SEQ ID NO: 19 | *Aspergillus niger* | Aro4 (K219L) |
| SEQ ID NO: 20 | *Aspergillus niger* | Trp2 (S83L) |

| Sequence | Description |
|---|---|
| SEQ ID NO: 21 | synthetic promoter 2BS_114cp |
| SEQ ID NO: 22 | synthetic promoter 2BS_201cp |
| SEQ ID NO: 23 | synthetic promoter 2BS_533cp |
| SEQ ID NO: 24 | synthetic bidirectional promoter 114cp_8BS_201cp |
| SEQ ID NO: 25 | TCTP1 core promoter |

SEQ ID NO: 1 is a DNA sequence encoding the PsiD enzyme from *Psilocybe cubensis* with codons suitable for expression in an AT-rich host, such as *Saccharomyces cerevisiae*

SEQ ID NO: 2 is a DNA sequence encoding the PsiD enzyme from *Psilocybe cyanescens* with codons suitable for expression in an AT-rich host, such as *Saccharomyces cerevisiae*

SEQ ID NO: 3 is a DNA sequence encoding the PsiM enzyme from *Psilocybe cubensis* with codons suitable for expression in an AT-rich host, such as *Saccharomyces cerevisiae*

SEQ ID NO: 4 is a DNA sequence encoding the PsiM enzyme from *Psilocybe cyanescens* with codons suitable for expression in an AT-rich host, such as *Saccharomyces cerevisiae*

SEQ ID NO: 5 is a DNA sequence encoding the PsiH enzyme from *Psilocybe cubensis* with codons suitable for expression in an AT-rich host, such as *Saccharomyces cerevisiae*

SEQ ID NO: 6 is a DNA sequence encoding the PsiH enzyme from *Psilocybe cyanescens* with codons suitable for expression in an AT-rich host, such as *Saccharomyces cerevisiae*

SEQ ID NO: 7 is a DNA sequence encoding the PsiK enzyme from *Psilocybe cubensis* with codons suitable for expression in an AT-rich host, such as *Saccharomyces cerevisiae*

SEQ ID NO: 8 is a DNA sequence encoding the PsiK enzyme from *Psilocybe cyanescens* with codons suitable for expression in an AT-rich host, such as *Saccharomyces cerevisiae*

SEQ ID NO: 9 is a DNA sequence encoding the PsiD enzyme from *Psilocybe cubensis* with codons suitable for expression in a GC-rich host, such as *Aspergillus niger*

SEQ ID NO: 10 is a DNA sequence encoding the PsiD enzyme from *Psilocybe cyanescens* with codons suitable for expression in a GC-rich host, such as *Aspergillus niger*

SEQ ID NO: 11 is a DNA sequence encoding the PsiM enzyme from *Psilocybe cubensis* with codons suitable for expression in a GC-rich host, such as *Aspergillus niger*

SEQ ID NO: 12 is a DNA sequence encoding the PsiM enzyme from *Psilocybe cyanescens* with codons suitable for expression in a GC-rich host, such as *Aspergillus niger*

SEQ ID NO: 13 is a DNA sequence encoding the PsiH enzyme from *Psilocybe cubensis* with codons suitable for expression in a GC-rich host, such as *Aspergillus niger*

SEQ ID NO: 14 is a DNA sequence encoding the PsiH enzyme from *Psilocybe cyanescens* with codons suitable for expression in a GC-rich host, such as *Aspergillus niger*

SEQ ID NO: 15 is a DNA sequence encoding the PsiK enzyme from *Psilocybe cubensis* with codons suitable for expression in a GC-rich host, such as *Aspergillus niger*

SEQ ID NO: 16 is a DNA sequence encoding the PsiK enzyme from *Psilocybe cyanescens* with codons suitable for expression in a GC-rich host, such as *Aspergillus niger*

SEQ ID NO: 17 is a protein sequence of allosterically insensitive mutant of *Saccharomyces cerevisiae* Aro4 enzyme (Aro4-K229L)

SEQ ID NO: 18 is a protein sequence of allosterically insensitive mutant of *Saccharomyces cerevisiae* Trp2 enzyme (Trp2-S76L)

SEQ ID NO: 19 is a protein sequence of allosterically insensitive mutant of *Aspergillus niger* Aro4 enzyme (Aro4-K219L)

SEQ ID NO: 20 is a protein sequence of allosterically insensitive mutant of *Aspergillus niger* Trp2 enzyme (Trp2-S83L) SEQ ID NO: 21 is a DNA sequence of synthetic promoter containing two binding sites for Bm3R1-sTF and the core promoter 114cp.

SEQ ID NO: 22 is a DNA sequence of synthetic promoter containing two binding sites for Bm3R1-sTF and the core promoter 201cp SEQ ID NO: 23 is a DNA sequence of synthetic promoter containing two binding sites for Bm3R1-sTF and the core promoter 533cp SEQ ID NO: 24 is a DNA sequence of synthetic bidirectional promoter containing eight binding sites for Bm3R1-sTF flanked with core promoters (114cp and 201cp) directing the transcription to opposite directions SEQ ID NO: 25 is a DNA sequence of the *Arabidopsis thaliana* MTMC1 core promoter used for the expression of synthetic transcription in tobacco plants.

DETAILED DESCRIPTION

The present inventors have surprisingly found that synthesis of psilocybin and related compounds, such as metabolic intermediates of the psilocybin biosynthesis, can be carried out in a recombinant host cell. The inventors found that simply inserting psilocybin biosynthesis pathway genes originating from one species of a mushroom, such as either *Psilocybe cubensis* or *Psilocybe cyanescens*, in a host cell is not sufficient for obtaining an efficient production host. The inventors found that a specific combination of the genes from different mushroom species encoding the psilocybin biosynthetic pathway is required for efficient production of psilocybin and related compounds in a recombinant host cell. In addition, without being bound to any theory, it is assumed that the key metabolic substrates and some biosynthesis metabolites can be present in a host cell in amounts that limit production of psilocybin even when the enzymes of the psilocybin pathway were present in the host cell. Thus, preferably either the amount of the metabolites or the regulation of the enzymes responsible for the biosynthesis has to be modified to provide efficient production.

Preferably the host cell, to which the specific psilocybin biosynthesis pathway is engineered, is modified to have elevated L-tryptophan production capacity. Preferably this is achieved by inserting in the host cell genome genetic elements to increase expression of native genes encoding enzymes of the L-tryptophan biosynthetic pathway, and/or by inserting heterologous polynucleotides that encode selected enzymes of the L-tryptophan biosynthetic pathway.

The invention provides an efficient way to produce psilocybin and its intermediates. Because the production is carried out in a recombinant host cell, a production system is provided which can be optimized, tailored, and controlled in a desired manner. The psilocybin produced by the method can be used as such or formulated into a selected formulation. The present invention also provides efficient production of psilocybin and makes it possible to scale up the production method to an industrial scale. Further, the production of heterologous psilocybin in a recombinant host cell host, and use of large scale bioreactors or production systems provides consistent, cheap, and high level of safety production.

In an embodiment the at least one promoter provides production of the heterologous polynucleotides.

In an embodiment the at least one promoter provides constitutive production of the heterologous polynucleotides. Constitutive production is advantageous when it is desirable to express the heterologous polynucleotides without separate induction. Thus, they can be used in a production system which produces said enzymes, and metabolites produced by them, continuously. Constitutive production also helps to produce enzymes required for psilocybin biosynthesis in a concerted way, thereby simplifying production e.g. in a production system.

In an embodiment the at least one heterologous polynucleotide is operably linked to a single promoter, which controls the expression of each of PsiD, PsiH, PsiK, and PsiM.

In an embodiment the single promoter is controlled by a synthetic transcription factor. Synthetic transcription factor can be used to achieve better control of the expressed genes, instead of using natural transcription factors.

In another embodiment the single promoter comprises the SEQ ID NO: 21, 22, 23, and/or 24.

In an embodiment the host cell further comprises at least one further genetic element arranged to increase biosynthetic production of L-tryptophan in the host cell, wherein the further genetic element is operably linked to at least one promoter which is capable of directing expression of said further genetic element in the host cell.

In an embodiment the host cell comprises a modification, which is arranged to increase biosynthetic production of L-tryptophan in the host cell.

In an embodiment the further genetic element encodes at least one enzyme selected from Aro1, Aro2, Aro3, Aro4, Trp1, Trp2, Trp3, Trp4 and Trp5, or a homolog thereof. In another embodiment the homolog is an enzyme having at least 60%, such as 60%, 65%, 70%, 75%, 80%, 85%, 90%, 95%, 96%, 97%, 98%, or 99% amino acid sequence identity with the corresponding sequence of the *Saccharomyces cerevisiae* enzyme.

In an embodiment the heterologous polynucleotide is a closest homolog of a polynucleotide encoding Aro1, Aro2, Aro3, Aro4, Trp1, Trp2, Trp3, Trp4 or Trp5. The closest homolog has the highest percentage of identical nucleotides with the gene encoding the protein product above; or a gene whose protein product has the highest percentage of identical amino acids with the protein product encoded by the gene.

In an embodiment the further genetic element encodes at least one enzyme selected from Aro1, Aro2, Aro3, Aro4, Trp1, Trp2, Trp3, Trp4 and Trp5, or a homolog thereof. It is expected that an enzyme having high sequence identity inherits more likely properties of the enzyme it is compared with, which is advantageous to improve control and predictability of the metabolite production and biosynthesis regulation in the host cell, in particular in yeast host cells. However, a sequence identity of at least 60% is considered sufficient in the present invention, because the overall sequence conservation in the relevant protein family is rather low.

In a further embodiment the genetic element comprises at least one further heterologous polynucleotide.

In an embodiment the further genetic element encodes at least one of Aro3, Aro4 and Trp2, which is genetically modified to inhibit its allosteric regulation. This is advantageous to increase L-tryptophan production even further.

In an embodiment the host cell comprises at least two further genetic elements that are controlled by a single synthetic transcription factor. This has an advantage of easier control of expression.

In an embodiment the synthetic transcription factor is the same synthetic transcription factor which controls expression of the heterologous polynucleotides encoding PsiD, PsiH, PsiK and/or PsiM. This has an advantage of easier control of expression, and psilocybin production. Further, particularly when the constitutive production of the enzymes is used by using a suitable transcription factor and suitable promoter, production of each enzyme is achieved simultaneously.

Thereby, the biosynthetic pathway is reconstructed and fully operational leading to accumulation of psilocybin with simultaneous minimizing of intermediate metabolites accumulation.

In an embodiment the genetic modification comprises at least one of:
a modification of a polynucleotide encoding Trp2 with a S76 mutation, wherein the residue numbering corresponds to that of SEQ ID NO: 18 (*S. cerevisiae* Trp2), and
a modification of a polynucleotide encoding Aro4 with a K229 mutation, wherein the residue numbering corresponds to that of SEQ ID NO: 17 (*S. cerevisiae* Aro4).

These mutations are efficient to prevent allosteric regulation, without affecting negatively on the enzyme activity.

The conserved lysine residue corresponding the K229 residue of *S. cerevisiae* Aro4 is present in homologs of Aro4 enzyme in other hosts, such and *A. niger* or others (FIG. 11), where the mutation can lead to alleviation of allosteric inhibition. The conserved serine residues corresponding the S76 residue of *S. cerevisiae* Trp2 are present in homologs of Trp2 enzyme in other hosts, such as *A. niger* and others (FIG. 12), where the mutation can lead to alleviation of allosteric inhibition.

In an embodiment:
PsiD has at least 60% or 80% amino acid sequence identity with the protein sequence deposited in GenBank accession number ASU62239.1 or the GenBank accession number ASU62242.1, or with the amino acid sequence encoded by polynucleotide SEQ ID NO: 1 or 2 or 9 or 10;
PsiH has at least 60% or 80% amino acid sequence identity with the protein sequence deposited in GenBank accession number ASU62246.1 or the GenBank accession number ASU62250.1, or with the amino acid sequence encoded by polynucleotide SEQ ID NO: 5 or 6 or 13 or 14;
PsiK has at least 60% or 80% amino acid sequence identity with the protein sequence deposited in GenBank accession number ASU62237.1 or the GenBank accession number ASU62240.1, or with the amino acid sequence encoded by polynucleotide SEQ ID NO: 7 or 8 or 15 or 16;
PsiM has at least 60% or 80% amino acid sequence identity with the protein sequence deposited in GenBank accession number ASU62238.1 or the GenBank accession number ASU62241.1, or with the amino acid sequence encoded by polynucleotide SEQ ID NO: 3 or 4 or 11 or 12.

In an embodiment the further genetic element encodes at least one of:
Aro4 which has at least 60% or 80% amino acid sequence identity with SEQ ID NO: 17 or 19;
Trp2 which has at least 60% or 80% amino acid sequence identity with SEQ ID NO: 18 or 20; and
Trp3 which has at least 60% or 80% amino acid sequence identity with the sequence corresponding to the GenBank accession number CAA82056.1 or the GenBank accession number OWW28508.1

In an embodiment the recombinant host cells are supplemented with L-tryptophan.

Increased L-tryptophan availability enhance precursor supply and feeds the biosynthetic pathway towards psilocybin production.

In an embodiment L-tryptophan is supplemented by adding L-tryptophan in the growth medium wherein the recombinant host cells are cultivated.

This has an advantage that increased L-tryptophan production does not stress the host cell, because the cell can obtain it from an extracellular source.

In an embodiment in the method the recombinant host cell is the recombinant host cell of an above aspect and L-tryptophan is supplemented by initiating expression of Aro4, Trp2 and Trp3 to enhance production of L-tryptophan.

In an embodiment the method is for producing psilocybin, and psilocybin is recovered in step d.

In an embodiment at least one of the following is recovered in step d: tryptamine, 4-hydroxy-tryptamine, norbaeocystin, baeocystin, psilocybin, and psilocin.

In an embodiment the production of L-tryptophan is enhanced in the recombinant host cell or in the method by inserting in the host cell heterologous polynucleotides capable of enhancing native metabolic flux towards production of L-tryptophan.

Enhanced L-tryptophan production has an advantage of providing higher intracellular concentration of L-tryptophan, which enhances production of psilocybin as the end product of the biosynthetic pathway.

In an embodiment the production of L-tryptophan is enhanced by inserting in the host cell at least one heterologous polynucleotide encoding allosterically insensitive Aro4 enzyme operably linked to an artificial promoter.

In an embodiment the production of L-tryptophan is enhanced by inserting in the host cell at least one heterologous polynucleotide encoding allosterically insensitive Trp2 enzyme operably linked to an artificial promoter.

In an embodiment the production of L-tryptophan is enhanced by inserting in the host cell at least one heterologous polynucleotide encoding allosterically insensitive Trp2 enzyme, and encoding Trp3 enzyme, operably linked to an artificial promoter.

In an embodiment the production of L-tryptophan is enhanced by inserting in the host cell at least one heterologous polynucleotide encoding allosterically insensitive Aro4 and Trp2 enzyme, and a polynucleotide encoding Trp3 enzyme operably linked to an artificial promoter.

In an embodiment the insertion is by integrating into the genome of the host cell.

In an embodiment the artificial promoter is a promoter activated by a synthetic transcription factor, sTF.

In an embodiment the sTF comprises a polynucleotide encoding:
 a fusion protein composed of the Bm3R1 coding region (NCBI Reference Sequence: WP_013083972.1), SV40 nuclear localization signal, and the transcription activation domain VP16; and
 a core promoter, which provides expression of the sTF polynucleotide.

In an embodiment the sTF is integrated in the genome of the host cell. This can be achieved by transformation with a cassette, which contains the sTF polynucleotide.

In addition to the above mentioned approaches to elevate metabolic flux in the L-tryptophan biosynthesis, other methods can be used either alone or in combinations. Suitable methods include modification of the upstream metabolism increasing provision of pathway's essential precursors and/or cofactors, such as PEP, E4P, L-glutamine (L-Gln as a donor of amino-group in the Trp2/Trp3 reaction). In an embodiment other genes encoding enzymes in the shikimate or L-tryptophan pathways, such as Aro1, Aro2, or Trp5, are overexpressed to drive the metabolic flux towards L-tryptophan.

Further, elimination of certain reactions, such as metabolic branches towards L-tyrosine and L-phenylalanine, or degradation pathway of L-tryptophan, can also be exploited to increase the L-tryptophan levels available for psilocybin biosynthesis. The skilled person is able to achieve said eliminations e.g. by disrupting at least partially genes encoding essential enzymes in said branches of the metabolic pathways, such as Aro7, Aro8, Aro9, or Aro10 in *S. cerevisiae* or their homologs in other organisms, such as *A. niger*.

In an embodiment the PsiD belongs to the PLP-independent phosphatidylserine decarboxylase family (E.C. 4.1.1.65). In an embodiment the PsiD of the invention has at least 80% sequence identity with the sequence corresponding to the GenBank accession number ASU62239.1 or the GenBank accession number ASU62242.1, or with the amino acid sequence encoded by polynucleotide SEQ ID NO: 1 or 2 or 9 or 10.

In an embodiment the PsiH is a monooxygenase. In an embodiment the PsiH of the invention has at least 80% sequence identity with the sequence corresponding to the GenBank accession number ASU62246.1 or the GenBank accession number ASU62250.1, or with the amino acid sequence encoded by polynucleotide SEQ ID NO: 5 or 6 or 13 or 14.

In an embodiment the PsiK is a 5-methylthioribose family of small-molecule kinases. In an embodiment the PsiK of the invention has at least 80% sequence identity with the sequence corresponding to the GenBank accession number ASU62237.1 or the GenBank accession number ASU62240.1, or with the amino acid sequence encoded by polynucleotide SEQ ID NO: 7 or 8 or 15 or 16.

In an embodiment the PsiM is a class I methyltransferase. In an embodiment the PsiM of the invention has at least 80% sequence identity with the sequence corresponding to the GenBank accession number ASU62238.1 or the GenBank accession number ASU62241.1, or with the amino acid sequence encoded by polynucleotide SEQ ID NO: 3 or 4 or 11 or 12.

In an embodiment the host cell comprises heterologous polynucleotides encoding PsiD, PsiH, PsiK, and PsiM, which form the whole psilocybin pathway.

In an embodiment the psilocybin pathway (PsiD, PsiH, PsiK, and PsiM) is composed by any combination of the corresponding polynucleotides SEQ ID NO: 1-16.

In a preferred embodiment the psilocybin pathway is composed of PsiD of *Psilocybe cubensis* origin (encoded by polynucleotide SEQ ID NO: 1 or 9), PsiH of *Psilocybe cyanescens* origin (encoded by polynucleotide SEQ ID NO: 6 or 14), PsiK of *Psilocybe cyanescens* origin (encoded by polynucleotide SEQ ID NO: 8 or 16), and PsiM of *Psilocybe cubensis* origin (encoded by polynucleotide SEQ ID NO: 3 or 11).

In another preferred embodiment the psilocybin pathway is composed of PsiD of *Psilocybe cubensis* origin (encoded by polynucleotide SEQ ID NO: 1 or 9), PsiH of *Psilocybe cyanescens* origin (encoded by polynucleotide SEQ ID NO: 6 or 14), PsiK of *Psilocybe cubensis* origin (encoded by polynucleotide SEQ ID NO: 7 or 15), and PsiM of *Psilocybe cyanescens* origin (encoded by polynucleotide SEQ ID NO: 4 or 12).

In another preferred embodiment the psilocybin pathway is composed of PsiD of *Psilocybe cyanescens* origin (encoded by polynucleotide SEQ ID NO: 2 or 10), PsiH of *Psilocybe cyanescens* origin (encoded by polynucleotide SEQ ID NO: 6 or 14), PsiK of *Psilocybe cubensis* origin (encoded by polynucleotide SEQ ID NO: 7 or 15), and PsiM of *Psilocybe cubensis* origin (encoded by polynucleotide SEQ ID NO: 3 or 11).

In an embodiment the Aro4 is a 3-deoxy-D-arabino-heptulosonate 7-phosphate (DAHP) synthase. In an embodiment the Aro4 of the invention contains lysine-to-leucine mutation in position 229 (*S. cerevisiae* version K229L), or lysine-to-leucine mutation in position 219 (*A. niger* version K219L), which causes alleviation of feedback-inhibition. Lysine-to-leucine mutations can be implemented to other homologs of Aro4 to generate allosterically insensitive DAHP synthase enzymes in other hosts (FIG. 11). In an embodiment the Aro4 of the invention has at least 80% sequence identity with the sequence corresponding to the SEQ ID NO: 17 (*S. cerevisiae* version) or SEQ ID NO: 19 (*A. niger* version).

In an embodiment the Trp2 is an anthranilate synthase. In an embodiment the Trp2 of the invention contains serine-to-leucine mutation in position 76 (*S. cerevisiae* version S76L), or serine-to-leucine mutation in position 83 (*A. niger* version S83L), which causes alleviation of feedback-inhibition. Serine-to-leucine mutation can be also implemented to other homologs of Trp2 to generate allosterically insensitive anthranilate synthase enzymes in other hosts (FIG. 12). In an embodiment the Trp2 of the invention has at least 80% sequence identity with the sequence corresponding to the SEQ ID NO: 18 (*S. cerevisiae* version) or SEQ ID NO: 20 (*A. niger* version).

In an embodiment the Trp3 is an indole-3-glycerol-phosphate synthase involved in L-tryptophan biosynthesis. In an embodiment the Trp3 of the invention has at least 80% sequence identity with the sequence corresponding to the GenBank accession number CAA82056.1 or the GenBank accession number OWW28508.1.

In an embodiment the terms PsiD, PsiH, PsiK, and PsiM refer to polypeptides having the corresponding enzyme activity of the relevant enzyme in psilocybin production host, as well as to fusion proteins comprising them. The polypeptides do not necessarily have the exact amino acid sequence of the relevant enzyme, and they may contain mutations, substitutions, additions, deletions and posttranslational modifications that make them chemically and/or functionally different compared to the same enzymes produced in their native host cell.

In an embodiment the recombinant host cell is a eukaryotic host cell selected from the group consisting of plant cell, animal cell, or fungal cell.

In a preferred embodiment the recombinant host cell is a recombinant plant cell or a recombinant yeast cell.

In an embodiment is provided a plant or a plant part comprising at least recombinant plant cell of the invention. Preferably the plant is a tobacco plant.

In certain embodiments, the heterologous polynucleotides, e.g. in a form of a construct containing them, may be introduced in the genome of a host cell (e.g., of the plant) in which the polynucleotides are expressed. The polynucleotides as taught herein can be transiently introduced in the cell (e.g., of the plant) in which the polynucleotides as taught herein are expressed, or they can be stably introduced in the genome of the cell (e.g., of the plant) in which the polynucleotides as taught herein are expressed. The polynucleotides can be introduced in the cell with methods known in the art, such as transformation or agroinfiltration. The polynucleotides according to the invention may be inserted into vectors, which may be commercially available, suitable for transforming into plants and suitable for (transiently or stably) expressing of the gene of interest in the transformed cells.

In a preferred embodiment the heterologous polynucleotides are transferred to plant host cells by agroinfiltration for transient expression of the heterologous polynucleotides.

In an embodiment is provided a method for the production of a plant having a capability to produce psilocybin comprising:
(i) Introducing and expressing in said plant, or in a plant cell thereof, a heterologous polynucleotides encoding PsiD, PsiH, PsiK, and PsiM, wherein the heterologous polynucleotides are operably linked to at least one promoter which is capable of directing expression of said heterologous polynucleotides in the host cell; and
(ii) Cultivating said plant or said plant cell under conditions promoting plant growth and development.

The term "plant" as used throughout the specification encompasses whole plants, ancestors and progeny of the plants and plant parts, including seeds, shoots, stems, leaves, roots (including tubers), flowers, and tissues and organs, wherein each of the aforementioned comprise the polynucleotide of interest. In certain embodiments, the term "plant" also encompasses plant cells, suspension cultures, callus tissue, embryos, meristematic regions, gametophytes, sporophytes, pollen and microspores, again wherein each of the aforementioned comprises the polynucleotide and construct of interest.

In an embodiment the method comprises introducing the heterologous polynucleotides encoding PsiD, PsiH, PsiK and PsiM in the plant by agroinfiltration by using two *Agrobacterium* strains, each containing two of said polynucleotides. In a further embodiment the plant cell is exposed to the *Agrobacterium* strains sequentially. In another embodiment the plant cell is exposed to a mixture containing both *Agrobacterium* strains.

The skilled person is able to analyse the amount of metabolite produced by the present method by using a method known in the art. In an embodiment the level of metabolite is analysed as described in Example 3. Preferably the analysis is by methanol extraction and UPLC-MS analysis.

In an embodiment the recombinant host cell is selected from cells of: 1) Fungal microorganisms including filamentous fungi and yeasts, in particular organisms from the following taxa: A) Saccharomycetales, including but not limited to species *Saccharomyces cerevisiae, Kluyveromyces lactis, Candida krusei (Pichia kudriavzevii), Pichia pastoris (Komagataella pastoris), Eremothecium gossypii, Kazachstania exigua, Yarrowia lipolytica*, and others; Schizosaccharomycetes, such as *Schizosaccharomyces pombe*; B) Eurotiomycetes, including but not limited to species *Aspergillus niger, Aspergillus nidulans, Penicillium chrysogenum*, and others; C) Sordariomycetes, including but not limited to species *Trichoderma reesei, Myceliophthora thermophila*, and others; D) Mucorales, such as *Mucor indicus* and others. 2) Plant organisms, including flowering plants and green algae, in particular organisms from the following taxa: E) Solanales, including but not limited to species *Nicotiana benthamiana, Solanum tuberosum, Lycopersicon esculentum, Capsicum anuum*, and others; F) Brassicales, including but not limited to species *Arabidopsis thaliana, Brassica napus*, and others; G) Poales, including but not limited to species *Avena sativa, Secale cereale, Zea mays, Triticum* spp., *Oryza sativa, Hordeum vulgare, Sorghum bicolor, Saccharum officinarum*, and others; H) Fabales including but not limited to species *Phaseolus* spp., *Vigna* spp., *Glycine max, Pisum sativum, Lens culinaris, Cicer arietinum* and others; I) Malpighiales, including but not limited to species *Populus* sp., and others; J) Pinales, including but not limited to species *Pinus* sp., and others; K) Arecales including but not limited to species *Elaeis guineensis, Cocos nucifera*, and others; L) Chlorophyceae, including but not limited to species *Chlamydomonas reinhardtii*, and others; M) Trebouxiophyceae, including but not limited to species *Chlorella* spp., and others. 3) Animal organisms, in particular organisms from the following taxa: N) mammals (Mammalia), including but not limited to species *Mus musculus* (mouse), *Cricetulus griseus* (hamster), *Homo sapiens* (human), and others; O) insects (Insecta), including but not limited to species *Mamestra brassicae, Spodoptera frugiperda, Trichoplusia ni, Drosophila melanogaster*, and others.

In an embodiment the heterologous polynucleotides are integrated in the genome of the recombinant host cell.

In an embodiment the integration is by transformation of the DNA into the cell.

Transformation of (typically) yeast can be done by a "standard Lithium-acetate protocol". In case of filamentous fungi (and also yeast), protoplast transformation can be used. The protoplast transformation is described in WO2017144777. There are other ways how to get the DNA into the host: *Agrobacterium*-facilitated transfection (mainly for plants but also fungi); biolistic; virus-facilitated transfection; or standard chemical transfection of animal cells (other methods listed in wikipedia: https://en.wikipedia.org/wiki/Transfection)

In an embodiment the integration is by integration of the (intracellular) DNA into the genome. Integration of the DNA into specific place (locus) in the genome can be done by the intrinsic cellular mechanism—homologous recombination (or sometimes by non-homologous recombination which however results in random/unspecific integration). The integration into a specific place of the genome can be achieved by homologous recombination providing, in the transformed DNA, flanking sequences identical/homologous to the genomic site of intended integration. The efficiency of the targeted genome integration can be greatly enhanced by using the CRISPR genome editing method that is based on the use of RNA-guided DNA endonucleases. There are several alternative approaches to implement the CRISPR method—there are also a few alternative RNA-guided DNA endonucleases (e.g. Cas9, Cpf1 and MAD7) which can be used in the CRISPR method. The RNA-guided DNA endonucleases can be delivered into the cells as plasmid expressing the endonuclease, or directly as a protein. The RNA-guided DNA endonucleases need a target specific guide RNA (gRNA) to generate a double stranded break into the genomic target/locus—the gRNA can be delivered as plasmid expressing the gRNA, or directly as chemically synthesized gRNA.

In an embodiment the heterologous polynucleotides are inside the recombinant host cell in at least one vector or plasmid or linear DNA molecule or DNA cassette.

In an embodiment the recombinant host cell comprises metabolites of the biosynthetic pathway from L-tryptophan to psilocybin.

In an embodiment the host cell is arranged to produce the synthetic transcription factor (sTF) constitutively.

In an embodiment the Psi genes are under the control of the synthetic transcription factor.

In an embodiment the host cell contains the Psi genes arranged in a bi-directional dual gene expression cassette. This allows co-expression of two genes from one genomic locus. In an embodiment the Psi genes are present in said cassettes in pairs PsiH and PsiD, and PsiK and PsiM.

In an embodiment the bi-directional dual gene expression cassette is used where any combination of genes in the bidirectional cassettes can be used.

In an embodiment the use of standard expression cassettes (one promoter—one gene) is used, where these cassettes:
can be integrated individually in the genome to 4 different loci
can be fused together in any combination and integrated in the genome
contain promoters used for the Psi genes which can be native, heterologous, or synthetic/artificial.

In an embodiment expression of the bi-directional dual gene expression cassette is regulated by at least one sTF-specific binding site between the outwards oriented core promoters and the polynucleotide sequences encoding Psi genes. Preferably more than one, such as 2,3,4,5,6,7,8,9, or 10 binding sites are provided. The production level of the heterologous protein encoded by the polynucleotide sequence can be controlled by the number of binding sites: fewer binding sites provide lower expression level and thus lower production, whereas a higher amount of binding sites provides higher expression level and thus higher production. The skilled person is able to select an appropriate number of binding sites to provide a suitable balance in the expression level of the heterologous proteins, which provides successful production of psilocybin or its biosynthetic intermediates.

In an embodiment the host cell contains the heterologous polynucleotides inserted in its genome in cassettes comprising at the least transcription factor and the Psi genes, and optionally L-Trp genes.

In an embodiment the host cell is genetically modified to overproduce chorismate at levels higher than the wild type host cell in the same culturing conditions. This provides a higher availability of chorismate for the L-tryptophan biosynthetic pathway, and results in higher psilocybin production.

In an embodiment the enhanced chorismate production is provided by genetically modifying at last one of the genes encoding Aro4 and/or Aro3 enzyme to prevent allosteric regulation of said enzyme. In an embodiment the genetic modification provides K229 mutation in the Aro4 enzyme. In a preferred embodiment the genetic modification provides K229L mutation in the Aro4 enzyme. In another embodiment the genetic modification provides other mutation or mutations in Aro4 or Aro3 enzymes preventing allosteric inhibition. Each of these mutations is particularly useful because they allow removing allosteric regulation of the enzyme in a single amino acid mutation or in combination of amino acid mutations.

In an embodiment the host cell is arranged to have enhanced metabolic activity in the shikimate pathway. This is advantageous in providing enhanced production of chorismate, which may be used in synthesis of further aromatic metabolites, such as L-tryptophan.

In an embodiment the host cell produces elevated amounts of Aro1 and Aro2 enzymes. In an embodiment the host cell comprises heterologous polynucleotides encoding Aro1 and/or Aro2.

In an embodiment the host cell is genetically modified to produce Trp2 and Trp3. In a preferred embodiment the host cell is genetically engineered to overexpress Trp2 and/or Trp3. Overexpression of these genes drives the metabolic flux towards L-tryptophan.

In a preferred embodiment the gene encoding Trp2 is genetically modified to prevent allosteric regulation of Trp2. In an embodiment the genetic modification provides S76 mutation in the Trp2 enzyme. In a more preferred embodiment the genetic modification provides S76L mutation in the Trp2 enzyme. This mutation is particularly useful because it allows removing allosteric regulation of the enzyme in a single amino acid mutation, and drives the metabolic flux even more efficiently towards L-tryptophan.

In an embodiment the host cell comprises genes encoding Trp4, Trp1, Trp3, Trp5 and Trp2. In another embodiment the host cells contains heterologous polynucleotide encoding Trp1 and Trp3 in a fusion protein.

In an embodiment the host cell comprises heterologous polynucleotides encoding Aro4, Trp2 and Trp3. In a preferred embodiment the polynucleotides encoding Aro4 and Trp2 are genetically modified to prevent allosteric regulation of said enzymes. Preferably said genetic modification comprises at least K229 mutation in Aro4 and S76 mutation in Trp2, wherein the numbering corresponds to the SEQ ID NOs: 17 and 18, respectively. More preferably said genetic modification comprises at least K229L mutation in Aro4 and S76L mutation in Trp2, wherein the numbering corresponds to the SEQ ID NOs: 17 and 18, respectively.

Even more preferably said mutation is a non-conservative mutation, most preferably a mutation into L residue.

In an embodiment the method and the production system is an industrial scale method and an industrial scale production system.

In an embodiment the heterologous polynucleotides are under control of the same transcription factor of transcription factors.

In an embodiment the heterologous polynucleotides of the psilocybin pathway are under control of the same transcription factor or transcription factors, and the heterologous polynucleotides responsible for the enhanced L-tryptophan production are under control of a different transcription factor or factors. In an embodiment the transcription factor or transcription factors provide constitutive production of the transcription factor. In another embodiment the production of the transcription factor is triggered by an effector molecule.

The recombinant host cell can be used to produce psilocybin and to carry the heterologous polynucleotides required for synthesis of psilocybin from L-tryptophan. The recombinant host cell is useful also in optimization of L-tryptophan and/or psilocybin production. For example, a host cell can be selected, which facilitates purification and formulation of psilocybin produced in the host cell.

The polypeptide encoded by the heterologous polynucleotide may have structural or functional properties that differentiate it from a native polypeptide having the same or similar amino acid sequence. For example, a host cell can be selected for production, which provides the produced recombinant polypeptide with post-translational modifications, a lack thereof, or localization to facilitate production and/or formulation.

In an embodiment in the method the recombinant host cells are supplemented with L-tryptophan. This has an advantage of enhanced production of psilocybin and its synthesis intermediates.

In an embodiment in the method at least two metabolites are recovered.

In one embodiment of the invention the heterologous polynucleotide encodes an enzyme having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the PsiD amino acid sequence encoded by polynucleotide SEQ ID NO: 1 or 2 or 9 or 10.

In one embodiment of the invention the heterologous polynucleotide encodes an enzyme having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the PsiH amino acid sequence encoded by polynucleotide SEQ ID NO: 5 or 6 or 13 or 14.

In one embodiment of the invention the heterologous polynucleotide encodes an enzyme having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the PsiK amino acid sequence encoded by polynucleotide SEQ ID NO: 7 or 8 or 15 or 16.

In one embodiment of the invention the heterologous polynucleotide encodes an enzyme having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the PsiM amino acid sequence encoded by polynucleotide SEQ ID NO: 3 or 4 or 11 or 12.

In one embodiment of the invention the heterologous polynucleotide encodes an enzyme having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to ARO4, SEQ ID NO: 17 or 19.

In one embodiment of the invention the heterologous polynucleotide encodes an enzyme having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to TRP2, SEQ ID NO: 18 or 20.

In one embodiment of the invention the heterologous polynucleotide encodes an enzyme having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to TRP3 amino acid sequence deposited in the GenBank under accession number CAA82056.1 or the GenBank accession number OWW28508.1.

In an embodiment the heterologous polynucleotide does not have 100% sequence identity with any one of PsiD, PsiH, PsiK, PsiM, ARO4, TRP2 and/or TRP3 at nucleotide sequence level or amino acid sequence level.

In another embodiment of the invention the heterologous polynucleotide encodes an amino acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to at least one of the sequences of PsiD, PsiH, PsiK, PsiM, ARO4, TRP2 and TRP3.

In an embodiment the heterologous polynucleotide encodes an active fragment of any of the enzymes encoded by the Psi genes, and/or the enzymes encoded by the L-Trp genes.

An advantage of a certain sequence identity or similarity as defined above is that the an enzyme having said sequence identity can comprise modification, in view of the original sequence, which improves controlling production of psilocybin, or improves production yield or simplifies the production process.

In an embodiment the production system of the third aspect is configured to carry out the method of the second aspect. Thus, the production system can be advantageously used to produce metabolites, including psilocybin.

In an embodiment the production unit is a fermenter. Preferably the present recombinant host cell is provided inside the reactor tank of the fermenter.

In an embodiment the production unit comprises at least one fluid inlet and at least one fluid outlet, each fluid inlet and fluid outlet being in fluid connection with at least one vessel.

In an embodiment the production unit comprises temperature controlling means for lowering and raising temperature of the production unit.

In an embodiment the control unit is configured to monitor and control cultivation of the recombinant host cells such that constitutive production of recombinant enzymes is achieved.

In an embodiment the control unit is configured to control operation of the temperature controlling means and the at least one fluid inlet and at least one fluid outlet.

As evidenced by the Examples, the recombinant host cell according to the invention allows production of psilocybin and its intermediates in a recombinant host cell. The inventors tested several heterologous polynucleotides and their variants and found that not all of them produce sufficient yields, or have the required stability or activity, which allows them to be taken into use in industrial production. Thus, the invention described above defines a limited set of host cells that can be used in production of psilocybin and its intermediates. The host cell of the present invention is particularly suitable for production in a yeast host cell or a filamentous fungus host cell.

A common structural element shared by the host cells of the invention is the combination of the heterologous polynucleotides encoding PsiD, PsiH, PsiK, and PsiM. These structural elements are characteristic for the host cell of the invention.

The term "Psi genes" refers to the genes encoding PsiD, PsiH, PsiK, and PsiM.

The term "Psi enzymes" refers to the enzymes PsiD, PsiH, PsiK, and PsiM.

The term "L-Trp genes" refers to the genes encoding Aro1, Aro2, Aro3, Aro4, Trp1, Trp2, Trp3, Trp4, and Trp5.

As used herein, "isolated" and "recovered" mean a substance in a form or environment that does not occur in nature. Non-limiting examples of isolated substances include (1) any non-naturally occurring substance, (2) any substance including any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing or decreasing the amount of the substance relative to other components with which it is naturally associated (e.g., recombinant production in a host cell; one or multiple copies of a gene; and use of an alternative promoter to the promoter naturally associated with the gene). In an embodiment a polypeptide, enzyme, polynucleotide, host cell, a metabolite or composition of the invention is isolated.

As used herein, the term "comprising" includes the broader meanings of "including", "containing", and "comprehending", as well as the narrower expressions "consisting of" and "consisting only of".

The term "substantially" when used together with a numerical parameter means an approximation of said parameter. In other words the exact mathematical value of the parameter is not in this case critical, but a certain degree of approximation is allowable and the parameter still achieves its purpose in a sufficient degree. Depending on the case, in an embodiment the term substantially allows 15%, 10% or 5% variation in the value of the parameter. In another embodiment the allowable variation is 3%, 2% or 1%.

In an embodiment the meaning of all numerical values and parameters disclosed herein include the meaning of the substantially same value as the exact mathematical value.

As used herein, "fragment" means a protein or a polynucleotide having one or more amino acids or nucleotides deleted. In the context of DNA, a fragment includes both single stranded and double stranded DNA of any length. A fragment may be an active fragment, which has the biological function, such as enzyme activity or regulatory activity, of the protein or the polynucleotide. A fragment may also be an inactive fragment, i.e. it does not have one or more biological effects of the native protein or polynucleotide.

As used herein, a "peptide" and a "polypeptide" are amino acid sequences including a plurality of consecutive polymerized amino acid residues. For purpose of this invention, peptides are molecules including up to 20 amino acid residues, and polypeptides include more than 20 amino acid residues. The peptide or polypeptide may include modified amino acid residues, naturally occurring amino acid residues not encoded by a codon, and non-naturally occurring amino acid residues. As used herein, a "protein" may refer to a peptide or a polypeptide of any size. A protein may be an enzyme, a protein, an antibody, a membrane protein, a peptide hormone, regulator, or any other protein.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

As used herein, "modification", "modified", and similar terms in the context of polynucleotides refer to modification in a coding or a non-coding region of the polynucleotide, such as a regulatory sequence, 5' untranslated region, 3' untranslated region, up-regulating genetic element, down-regulating genetic element, enhancer, suppressor, promoter, exon, or intron region. The modification may in some embodiments be only structural, having no effect on the biological effect, action or function of the polynucleotide. In other embodiments the modification is a structural modification, which provides a change in the biological effect, action or function of the polynucleotide. Such a modification may enhance, suppress or change the biological function of the polynucleotide. In an embodiment the polynucleotide is codon optimised for a host cell.

As used herein, "identity" means the percentage of exact matches of nucleotide or amino acid residues between two aligned sequences over the number of positions where there are residues present in both sequences. When one sequence has a residue with no corresponding residue in the other sequence, the alignment program allows a gap in the alignment, and that position is not counted in the denominator of the identity calculation. In an embodiment identity is a value determined with the Pairwise Sequence Alignment tool EMBOSS Needle at the EMBL-EBI websites (https://www.ebi.ac.uk/Tools/psa/emboss_needle/, https://www.ebi.ac.uk/Tools/psa/emboss_needle/nucleotide.html). In an embodiment identity is a value determined with the Multiple Sequence Alignment tool Clustal Omega at the EMBL-EBI website (https://www.ebi.ac.uk/Tools/msa/clustalo/).

As used herein, "a genetic element" means any functional polynucleotide sequence. In an embodiment a genetic element is a gene. In another embodiment a genetic element is a polynucleotide encoding an enzyme or protein, and at least one regulatory sequence such as a promoter. In another embodiment a genetic element is a polynucleotide encoding a modified enzyme or a protein and at least one regulatory sequence such as a promoter. The polynucleotide may be a heterologous polynucleotide.

As used herein the term "allosteric regulation" is the regulation of an enzyme by binding an effector molecule, such as a metabolite, at a site other than the enzyme's active site. In an embodiment the effector molecule is a metabolite downstream of the metabolic pathway.

As used herein, "host cell" means any cell type that is susceptible to transformation, transfection, transduction, mating, crossing or the like with a nucleic acid construct or expression vector comprising a polynucleotide. The term "host cell" encompasses any progeny that is not identical due to mutations that occur during replication.

A "recombinant cell" or "recombinant host cell" refers to a cell or host cell that has been genetically modified or altered to comprise a nucleic acid sequence which is not native to said cell or host cell. In an embodiment the genetic modification comprises integrating the polynucleotide in the genome of the host cell. In another embodiment the polynucleotide is exogenous in the host cell.

As used herein, "conservative amino acid substitution" is one in which the amino acid residue is replaced with an amino acid residue having a similar side chain. Families of amino acid residues having similar side chains have been defined in the art. In an embodiment the conservative amino acids in the present description refer to the amino acids within following groupings: Hydrophobic (F W Y H K M I L V A G C); Aromatic (F W Y H); Aliphatic (I L V); Polar (W Y H K R E D C S T N Q); Charged (H K R E D); Positively charged (H K R); Negatively charged (E D); Small (V C A G S P T N D); Tiny (A G S). Thus, a conservative substitution occurs when an amino acid is substituted with an amino acid in the same group.

In an embodiment the substitution is a substitution, or a structural change caused by genetic modification, affecting at least one amino acid residue. In a further embodiment the at least amino acid is Ala or Leu, preferably Leu.

As used herein, a "non-conservative amino acid substitution" is one in which an amino acid is substituted with an amino acid in a different group as defined above. The non-conservative substitution may result into a change of an amino acid to another amino acid with different biochemical properties, such as charge, hydrophobicity and/or size. In an embodiment the non-conservative substitution changes at least one property of the variant, such as stability, glycosylation pattern, folding, structure, activity, allosteric regulation or affinity.

In an embodiment any specific mutation or genetic modification described herein, such as S76L or K229L, is carried out in an alternative embodiment by using a non-conservative amino acid substitution.

As used herein, "expression" includes any step involved in the production of a polypeptide in a host cell including, but not limited to, transcription, translation, post-translational modification, and secretion. Expression may be followed by harvesting, i.e. recovering, the host cells or the expressed product, or a product produced by the activity of the expressed product.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, carrier and the like. Expression vectors are generally derived from plasmid or viral DNA, or may contain elements of both. The expression vector may be any expression vector that is conveniently subjected to recombinant DNA procedures, and the choice of vector will often depend on the host cell into which the vector is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant produced" or "recombinantly produced" used herein in connection with production of a polypeptide or metabolite is defined according to the standard definition in the art.

The term "operably linked", when referring to DNA segments or genetic elements, denotes that the segments or genetic elements are arranged so that they function in concert for their intended purposes, e.g. transcription initiates in the promoter and proceeds through the coding segment to the terminator.

The term "promoter" denotes a portion of a gene containing DNA sequences that provide for the binding of RNA polymerase and initiation of transcription. Promoter sequences are commonly, but not always, found in the 5' non-coding regions of genes. In an embodiment at least one promoter of the recombinant polypeptide or an enzyme used to increase production of L-tryptophan is under control of a synthetic promoter disclosed in WO2017144777.

The term "secretory signal sequence" denotes a DNA sequence that encodes a polypeptide (a "secretory peptide") that, as a component of a larger polypeptide, directs the larger polypeptide through a secretory pathway of a host cell in which it is produced. The secretory signal sequence can be native or it can be replaced with secretory signal sequence or carrier sequence from another source. Depending on the host cell, the larger peptide may be cleaved to remove the secretory peptide during transit through the secretory pathway. In an embodiment the heterologous polynucleotides comprise secretory signal sequences for transport into extracellular space.

"Enzyme activity" as used herein refers to the enzymatic activity of a polypeptide.

The amino acid sequence encoded by the heterologous polynucleotide may be connected to another functionality of a fusion protein via a linker sequence.

Fusion proteins can be engineered to modify properties or production of the recombinant polypeptides. In an embodiment the recombinant polypeptides are connected to each other with a linker.

By the term "linker" or "spacer" is meant a polypeptide comprising at least two amino acids which may be present between the domains of a multidomain protein, or between different domains of a fusion protein.

EXAMPLES

The following examples are provided to illustrate various aspects of the present invention. They are not intended to limit the invention, which is defined by the accompanying claims.

Example 1—Construction of *Saccharomyces cerevisiae* Platform Strains with Elevated Metabolic Flux Towards L-Tryptophan The expression cassette for the sTF (FIG. 4) contained the *S. cerevisiae* TDH3 core promoter (cp #0) and the URA3 terminator (term #0). The sTF gene was encoding a fusion protein composed of the Bm3R1 coding region (NCBI Reference Sequence: WP_013083972.1), SV40 NLS, and the transcription activation domain VP16. This cassette was integrated into the ura2-52 locus of the parental strain—*Saccharomyces cerevisiae* CEN.PK (MATα, ura3-52 leu2-3_112 his3Δ1 MAL2-8C SUC2), forming the Sc-sTF-background-strain.

The Sc-sTF-background-strain was modified further by integration of the 2BS_ARO4_K229L cassette (FIG. 4). This cassette was integrated into the ARO4 genomic locus such way it replaced the native ARO4 gene and part of its promoter (region −113 to −1 bp counted in respect to ATG-start codon). The 2BS_ARO4_K229L cassette integrated in the genome contained a synthetic promoter, 2BS_114cp (Table 1, cp #1 in FIG. 4), polynucleotide sequence encoding the ARO4_K229L (SEQ ID: 17), and the ARO4 terminator (term #1 in FIG. 4). The resulting strain was called Sc_A4M.

The Sc-sTF-background-strain was also modified by integration of the 2BS_TRP2_ S76L cassette (FIG. 4). This cassette was integrated into the TRP2 genomic locus such way it replaced the native TRP2 gene and part of its promoter (region −122 to −1 bp counted in respect to ATG-start codon). The 2BS_TRP2_S76L cassette integrated in the genome contained a synthetic promoter, 2BS_201cp (Table 1, cp #2 in FIG. 4), polynucleotide sequence encoding the TRP2_S76L (SEQ ID: 18), and the TRP2 terminator (term #2 in FIG. 4). The resulting strain was called Sc_T2M.

The Sc_T2M strain was further modified by integration of the 2BS_TRP3 cassette (FIG. 4). This cassette was integrated into the TRP3 genomic locus such way it replaced the native TRP3 gene and part of its promoter (region −99 to −1 bp counted in respect to ATG-start codon). The 2BS_TRP3 cassette integrated in the genome contained a synthetic promoter, 2BS_533cp (Table 1, cp #3 in FIG. 4), polynucleotide sequence encoding the native TRP3 enzyme, and the TRP3 terminator (term #3 in FIG. 4). The resulting strain was called Sc_T2M_T3.

The Sc_T2M_T3 strain was modified further by integration of the 2BS_ARO4_K229L cassette (FIG. 4). This cassette was integrated into the ARO4 genomic locus such way it replaced the native ARO4 gene and part of its promoter (region −113 to −1 bp counted in respect to ATG-start codon). The 2BS_ARO4_K229L cassette integrated in the genome contained a synthetic promoter, 2BS_114cp (Table 1, cp #1 in FIG. 4), polynucleotide sequence encoding the ARO4_K229L (SEQ ID: 17), and the ARO4 terminator (term #1 in FIG. 4). The resulting strain was called Sc_A4M_T2M_T3.

The correct and single copy integrations were confirmed by qPCR, where the qPCR signal of each integrated cassette (present), and replaced genomic region (absent), was compared to a qPCR signal of a unique native sequence in each strain.

The production of L-tryptophan was determined in the Sc-sTF-background-, Sc_A4M, Sc_T2M_T3, and Sc_A4M_T2M_T3 strains. It was found that intracellular concentration of L-tryptophan was increased, particularly in the Sc_T2M_T3 and Sc_A4M_T2M_T3 strains (FIG. 8). In addition, L-tryptophan was more abundant in Sc_A4M strain culture media (supernatant) as compared to the Sc-sTF-background-strain in the first day of cultivations (FIG. 7). This indicates that the L-tryptophan pathway flux was increased in the Sc_A4M, Sc_T2M_T3, and Sc_A4M_T2M_T3 strains resulting in higher provision of intracellular L-tryptophan.

Example 2—Construction of *Aspergillus niger* Platform Strains with Elevated Metabolic Flux Towards L-Tryptophan The expression cassette for the sTF (FIG. 4) is containing the *A. niger* 008 core promoter (cp #0 in FIG. 4) and the *T. reesei* TEF1 terminator (term #0 in FIG. 4). The sTF gene is encoding a fusion protein composed of the Bm3R1 coding region (NCBI Reference Sequence: WP_013083972.1), SV40 NLS, and the transcription activation domain VP16. This cassette is integrated into the gluC (JGI protein ID 1220513) genomic locus of the parental strain—*Aspergillus niger* ATCC1015 (pyrG-delta), forming the An-sTF-background-strain.

The An-sTF-background-strain is modified further by integration of the 2BS_ARO4_K219L cassette (analogous to 2BS_ARO4_K229L cassette in FIG. 4). This cassette is integrated into the aro4 (JGI protein ID 1181493) genomic locus such way it replaces the native gene and part of its promoter (region −500 to −1 bp counted in respect to ATG-start codon). The 2BS_ARO4_K219L cassette integrated in the genome contains a synthetic promoter, 2BS_114cp (Table 1, cp #1 in FIG. 4), polynucleotide sequence encoding the ARO4_K219L (SEQ ID: 19), and the native aro4 terminator (term #1 in FIG. 4). The resulting strain is called An_A4M.

The An-sTF-background-strain is also modified by integration of the 2BS_TRP2_S83L cassette (analogous to 2BS_TRP2_S76L cassette in FIG. 4). This cassette is integrated into the trp2 (JGI protein ID 1228781) genomic locus such way it replaces the native trp2 gene and part of its promoter (region −500 to −1 bp counted in respect to ATG-start codon). The 2BS_TRP2_S83L cassette integrated in the genome contains a synthetic promoter, 2BS_201cp (Table 1, cp #2 in FIG. 4), polynucleotide sequence encoding the TRP2_S83L (SEQ ID: 20), and the native trp2 terminator (term #2 in FIG. 4). The resulting strain is called An_T2M.

The correct and single copy integrations is confirmed by qPCR, where the qPCR signal of each integrated cassette (present), and replaced genomic region (absent), is compared to a qPCR signal of a unique native sequence in each strain.

Example 3—Construction of Psilocybin-Producing *Saccharomyces cerevisiae* Strains, and Analysis of Psilocybin Production The PsiH-PsiD expression cassettes (FIG. 2) were constructed each containing a bidirectional synthetic promoter 114cp_8BS_201cp (Table 1), the PDC5 terminator for the PsiH gene (term #1 in FIG. 2), and the LEU2 terminator for the PsiD gene (term #2 in FIG. 2). The PsiH-gene DNA was encoding either the PsiH of *Psilocybe cubensis* origin (SEQ ID: 5) or the PsiH of *Psilocybe cyanescens* origin (SEQ ID: 6), the PsiD-gene DNA was encoding either the PsiD of *Psilocybe cubensis* origin (SEQ ID: 1) or the PsiD of *Psilocybe cyanescens* origin (SEQ ID: 2). All combinations were constructed resulting in four different PsiH-PsiD cassettes. The PsiK-PsiM expression cassettes (FIG. 2) were constructed analogously, each containing the bidirectional synthetic promoter 114cp_8BS_201cp (Table 1), the PDC5 terminator for the PsiK gene (term #3 in FIG. 2), and the HIS3 terminator for the PsiM gene (term #4 in FIG. 2). The PsiK-gene DNA was encoding either the PsiK of *Psilocybe cubensis* origin (SEQ ID: 7) or the PsiK of *Psilocybe cyanescens* origin (SEQ ID: 8), the PsiM-gene DNA was encoding either the PsiM of *Psilocybe cubensis* origin (SEQ ID: 3) or the PsiM of *Psilocybe cyanescens* origin (SEQ ID: 4). Again, all combinations constructed used resulting in four different PsiK-PsiM cassettes.

All combinations of the PsiH-PsiD+PsiK-PsiM cassette pairs were integrated into the genome of the yeast strain Sc_A4M generated in Example 1, which resulted in 16 unique psilocybin-producing yeast strains (Table 2). Each PsiH-PsiD cassette was integrated into the leu2-3_112 locus, and each PsiK-PsiM cassette was integrated into the his3Δ1 locus of the strain.

The 16 psilocybin-strains were tested for production of psilocybin. The cultivations were performed in liquid media at 30° C. in 4 ml of YPD (20 g/L bacto peptone, 10 g/L yeast extract, and 40 g/L D-glucose) for 24 hours. The cells were separated from the medium by centrifugation, and the cell pellets as well as the supernatants (media) were analyzed.

The cell pellets samples were homogenized with 1 ml of methanol (100%) by using zirconium-grinding beads with a Retsch mixer mill MM400 homogenizer at 20 Hz for 2 min and subjected to ultrasonication for 15 min. The methanolic suspension was centrifuged at 10000 rpm for 5 min. The liquid phase was transferred to another tube and the cell pellet was re-extracted with 1 ml of methanol. The combined methanolic extract was evaporated to dryness at 40° C. under a gentle stream of nitrogen and reconstituted in 0.2 ml of mobile phase (0.1% formic acid in 20% acetonitrile).

The media samples were freeze-dried and diluted in 0.3 ml of mobile phase (0.1% Formic Acid in 20% Acetonitrile). All samples were filtered (PALL GHP Acrodisc 13 mm syringe filters with polypropylene membrane) to a fresh vials. A 2-microliter volume was subjected to the LC-MS analysis to detect psilocybin and related metabolites.

Analysis was performed on an Acquity UHPLC system, Waters (Milford, MA, USA) and Waters Synapt G2-S MS system Waters (Milford, MA, USA). Chromatography was performed using an ACQUITY UPLC BEH HSS T3, 1.8 μm 2.1×100 mm, (Waters), kept at 30° C. The experiment was carried out at a flow rate of 0.4 ml/min with mobile phase A (0.1% formic acid in water) and B (acetonitrile). The gradient elution started at 5% B and maintained at 5% B for 0.4 min, then increased to 19% B within 5 min, after this directly returned to initial percentage and maintained for 2 min. Mass spectrometry was carried out using electrospray ionization (ESI) in positive polarity. The capillary voltage was 3.0 kV, cone voltage 30 kV, source temperature 150° C. and desolvation temperature 500° C. The cone and desolvation gas flow were set at 150 L/h (nitrogen) and 1000 L/h (nitrogen), respectively, collision gas was 0.15 mL/min.

The analysis was performed with L-tryptophan as an analytical standard, and the concentration of other metabolites was estimated based on the L-tryptophan standard curve. The identity of the metabolites were confirmed by matching the calculated molecular masses with the mass spectrometry signals. Psilocybin was detected only in the cell pellet extracts (Table 2), but not in the culture supernatants. Based on this preliminary test, three strains with the highest psilocybin content were selected for further analysis. These strains containing the psilocybin pathway versions #6, #8, and #9 (Table 2), were grown in 25 ml of YPD and/or SCD medium (6.7 g/L of yeast nitrogen base (Becton, Dickinson and Company), synthetic complete amino acid mixture, 40 g/L D-glucose) for 5 days, and 4 ml culture samples were collected each day. The preparation of the cell pellet and culture media samples for the UPLC-MS analysis was performed as above. Psilocybin, psilocin, L-tryptophan and tryptamine (all Sigma-Aldrich) were used as quantification standards (FIG. 13), for which the calibration curves were prepared from 0.1 to 100 μg/mL. The results from the selected psilocybin-production experiments are shown in FIG. 6 (intracellular metabolites) and FIG. 7 (metabolites in the culture supernatants). In the YPD cultivations (FIG. 6A), the highest intracellular psilocybin content was observed in day 3: ~0.32 mg/g (dry cell weight) in the Sc_A4M strain with the psilocybin pathway #6; ~0.31 mg/g with the pathway #8; and ~0.21 mg/g with the pathway #9. In the SCD cultivations (FIG. 6B), the highest intracellular psilocybin content was observed in day 1 and/or 2: ~1.5 mg/g (dry cell weight) in the Sc_A4M strain with the psilocybin pathway #6; ~1.1 mg/g with the pathway #8; and ~1.0 mg/g with the pathway #9. Relatively low amounts of some metabolites were detected in the culture media in the cultivations of the Sc_A4M strain with the psilocybin pathway #6. No psilocybin, but some psilocin, was detected in the YDP cultures (FIG. 7A), and small amount of psilocybin was detected in later stages of SCD cultivations (FIG. 7B).

The analysis revealed that psilocybin is predominantly retained in the cells, thus further analysis was focused on intracellular metabolites accumulation. The psilocybin pathway versions #6 and #9 were selected for the tests in other *S. cerevisiae* strains, and implemented into the following strains: Sc-sTF-background, Sc_T2M_T3, and Sc_A4M_T2M_T3 strains. The strain were transformed with the corresponding versions of the PsiH-PsiD and PsiK-PsiM cassettes. The PsiH-PsiD cassette was integrated into the leu2-3_112 locus, and the PsiK-PsiM cassette was integrated into the his3Δ1 locus of each strains.

The strains were cultivated either in the YPD medium for 4 days (samples analyzed from days 3 and 4), or in the SCD medium for 2 days (samples analyzed from days 1 and 2). The UPLC-MS results for the intracellular content of the metabolites in strains with the psilocybin pathway version #6 are shown in FIG. 9, and the results for the strains with the psilocybin pathway version #9 are shown in FIG. 10. The highest intracellular psilocybin content was observed in the Sc_T2M_T3 strain with the psilocybin pathway #6 cultivated for 3 days in the YPD medium (FIG. 9A): ~2.5 mg/g (dry cell weight). In addition also psilocin was accumulated in this strain to relatively high level: ~0.7 mg/g (dry cell weight). This level of the psilocybin/psilocin content is analogous to the average native levels of these compounds in the *Psilocybe* mushrooms, making this recombinant host a remarkably efficient producer. Other strains and cultivation conditions resulted in modest production levels of psilocybin, ranging from ~0.5 to ~1.2 mg/g (FIG. 9 and FIG. 10).

The methanol extraction of the psilocybin and related compounds from the cells seemed to be an efficient and simple way to obtain relatively pure compounds (FIG. 14). Especially, when optimal production host and the production conditions are established, leading to high level accumulation of psilocybin and minimal co-production of the psilocybin pathway intermediates, such as in case of the Sc_T2M_T3 strain with the psilocybin pathway #6 cultivated the YPD medium.

Example 4—Construction of Psilocybin-Producing *Aspergillus niger* Strains, and Analysis of Psilocybin Production Similar to example 3, the PsiH-PsiD expression cassettes (FIG. 2) are constructed for tests in *Aspergillus niger*. Each cassette is containing a bidirectional synthetic promoter 114cp_8BS_201cp (Table 1), the ADH1 terminator for the PsiH gene (term #1 in FIG. 2), and the *T. reesei* TEF1 terminator for the PsiD gene (term #2 in FIG. 2). The PsiH-gene DNA is encoding either the PsiH of *Psilocybe cubensis* origin (SEQ ID: 13) or the PsiH of *Psilocybe cyanescens* origin (SEQ ID: 14), the PsiD-gene DNA is encoding either the PsiD of *Psilocybe cubensis* origin (SEQ ID: 9) or the PsiD of *Psilocybe cyanescens* origin (SEQ ID: 10). All combinations are constructed resulting in four different PsiH-PsiD cassettes. The PsiK-PsiM expression cassettes (FIG. 2) are constructed analogously, each containing the bidirectional synthetic promoter 114cp_8BS_201cp (Table 1), the ADH1 terminator for the PsiK gene (term #3 in FIG. 2), and the *T. reesei* TEF1 terminator for the PsiM gene (term #4 in FIG. 2). The PsiK-gene DNA is encoding either the PsiK of *Psilocybe cubensis* origin (SEQ ID: 15) or the PsiK of *Psilocybe cyanescens* origin (SEQ ID: 16), the PsiM-gene DNA is encoding either the PsiM of *Psilocybe cubensis* origin (SEQ ID: 11) or the PsiM of *Psilocybe cyanescens* origin (SEQ ID: 12). Again, all combinations are resulting in four different PsiK-PsiM cassettes.

All (16) combinations of the PsiH-PsiD+PsiK-PsiM cassette pairs are integrated into the genome of the *A. niger* strains (An-sTF-background-strain, An_A4M, An_T2M) generated in Example 2, which results in 48 unique psilocybin-producing *A. niger* strains. Each PsiH-PsiD cassette is integrated into the gaaA locus (JGI protein ID: 1158309), and each PsiK-PsiM cassette is integrated into the gaaC locus (JGI protein ID: 1158310) of the strain.

The *A. niger* psilocybin-strains are tested for the production of psilocybin. The cultivations are performed in liquid media at 28° C. in 20 ml of YPDG medium (20 g/L bacto peptone, 10 g/L yeast extract, 20 g/L D-glucose, and 30 g/L gelatine) for 48 hours. The mycelia are separated from the medium by filtration, and 500 mg of mycelium (wet weight) as well as the supernatants (media) are analyzed. The extraction and the LC-MS analysis is performed according to example 3.

Example 5—Construction of Transient Psilocybin-Producing Tobacco Plant *Nicotiana benthamiana*, and Analysis of Psilocybin Production in the Tobacco Leaves The expression cassette for the sTF (FIG. 2) contained the *Arabidopsis thaliana* MTMC1 core promoter (cp #0; SEQ ID: 25) and the *Arabidopsis thaliana* AT3G15353 terminator (term #0). The sTF gene was encoding a fusion protein composed of the Bm3R1 coding region (NCBI Reference Sequence: WP_013083972.1), SV40 NLS, and the transcription activation domain VP64.

Two PsiH-PsiD expression cassettes (FIG. 2) were constructed each containing a bidirectional synthetic promoter 114cp_8BS_201cp (Table 1), the *Saccharomyces cerevisiae* PDC5 terminator for the PsiH gene (term #1 in FIG. 2), and the *Arabidopsis thaliana* AT2G06520 terminator for the PsiD gene (term #2 in FIG. 2). The PsiH-gene DNA was encoding the PsiH of *Psilocybe cyanescens* origin (SEQ ID: 6), the PsiD-gene DNA was encoding either the PsiD of *Psilocybe cubensis* origin (SEQ ID: 1) or the PsiD of *Psilocybe cyanescens* origin (SEQ ID: 2). Both cassettes were extended with the expression cassette for the sTF, resulting in two different PsiH-PsiD-sTF cassettes. Two PsiK-PsiM expression cassettes (FIG. 2) were constructed analogously, each containing the bidirectional synthetic promoter 114cp_8BS_201cp (Table 1), the PDC5 terminator for the PsiK gene (term #3 in FIG. 2), and the *Arabidopsis thaliana* AT2G06520 terminator for the PsiM gene (term #4 in FIG. 2). The PsiK-gene DNA was encoding either the PsiK of *Psilocybe cubensis* origin (SEQ ID: 7) or the PsiK of *Psilocybe cyanescens* origin (SEQ ID: 8), the PsiM-gene DNA was encoding the PsiM of *Psilocybe cubensis* origin (SEQ ID: 3). Again, both cassettes were extended with the expression cassette for the sTF, resulting in two different PsiK-PsiM-sTF cassettes.

Four *Agrobacterium tumefaciens* strains (EHA105 background) were constructed each carrying plasmid with one expression cassette: 1) *Agrobacterium*-strain-1 with the PsiH-PsiD-sTF cassette, were the PsiH was of *Psilocybe cyanescens* origin and the PsiD was of *Psilocybe cubensis* origin; 2) *Agrobacterium*-strain-2 with the PsiH-PsiD-sTF cassette, were the PsiH was of *Psilocybe cyanescens* origin and the PsiD was of *Psilocybe cyanescens* origin; 3) *Agrobacterium*-strain-3 with the PsiK-PsiM-sTF cassette, were the PsiM was of *Psilocybe cubensis* origin and the PsiK was of *Psilocybe cyanescens* origin; 4) *Agrobacterium*-strain-4 with the PsiK-PsiM-sTF cassette, were the PsiM was of *Psilocybe cubensis* origin and the PsiK was of *Psilocybe cubensis* origin;

In the initial experiment (FIG. 15A), the leaves of *Nicotiana benthamiana* were infiltrated by three different suspensions of *Agrobacterium*-strains: 1) *Agrobacterium*-strain-1, forming PsiD+PsiH part of the psilocybin biosynthetic pathway expressed in the tobacco leaves; 2) *Agrobacterium*-strain-3, forming PsiM+PsiK part of the psilocybin biosynthetic pathway expressed in the tobacco leaves; 3) Mixture of *Agrobacterium*-strain-1 and *Agrobacterium*-strain-3, forming the complete psilocybin biosynthetic pathway #6 (Table 2) expressed in the tobacco leaves. The infiltrated plants were cultivated for 6 days, and samples were taken at days 4 and 6 for the analysis. Each sample was prepared by cutting four identical discs from various areas of the infiltrated leaves, the disks were frozen in liquid nitrogen and grinded to powder with zirconium-grinding beads in a Retsch mixer mill MM400 homogenizer at 29 Hz for 2 min. The milled samples were subjected to extraction and analysis.

The methanol extraction and the UPLC-MS analysis was performed as described in Example 3. Psilocybin, psilocin, L-tryptophan and tryptamine (all Sigma-Aldrich) were used as quantification standards (FIG. 13), for which the calibration curves were prepared from 0.1 to 100 μg/mL. The results from the analysis are shown in FIG. 15A. As expected, psilocybin was produced only when the full pathway was expressed, and it reached approximately 5 mg/g of leaves (dry weight) at day 6 (FIG. 15A).

In the second experiment (FIG. 15B), the leaves of *Nicotiana benthamiana* were infiltrated by four different suspensions of *Agrobacterium*-strains: 1) Mixture of *Agrobacterium*-strain-1 and *Agrobacterium*-strain-4, forming the complete psilocybin biosynthetic pathway #5 (Table 2) expressed in the tobacco leaves; 2) Mixture of *Agrobacterium*-strain-1 and *Agrobacterium*-strain-3, forming the complete psilocybin biosynthetic pathway #6 (Table 2) expressed in the tobacco leaves; 3) Mixture of *Agrobacterium*-strain-2 and *Agrobacterium*-strain-4, forming the complete psilocybin biosynthetic pathway #9 (Table 2) expressed in the tobacco leaves; and 4) Mixture of *Agrobacterium*-strain-2 and *Agrobacterium*-strain-3, forming the complete psilocybin biosynthetic pathway #10 (Table 2) expressed in the tobacco leaves. The infiltrated plants were cultivated for 7 days, and samples were taken at days 5 and 7 for the analysis. The samples were collected, processed, and analyzed as described above. Psilocybin and tryptamine (but not L-tryptophan or psilocin) was detected in all samples, maximum psilocybin at around 3 mg/g of leaves (dry weight) was detected in leaves expressing the psilocybin pathway #5 at day 6 (FIG. 15B).

TABLE 1

DNA sequences of example genetic elements used in construction of hosts with elevated production of L-tryptophan and hosts producing psilocybin. The functional DNA parts are indicated: 8xBm3R1 binding site (bold); core promoters (underlined); ATG (start codon of the target gene - italics). The 114 cp_8BS_201 cp is a bidirectional promoter where the 114 cp and the ATG of the gene under its control is shown in the reverse orientation.
Sequences of synthetic promoters used for expression of the genes

| | |
|---|---|
| 2BS_114 cp for Aro4, SEQ ID NO: 21 | CACCGGAATGAACTTTCATTCCGCTGAAGCTTGTCAATCGGAATGAAGGTTCATTCCGGCTAGT TCTCCCCGGAAACTGTGGCCATATGCCCTGCAGTGCCTGATCACCTTATCAAGTGGCCAAATAT CCCACTATAAAAGGCTTGGGAACCCCTCGTTCTGTCTTACCTTCTATCATCTTACCAAATCCACTC CTCTTCCTTCATACATCAATCTTACCAATCAACTACCTCTACAACTCCAATACACTTAATTAAAA*T G* |
| 2BS_201 cp for Trp2, SEQ ID NO: 22 | GCACGGAATGAACTTTCATTCCGCTGAAGCTTGTCAATCGGAATGAAGGTTCATTCCGGCTAG TTCTCCCCGGAAACTGTGGCCATATGTTCAAAGACTAGGATGGATAAATGGGGTATATAAAGC ACCCTGACTCCCTTCCTCCAAGTTCTATCTAACCAGCCATCCTACACTCTACATATCCACACCAAT CTACTACAATTATTAATTAAAA*TG* |
| 2BS_533 cp for Trp3, SEQ ID NO: 23 | GCACGGAATGAACTTTCATTCCGCTGAAGCTTGTCAATCGGAATGAAGGTTCATTCCGGCTAG TTCTCCCCGGAAACTGTGGCCATATGCGCCCCAAGAGAGCTGAAGATGCTGAGTAGGGTTGTC CAGGCAGCACATATATAAGATGCTTCGTCCCCTCCCATCGAGTCCTTCTTTTCTCTCTCATCAA TCACTCTACTTCCTACTCTACCTTAAACTCTTCACTACTTCATACGATTAACA*ATG* |
| 114 cp_8BS_201 cp for psilocybin, SEQ ID NO: 24 | *CAT*TTTAATTAAGTGTATTGGAGTTGTAGAGGTAGTTGATTGGTAAGATTGATGTATGAAGGA AGAGGAGTGGATTTGGTAAGATGATAGAAGGTAAGACAGAACGAGGGGTTCCCAAGCCTTTT ATAGTGGGATATITGGCCACTTGATAAGGTGATCAGGCACTGCAGGGCATATGGCCACAGTTT CCGGGGAGAACTAGCCGGAATGAACCTTCATTCCGATTGACAAGCTTCAGCGGAATGAAAGT TCATTCCGTGCTTATCTAGAGTCCGGAATGAACCTTCATTCCGTCACATCCTAGGTCTCGGAAT GAATGTTCATTCCGACTAGCCGGAATGAACCTTCATTCCGATTGACAAGCTTCAGCGGAATGA AAGTTCATTCCGTGCTTATCTAGAGTCCGGAATGAACCTTCATTCCGTCACATCCTAGGTCTCG GAATGAATGTTCATTCCGACTAGCCGAGCAAATGCCTGCATATGTTCAAAGACTAGGATGGAT AAATGGGGTATATAAAGCACCCTGACTCCCTTCCTCCAAGTTCTATCTAACCAGCCATCCTACAC TCTACATATCCACACCAATCTACTACAATTATTAATTAAAA*TG* |
| MTMC1 cp for sTF in tobacco, SEQ ID NO: 25 | CCAAAATTGTAATTTACCGAGAATTGTAAATTTACCTGAAAACCCTACGCTATAGTTTCGACTAT AAATACCAAACTTAGGACCTCACTTCAGAATCCCCTCGTCGCTGCGTCTCTCTCCCGCAACCTTC GATTTTCGTTTATTCGCATCCATCGGAGAGAGAAAACAATCAATTAATTAAAA*TG* |

TABLE 2

Initial test of 16 versions of the psilocybin pathway (#1-#16) implemented in the Sc_A4M strain.

| pathway | Metabolites amounts in the cell pellets (mg/g DW) | | | | | |
|---|---|---|---|---|---|---|
| | A | B* | C* | D* | E* | F* |
| #1 | 0.191 | 0.305 | 0.010 | 0.023 | 0.003 | 0.197 |
| #2 | 0.249 | 0.300 | 0.012 | 0.024 | 0.005 | 0.171 |
| #3 | 0.281 | 0.436 | 0.001 | 0.028 | 0.002 | 0.186 |
| #4 | 0.215 | 0.356 | 0.006 | 0.035 | 0.004 | 0.088 |
| #5 | 0.223 | 0.277 | 0.011 | 0.022 | 0.004 | 0.197 |
| #6 | 0.217 | 0.272 | 0.007 | 0.020 | 0.004 | 0.215 |
| #7 | 0.201 | 0.258 | 0.006 | 0.021 | 0.001 | 0.179 |
| #8 | 0.223 | 0.288 | 0.006 | 0.024 | 0.001 | 0.247 |
| #9 | 0.199 | 0.315 | 0.008 | 0.019 | 0.004 | 0.203 |
| #10 | 0.183 | 0.428 | 0.001 | 0.023 | 0.001 | 0.183 |
| #11 | 0.191 | 0.312 | 0.006 | 0.018 | 0.003 | 0.151 |
| #12 | 1.187 | 0.411 | 0.001 | 0.024 | 0.005 | 0.186 |
| #13 | 0.229 | 0.389 | 0.010 | 0.022 | 0.005 | 0.197 |
| #14 | 0.229 | 0.407 | 0.008 | 0.022 | 0.005 | 0.194 |
| #15 | 0.205 | 0.403 | 0.005 | 0.022 | 0.001 | 0.172 |
| #16 | 0.206 | 0.330 | 0.006 | 0.023 | 0.004 | 0.124 |

| pathway | Psilocybin pathway composition | | | |
|---|---|---|---|---|
| | PsiD | PsiH | PsiM | PsiK |
| #1 | *P. cubensis* | *P. cubensis* | *P. cubensis* | *P. cubensis* |
| #2 | *P. cubensis* | *P. cubensis* | *P. cubensis* | *P. cyanescens* |
| #3 | *P. cubensis* | *P. cubensis* | *P. cyanescens* | *P. cyanescens* |
| #4 | *P. cubensis* | *P. cubensis* | *P. cyanescens* | *P. cubensis* |
| #5 | *P. cubensis* | *P. cyanescens* | *P. cubensis* | *P. cubensis* |
| #6 | *P. cubensis* | *P. cyanescens* | *P. cubensis* | *P. cyanescens* |
| #7 | *P. cubensis* | *P. cyanescens* | *P. cyanescens* | *P. cyanescens* |
| #8 | *P. cubensis* | *P. cyanescens* | *P. cyanescens* | *P. cubensis* |
| #9 | *P. cyanescens* | *P. cyanescens* | *P. cubensis* | *P. cubensis* |
| #10 | *P. cyanescens* | *P. cyanescens* | *P. cubensis* | *P. cyanescens* |
| #11 | *P. cyanescens* | *P. cyanescens* | *P. cyanescens* | *P. cyanescens* |
| #12 | *P. cyanescens* | *P. cyanescens* | *P. cyanescens* | *P. cubensis* |
| #13 | *P. cyanescens* | *P. cubensis* | *P. cubensis* | *P. cubensis* |
| #14 | *P. cyanescens* | *P. cubensis* | *P. cubensis* | *P. cyanescens* |
| #15 | *P. cyanescens* | *P. cubensis* | *P. cyanescens* | *P. cyanescens* |
| #16 | *P. cyanescens* | *P. cubensis* | *P. cyanescens* | *P. cubensis* |

Intracellular accumulation of the metabolites in cells cultivated for one day in YPD medium. Metabolites analyzed and shown in the table are: L-tryptophan (A), tryptamine (B*), 4-hydroxytryptamine (C*), norbaeocystin (D*), baeocystin (E*), and psilocybin (F*). Asterisk denotes that the compound identification is based on the MS signature (corresponding to the expected mass), and the quantification is an estimate based on the UPLC signal of L-tryptophan standard. Psilocin was not detected. Three best performing pathways (in bold, based on the psilocybin content) were selected for the time course production test shown in FIG. 6A and 6B. Pathways #5, #6, #9, and #10 were selected for transient expression in tobacco plant *Nicotiana benthamiana* (FIG. 15).

The foregoing description has provided, by way of non-limiting examples of particular implementations and embodiments of the invention, a full and informative description of the best mode presently contemplated by the inventors for carrying out the invention. It is, however, clear to a person skilled in the art that the invention is not restricted to details of the embodiments presented above, but that it can be implemented in other embodiments using equivalent means without deviating from the characteristics of the invention.

Furthermore, some of the features of the above-disclosed aspects and embodiments of this invention may be used to advantage without the corresponding use of other features. As such, the foregoing description should be considered as merely illustrative of the principles of the present invention, and not in limitation thereof. Hence, the scope of the invention is only restricted by the appended patent claims.

In an embodiment at least one component of the compositions or chemical products of the invention has a different chemical, structural or physical characteristic compared to the corresponding natural component from which the at least one component is derived from. In an embodiment said characteristic is at least one of uniform size, homogeneous dispersion, different isoform, different codon degeneracy, different post-translational modification, different methylation, different tertiary or quaternary structure, different enzyme activity, different affinity, different binding activity, and different immunogenicity.

REFERENCES

1. Sherwood A M, Prisinzano TE 2018 Novel psychotherapeutics—a cautiously optimistic focus on hallucinogens. Expert Rev Clin Pharmacol 11: 1-3.
2. Tyls F, et al. 2014 Psilocybin—summary of knowledge and new perspectives. Eur Neuropsychopharmacol 24: 342-356.
3. Passie T, et al. 2002 The pharmacology of psilocybin. Addict Biol 7: 357-364.
4. Shirota O, et al. 2003 Concise large-scale synthesis of psilocin and psilocybin, principal hallucinogenic constituents of "magic mushroom". J Nat Prod 66: 885-887.
5. Fricke J, et al. 2017 Enzymatic synthesis of psilocybin. Angew Chem Int Ed Engl 56: 12352-12355.

The invention claimed is:

1. A recombinant plant host cell comprising:
heterologous polynucleotides encoding PsiD, PsiH, PsiK, and PsiM,
wherein the heterologous polynucleotides are operably linked to at least one promoter which is capable of providing constitutive expression of said heterologous polynucleotides in the recombinant plant host cell;
wherein PsiD has at least 80% amino acid sequence identity with the protein sequence deposited in GenBank accession number ASU62239.1 or the GenBank accession number ASU62242.1, or with the amino acid sequence encoded by polynucleotide SEQ ID NO: 1 or 2 or 9 or 10;
wherein PsiH has at least 80% amino acid sequence identity with the protein sequence deposited in GenBank accession number ASU62246.1 or the GenBank accession number ASU62250.1, or with the amino acid sequence encoded by polynucleotide SEQ ID NO: 5 or 6 or 13 or 14;
wherein PsiK has at least 80% amino acid sequence identity with the protein sequence deposited in Gen- Bank accession number ASU62237.1 or the GenBank accession number ASU62240.1, or with the amino acid sequence encoded by polynucleotide SEQ ID NO: 7 or 8 or 15 or 16;

wherein PsiM has at least 80% amino acid sequence identity with the protein sequence deposited in GenBank accession number ASU62238.1 or the GenBank accession number ASU62241.1, or with the amino acid sequence encoded by polynucleotide SEQ ID NO: 3 or 4 or 11 or 12; and wherein the recombinant plant host cell is capable of producing psilocybin.

2. The recombinant plant host cell of claim 1, wherein the at least one heterologous polynucleotide is operably linked to a single promoter, which controls the expression of each of PsiD, PsiH, PsiK, and PsiM.

3. The recombinant plant host cell of claim 1, wherein the promoter is controlled by a synthetic transcription factor.

4. The recombinant plant host cell of claim 1 comprising a further genetic element encoding at least one of:
Trp2 which has at least 80% amino acid sequence identity with SEQ ID NO: 18 or 20; and
Trp3 which has at least 80% amino acid sequence identity with the sequence corresponding to the GenBank accession number CAA82056.1 or the GenBank accession number OWW28508.1.

5. A method for producing metabolites comprising:
a. providing a recombinant plant host cell comprising:
heterologous polynucleotides encoding PsiD, PsiH, PsiK, and PsiM;
wherein the heterologous polynucleotides are operably linked to at least one promoter which is capable of directing expression of said heterologous polynucleotides in the recombinant plant host cell;
wherein PsiD has at least 80% amino acid sequence identity with the protein sequence deposited in GenBank accession number ASU62239.1 or the GenBank accession number ASU62242.1, or with the amino acid sequence encoded by polynucleotide SEQ ID NO: 1 or 2 or 9 or 10;
wherein PsiH has at least 80% amino acid sequence identity with the protein sequence deposited in GenBank accession number ASU62246.1 or the GenBank accession number ASU62250.1, or with the amino acid sequence encoded by polynucleotide SEQ ID NO: 5 or 6 or 13 or 14;
wherein PsiK has at least 80% amino acid sequence identity with the protein sequence deposited in GenBank accession number ASU62237.1 or the GenBank accession number ASU62240.1, or with the amino acid sequence encoded by polynucleotide SEQ ID NO: 7 or 8 or 15 or 16;

wherein PsiM has at least 80% amino acid sequence identity with the protein sequence deposited in GenBank accession number ASU62238.1 or the GenBank accession number ASU62241.1, or with the amino acid sequence encoded by polynucleotide SEQ ID NO: 3 or 4 or 11 or 12; and wherein the recombinant plant host cell is capable of producing psilocybin;
b. cultivating the recombinant plant host cell in conditions allowing growth and propagation of the recombinant plant host cell;
c. continuing cultivating the recombinant plant host cells to synthesize the metabolites; and
d. recovering at least one metabolite synthesised by an enzyme encoded by the heterologous polynucleotide of the recombinant plant host cell.

6. A psilocybin production system comprising:
a production unit containing the recombinant plant host cell of claim 1; and
a control unit configured to operate the production unit.

7. The recombinant plant host cell of claim 1, having in its genome a single copy of genetic elements encoding anthranilate synthase having a S76L substitution, wherein the amino acid numbering of the anthranilate synthase corresponds to the numbering of SEQ ID NO: 18, and indole-3-glycerol-phosphate synthase.

8. The recombinant plant host cell of claim 7, wherein the genetic elements that encode anthranilate synthase having a S76L substitution, wherein the amino acid numbering of the anthranilate synthase corresponds to the numbering of SEQ ID NO: 18, and indole-3-glycerol-phosphate synthase, are native to the host cell.

9. The recombinant plant host cell of claim 1, wherein the recombinant plant host cell further comprises
genetic elements encoding anthranilate synthase having a S76L substitution, and wherein the amino acid numbering of the anthranilate synthase corresponds to the numbering of SEQ ID NO: 18; and
indole-3-glycerol-phosphate synthase.

10. A plant or a plant part comprising the recombinant plant host cells of claim 1.

11. A tobacco plant or a tobacco plant part comprising the recombinant plant host cells of claim 1.

* * * * *